(12) United States Patent
Mason et al.

(10) Patent No.: US 6,551,820 B1
(45) Date of Patent: Apr. 22, 2003

(54) EXPRESSION OF IMMUNOGENIC HEPATITIS B SURFACE ANTIGENS IN TRANSGENIC PLANTS

(75) Inventors: Hugh S. Mason, Ithaca, NY (US); Yasmin Thanavala, Williamsville, NY (US); Charles Joel Arntzen, Ithaca, NY (US); Elizabeth Richter, Ithaca, NY (US)

(73) Assignee: Boyce Thompson Institute for Plant Research, Ithaca, NY (US)

( * ) Notice: Subject to any disclaimer, the term of this patent is extended or adjusted under 35 U.S.C. 154(b) by 0 days.

(21) Appl. No.: 09/471,573

(22) Filed: Dec. 23, 1999

Related U.S. Application Data

(60) Provisional application No. 60/113,827, filed on Dec. 23, 1998.

(51) Int. Cl.$^7$ .......................... C12N 15/74; C07H 21/04
(52) U.S. Cl. .................. 435/320.1; 435/69.3; 435/71.2; 536/23.4
(58) Field of Search ...................... 536/23.4; 435/320.1, 435/69.3, 71.2

(56) References Cited

U.S. PATENT DOCUMENTS

| | | | |
|---|---|---|---|
| 4,710,463 A | | 12/1987 | Murray |
| 4,847,080 A | | 7/1989 | Neurath et al. |
| 5,380,831 A | * | 1/1995 | Adang et al. |
| 5,484,719 A | | 1/1996 | Lam et al. |
| 5,612,487 A | | 3/1997 | Lam et al. |
| 5,679,880 A | | 10/1997 | Curtiss |
| 5,738,855 A | | 4/1998 | Szu et al. |

FOREIGN PATENT DOCUMENTS

| | | | |
|---|---|---|---|
| EP | 154902 B1 | | 5/1995 |
| WO | WO 96/12801 | * | 5/1996 |

OTHER PUBLICATIONS

Xu–Amano, J., et al, "Journal of Experimental Medicine," Helper T Cell Subsets for Immunoglobulin A Responses, p. 1309–20, (Oct. 20, 1993).

Hugh S. Mason, et al, "Proceedings of the National Academy of Sciences," Expression of hepatitis B surface antigen in transgenic plants, p. 11745–49, (Dec. 20, 1992).

Thanavala, et al., "Proceedings of the National Academy of Sciences," Immunogenicity of transgenic plant–derived hepatitisB surface antigen, p. 3358–61, (Apr. 20, 1995).

De Aizpurua et al. Oral Vaccination: Identification of Classes of Proteins that Provoke an Immune Response upon Oral Feeding, *Journal of Experimental Medicine*, Feb. 1988, vol. 167, pp. 440–451.

International Search Report PCT/US9931020.

\* cited by examiner

*Primary Examiner*—Donna Wortman
(74) *Attorney, Agent, or Firm*—Kathleen M. Williams; Elizabeth N. Spar; Palmer & Dodge LLP

(57) ABSTRACT

Plant expression vectors comprising at least two expression cassettes are provided which function to reduce transcriptional silencing of polynucleotide expression. Further, novel plant expression vectors for expression of immunogenic polypeptides, including HBsAg, are provided. The plant expression vectors can be used to produce immunogenic polypeptides, including HBsAg, in edible plant tissues. The edible plant tissues can be used to elicit an immune response in humans and animals when the plant tissues are consumed.

41 Claims, 36 Drawing Sheets

FIG. 1A

Coding region constructs
    HBsAg coding sequence + 5' & 3' UTRs
    HB102

HBsAg UTRs deleted
    HB103

HBsAg-SEKDEL
    HB105

HBsAg + αS signal peptide
    HB106

HBsAg + αL signal peptide
    HB107

HBsAg + TPSS plastid transit peptide
    HB110

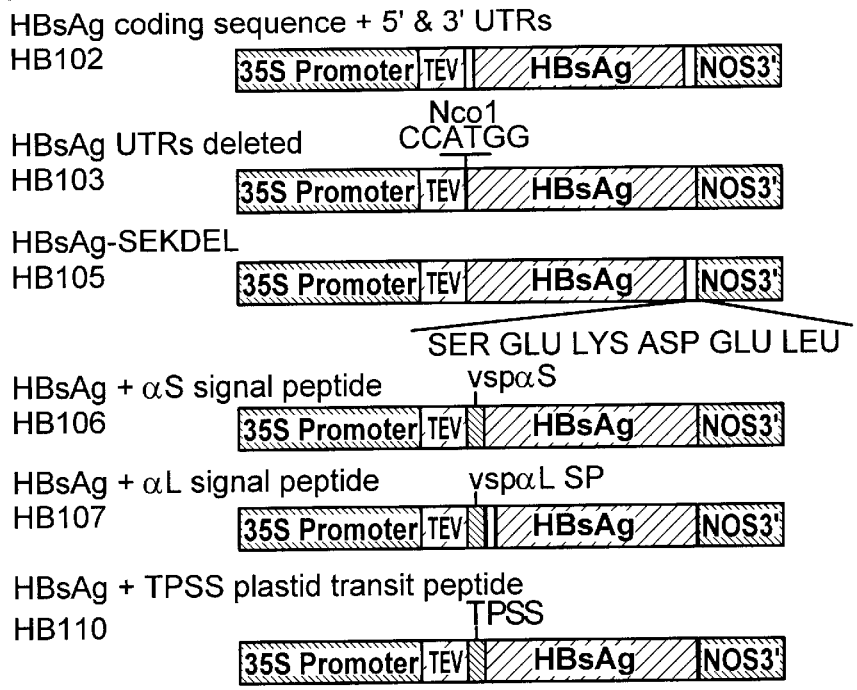

3' constructs
    HBsAg VSP 3'
    HB104

HBsAg PIN2 3'
    HB114

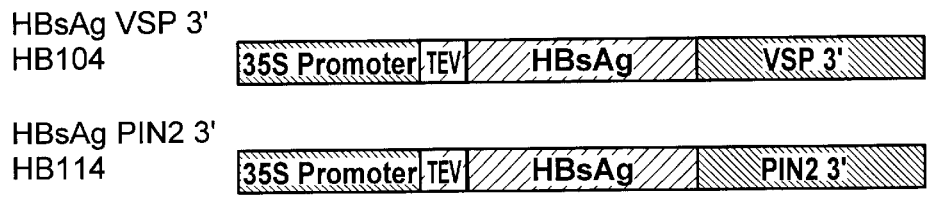

Promoter and leader constructs
    HBsAg-SEKDEL Patatin Promoter
    HB145

HBsAg-SEKDEL GBSS Promoter
    HB165

HBsAg Omega leader
    HB111

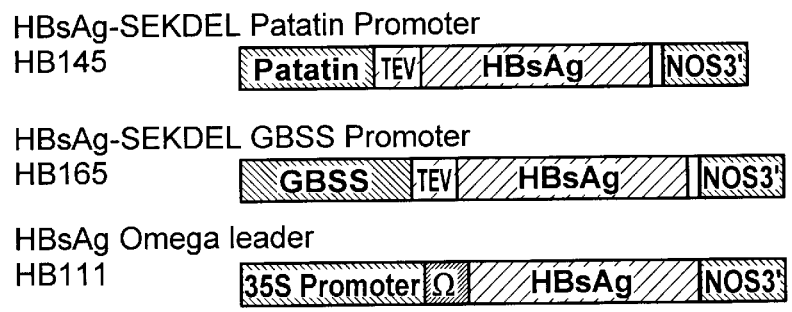

Synthetic HBsAg constructs
    sHBsAg VSP 3'
    HB115 sHBsAg + αL signal peptide
    HB116

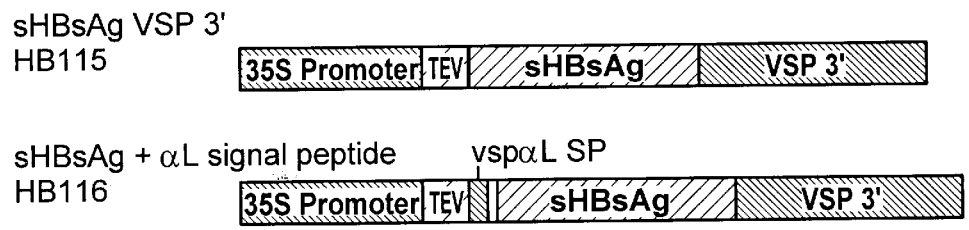

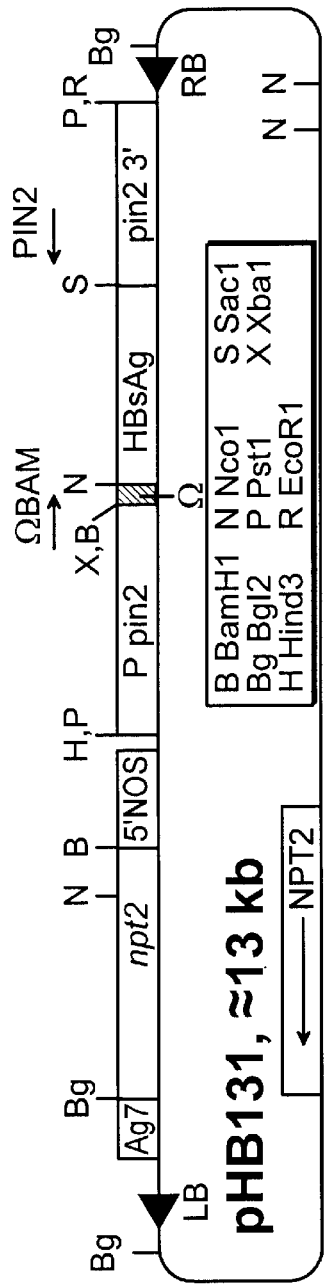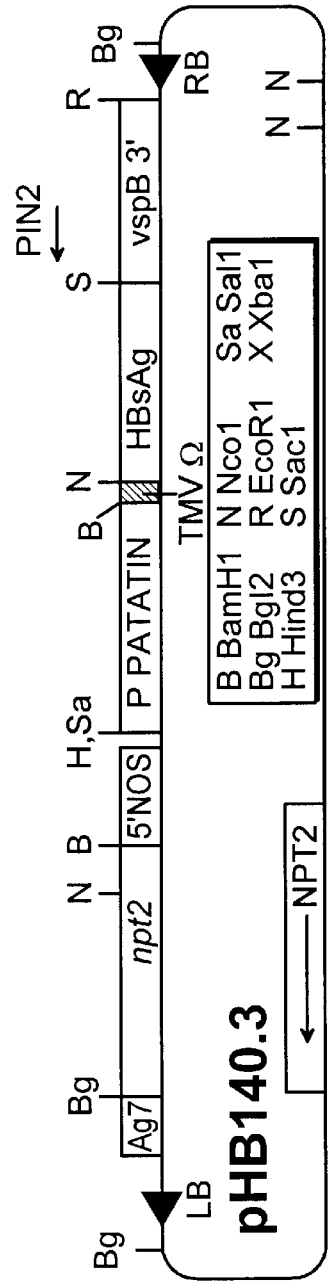
pHB131 CONTAINS THE POTATO *pin2* PROMOTER DRIVING TRANSCRIPTION OF THE NATIVE HBsAg CODING SEQUENCE, AND THE *pin2* TERMINATOR FUSED 3', IN THE *AGROBACTERIUM* BINARY VECTOR pGP

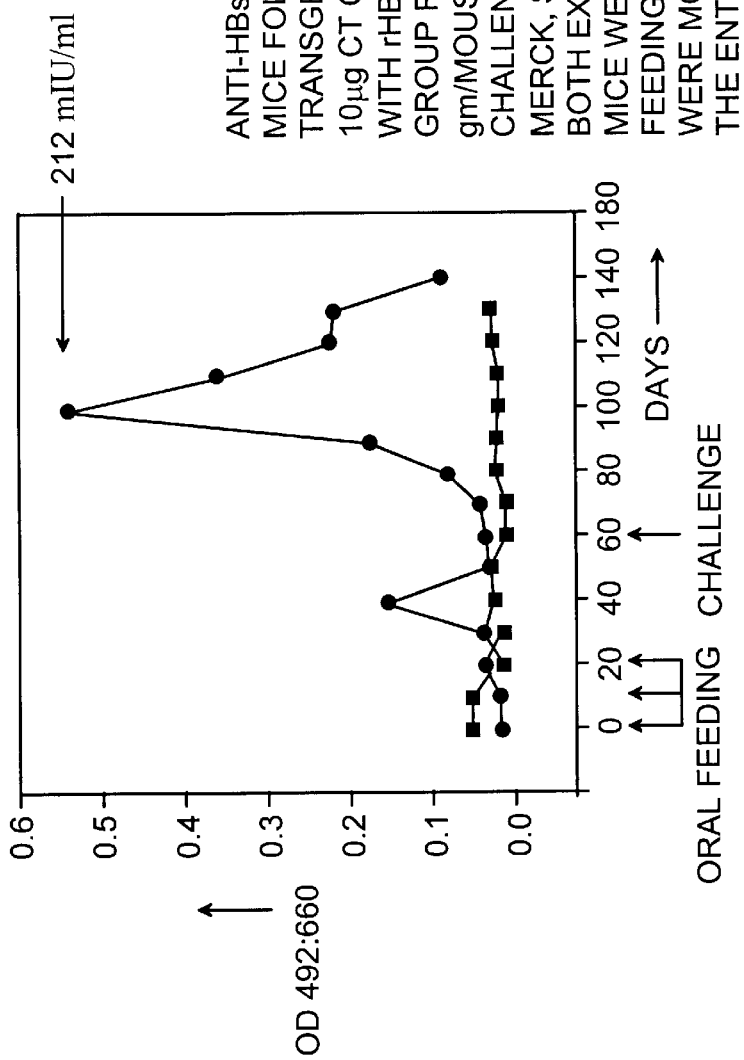

FIG. 3

ANTI-HBsAg ANTIBODY RESPONSES ELICITED IN MICE FOLLOWING ORAL FEEDING WITH HBsAg-TRANSGENIC POTATOES (5 gm/MOUSE) PLUS 10µg CT ON DAYS 0, 10 AND 20, AND CHALLENGED WITH rHBsAg 0.5 µg i.p. ON DAY 60 (●), A CONTROL GROUP RECEIVED CONTROL POTATO (5 gm/MOUSE) PLUS 10 µg CT AND WERE CHALLENGED WITH rHBsAg (YEAST DERIVED, MERCK, SHARP & DOHME) 0.5 µg ON DAY 60 (■). BOTH EXPERIMENTAL AND CONTROL GROUPS OF MICE WERE FASTED OVERNIGHT PRIOR TO FEEDING THE POTATOES. INDIVIDUAL MICE WERE MONITORED TO VERIFY CONSUMPTION OF THE ENTIRE DOSE. RESULTS ARE EXPRESSED AS OD 492:660 nm.

Plant-optimized pre S1/S2
(Note: The last "M" residue is the first "M" of the S protein.)

```
ATG GGA CAA AAT CTT TCA ACC AGC AAT CCT TTG GGA TTC TTT CCA GAC CAC CAA CTT
 M   G   Q   N   L   S   T   S   N   P   L   G   F   F   P   D   H   Q   L

GAT CCA GCC TTC AGA GCA AAC ACT GCA AAT CCA GAT TGG GAC TTC AAT CCC AAC AAG
 D   P   A   F   R   A   N   T   A   N   P   D   W   D   F   N   P   N   K

GAC ACC TGG CCA GAT GCC AAC AAG GTG GGA GCA GCT GGA GCA TTT GGA TTG GGT TTC ACC
 D   T   W   P   D   A   N   K   V   G   A   A   G   A   F   G   L   G   F   T

CCA CCA CAT GGT GGC CTT GGC CCT CAA GCT CAA GGC ATC TTG CAA CCT ACT
 P   P   H   G   G   L   G   P   Q   A   Q   G   I   L   Q   P   T

TTG CCA GCA AAT CCA CCT CCA CCT TTG AGA AAC ACT CAT CCT CAA TGG AGG CAA CCT ACC
 L   P   A   N   P   P   P   P   L   R   N   T   H   P   Q   W   R   Q   P   T

CCA TTG TCT CCA CCT TTG CAA ACT TTG CAA GAT CCC AGA GTG AGA GGC TTG TAT TTC CCT GCT GGT
 P   L   S   P   P   L   Q   T   L   Q   D   P   R   V   R   G   L   Y   F   P   A   G

ACC TTC CAC CAA CAA CTT ATG CAA TCA GCC ATG CAA TGG AAC TCA ACA
 T   F   H   Q   Q   L   M   Q   S   A   M   Q   W   N   S   T

GGC TCA AGC TCA GGA ACA GTG AAC CCT GTT TTG ACT ACT GCC TCT CCC TTG TCC TCA
 G   S   S   S   G   T   V   N   P   V   L   T   T   A   S   P   L   S   S

ATC TTC AGC AGA ATT GGA GAC CCT GCT TTG AAC ATG
 I   F   S   R   I   G   D   P   A   L   N   M
```

FIG. 5

SYNTHETIC HBsAg CONSTRUCTS sHBsAgg VSP 3' aa mutation
HB115

| 35S | TEV | sHBsAg | VSP 3' | sHBsAg + αL signal peptide aa mutation
HB116 vspαL

| 35S | TEV | | sHBsAg | VSP 3' | sHBsAg VSP 3'
HB117

| 35S | TEV | sHBsAg | VSP 3' | sHBsAg + αS signal peptide
HB118 vspαS

| 35S | TEV | | sHBsAg | VSP 3' | sHBsAg + αL signal peptide
HB119 vspαL

| 35S | TEV | | sHBsAg | VSP 3' | sHBsAg E8 promoter + pin2 3'
HB120

| E8 Promoter | sHBsAg | Pin2 3' | sHBsAg + SEKDEL + pin2 3'
HB121

KDEL

| 35S | TEV | sHBsAg | | Pin2 3' | sHBsAg + αS signal peptide + KDEL
HB122 vspαS    KDEL

| 35S | TEV | | sHBsAg | | Pin2 3' | sHBsAg + αL signal peptide + KDEL
HB123 vspαL    KDEL

| 35S | TEV | | sHBsAg | | Pin2 3' |

FIG. 21

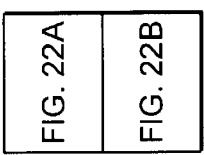

FIG. 22

Wild-type HBsAg sequence
One RNA PolII termination sequence (underlined) was found. There are 29 CnG trimers and 16 CG dimers.

```
ATGGAGAACA CAACATCAGG ATTCCTAGGA CCCCTGCTCG TGTTACAGGC GGGGTTTTTC TTGTTGACAA
GAATCCTCAC AATACCACAG AGTCTAGACT CGTGGTGGAC TTCTCTCAAT TTTCTAGGGG GAGCACCCAC
GTGTCTTGGC CAAAATTCGC AGTCCCCAAC CTCCAATCAC CTTGTCCTCC CTGTCCCTCC AATTTGTCCT
GGTTATCGTT GGATGTGTCT GCGGCGTTTT ATCATATTCC TCTTCATCCT GCTGCTATGC CTCATCTTCT
TGTTGGTTCT TCTGGACTAC CAAGGTATGT TGCCCGTTTG TCCTCTACTT CCAAGAACAT CAACTACCAG
CACGGACCA TGCAAGACCT GCACGATTCC TGCTCAAGGA ACCTCTATGT TTCCCTCTTG TTGCTGTACA
AAACCTTCGG ACGGAAACTG CACTTGTATT CCCATCCCAT CATCTTGGGC TTTCGCAAGA TTCCTATGGG
AGTGGGCCTC AGTCCGTTTC TCCTGGCTCA GTTTACTAGT GCCATTTGTT CAGTGGTTCG TAGGCTTTC
CCCCACTGTT TGGCTTTCAG TTATATGGAT GATGTGGTAT TGGGGGCCAA GTCTGTACAA CATCTTGAGT
CCCTTTTTAC CTCTATTACC AATTTCTTT TGTCTTTGGG TATACATTTG A
```

FIG. 22A

Final HBV-Ag Synthetic sequence, (sHBV-Ag):

```
     NcoI
CGACCATGGA GAACACAACA TCAGGATTCT TGGGACCCCT CTTGGTGCTC CAAGCTGGAT TCTTCTTGTT
HincII
GACAAGAATC CTCACAATCC CACAATCTTT GGACTCTTGG TGGACTTCTC TCAACTTCTT GGGAGGAGCA
CCCACTTGTC TTGGCCAAAA TAGCCAATCC CCAACCTCCA ACCACTCACC AACCTCTGT CCTCCAATTT
GTCCTGGTTA TAGGTGGATG TGTTTGAGGA GGTTCATCAT CTTCCTCTCT ATCCTCCTCT TGTGCCTCAT
CTTCTTGTTG GTTCTTTTGG ACTACCAAGG TATGTTGCCA GTTTGTCCTC TCCTTCCAAG AACATCAACT
ACTAGCACTG GACCATGCAA GACTTGCACC ATCCCTGCTC AAGGAACCTC TATGTTCCCC TCTTGTTGTT
                                                      BstXI
GTACAAAGCC TTCTGATGGA AATTGCACTT GTATCCCCAT CCCATACATCT TGGGCTTTTG CAAGATTCTT
GTGGGAGTGG GCCTCAGTGA GGTTCTCTTG GTTGAGCCTC TTGGTGCCAT TTGTTCAATG GTTTGTGGGA
CTTTCCCCCA CTGTTTGGCT TTCAGTTATT TCCCCAATCT ACCAAGCCTC TACAACATCT
                                                      BbsI                SacI
TGAGCCCCTT CCTCCCCTCT CCTCCCCTCT CTTTTGTCT ATCTAAGTCT TCGAGCTCCC
```

FIG. 22B

| FIG. 23A |
| FIG. 23B |
| FIG. 23C |
| FIG. 23D |

FIG. 23

Amino Acid sequence and comparison of coding sequence region of sHBV-AG with wildtype sHBV CDS

```
              1                                                           60
HBV_Ag_Wild   AACATGGAGAACACAACATCAGGATTCCTAGGACCCCTGCTCGTGTTACAGGCGGGGTTT
              M  E  N  T  T  S  G  F  L  G  P  L  L  V  L  Q  A  G  F
HBV_Ag_Syn.   ACCATGGAGAACACAACATCAGGATTCCTAGGACCCCTGCTCGTGTTACAAGCTGGATTC 61                                                          120
HBV_Ag_Wild   TTCTTGTTGACAAGAATCCTCACAATACCACAGAGTCTAGACTCGTGGTGGACTTCTCTC
              F  L  L  T  R  I  L  T  I  P  Q  S  L  D  S  W  W  T  S  L
HBV_Ag_Syn.   TTCTTGTTGACAAGAATCCTCACAATCCCACAAAGCTTGGACTCTTGGTGGACTTCTCTC
```

FIG. 23A

```
                    121                                                           180
HBV_Ag_Wild         AATTTCTAGGGGAGCACCCACGTGTCTTGGCCAAAATTCGCAGTCCCCAACCTCCAAT
                     N  F  L  G  G  A  P  T  C  L  G  Q  N  S  Q  S  P  T  S  N
HBV_Ag_Syn.         AACTTCTTGGGAGGAGCACCCACCACTGTCTTGGCCAAATAGCCAATCCCCAACCTCCAAC 181                                                           240
HBV_Ag_Wild         CACTCACCAACCTCTGTCCTCCAATTGTCCTCCTGGTTATCGTTGGATGTGTCTGCGGCGT
                     H  S  P  T  S  C  P  P  I  C  P  G  Y  R  W  M  C  L  R  R
HBV_Ag_Syn.         CACTCACCAACCTCTTGTCCTCCAATTGTCCTGGTTATAGGTGGATGTGTTGAGGAGG 241                                                           300
HBV_Ag_Wild         TTTATCATATTCCTCTTCATCCTGCTATGCCTCATCTTCTTGTTGGTTCTTCTGGAC
                     F  I  F  L  F  I  L  L  C  L  I  F  L  L  V  L  L  D
HBV_Ag_Syn.         TTCATCATCTTCCTCTTCATCCTTGTGCCCTCATCTTCTTGTTGGTTCTTTGGAC
```

FIG. 23B

```
             301                                                        360
HBV_Ag_Wild  TACCAAGGTATGTTGCCCGTTTGTCCTCTACTTCCAAGAACATCAACTACCAGCACGGGA
              Y  Q  G  M  L  P  V  C  P  L  L  P  R  T  S  T  T  S  T  G
HBV_Ag_Syn.  TACCAAGGTATGTTGCCAGTTTGTCCTCTCCTTCCAAGAACATCAACTACTAGCACTGGA 361                                                        420
HBV_Ag_Wild  CCATGCAAGACCTGCACGATTCCTGCTCAAGGAACCTCTATGTTTCCCTCTTGTTGCTGT
              P  C  K  T  C  T  I  P  A  Q  G  T  S  M  F  P  S  C  C  C
HBV_Ag_Syn.  CCATGCAAGACTTGCACCATCCCTGCTCAAGGAACCTCTATGTTCCCCTCTTGTTGTTGT 421                                                        480
HBV_Ag_Wild  ACAAAACCTTCGGACGGAAACTGCACTTGTATTCCCATCCCATCATCTTGGGCTTTCGCA
              T  K  P  S  D  G  N  C  T  C  I  P  I  P  S  S  W  A  F  A
HBV_Ag_Syn.  ACAAAGCCTTCTGATGGAAATTGCACTTGTATCCCCATCCCATCATCTTGGGCTTTTGCA
```

FIG. 23C

```
HBV_Ag_Wild    481 AGATTCCTATGGGAGTGGGCCTCAGTCCGTTTCTCCTGGCTCAGTTTACTAGTGCCATTT
                   R  F  L  W  E  W  A  S  V  R  F  S  W  L  S  L  L  V  P  F
HBV_Ag_Syn.        AGATTCTTGTGGGAGTGGGCCTCAGTCCGTTTCTCTTGGCCTTCTTGAGCCTCTTGGTGCCATTT HBV_Ag_Wild    541 GTTCAGTGGTTCGTAGGGCTTTCCCCCACTGTTGGCTTTCAGTTATATGGATGATGTGG
                   V  Q  W  F  V  G  L  S  P  T  V  W  L  S  V  I  W  M  M  W
HBV_Ag_Syn.        GTTCAATGGTTTGTGGGACTTTCCCCCACTGTTTGGCTTTCAGTTATTTGGATGATGTGG HBV_Ag_Wild    601 TATTGGGGCCAAGTCTGTACAACATCTTGAGTCCCTTTTTACCTCTATTACCAATTTC
                   Y  W  G  P  S  L  Y  N  I  L  S  P  F  L  P  L  L  P  I  F
HBV_Ag_Syn.        TATTGGGGACCAAGCCTCTACAACATCTTGAGCCCTTTCCTCCTCCTCCTCCCAATCTTC HBV_Ag_Wild    661 TTTTGTCTTTGGGTATACATTTGA
                   F  C  L  W  V  Y  I
HBV_Ag_Syn.        TTTTGTCTTTGGGTGTACATCTAA
```

FIG. 23D

SEQUENCE LISTING

<160> NUMBER OF SEQ ID NOS: 41

<210> SEQ ID NO 1
<211> LENGTH: 681
<212> TYPE: DNA
<213> ORGANISM: Unknown
<220> FEATURE:
<223> OTHER INFORMATION: Hepatitis B surface antigen
<221> NAME/KEY: misc_feature
<223> OTHER INFORMATION: Hepatitis B surface antigen

<400> SEQUENCE: 1

```
atggagaaca caacatcagg attcctagga cccctgctcg tgttacaggc ggggtttttc      60
ttgttgacaa gaatcctcac aataccacag agtctagact cgtggtggac ttctctcaat     120
tttctagggg gagcacccac gtgtcttggc caaaattcgc agtccccaac ctccaatcac     180
tcaccaacct cttgtcctcc aatttgtcct ggttatcgtt ggatgtgtct gcggcgtttt     240
atcatattcc tcttcatcct gctgctatgc ctcatcttct tgttggttct ctggactac      300 caaggtatgt tgcccgtttg tcctctactt ccaagaacat caactaccag cacgggacca     360
tgcaagacct gcacgattcc tgctcaagga acctctatgt tccctcttg ttgctgtaca      420 aaaccttcgg acggaaactg cacttgtatt cccatcccat catcttgggc tttcgcaaga     480
ttcctatggg agtgggcctc agtccgtttc tcctggctca gtttactagt gccatttgtt     540
cagtggttcg tagggctttc ccccactgtt tggctttcag ttatatggat gatgtggtat     600
tgggggccaa gtctgtacaa catcttgagt ccctttttac ctctattacc aattttcttt     660
tgtctttggg tatacatttg a                                              681
```

-continued

```
<210> SEQ ID NO 2
<211> LENGTH: 226
<212> TYPE: PRT
<213> ORGANISM: Unknown
<220> FEATURE:
<223> OTHER INFORMATION: Wild-type HBsAg amino acid sequece
<221> NAME/KEY: misc_feature
<223> OTHER INFORMATION: Wild-type HBsAg amino acid sequece

<400> SEQUENCE: 2

Met Glu Asn Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ala Pro Thr Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Leu Pro Arg
            100                 105                 110

Thr Ser Thr Thr Ser Thr Gly Pro Cys Lys Thr Cys Thr Ile Pro Ala
        115                 120                 125

Gln Gly Thr Ser Met Phe Pro Ser Cys Cys Cys Thr Lys Pro Ser Asp
    130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Ile
        195                 200                 205

Leu Ser Pro Phe Leu Pro Leu Leu Pro Ile Phe Phe Cys Leu Trp Val
    210                 215                 220

Tyr Ile
225

<210> SEQ ID NO 3
<211> LENGTH: 700
<212> TYPE: DNA
<213> ORGANISM: Unknown
<220> FEATURE:
<223> OTHER INFORMATION: Plant optimized HBsAg sequence
<221> NAME/KEY: misc_feature
<223> OTHER INFORMATION: Plant optimized HBsAg sequence

<400> SEQUENCE: 3
cgaccatgga gaacacaaca tcaggattct tgggacccct cttggtgctc caagctggat     60
tcttcttgtt gacaagaatc ctcacaatcc cacaatcttt ggactcttgg tggacttctc    120
tcaacttctt gggaggagca cccacttgtc ttggccaaaa tagccaatcc ccaacctcca    180
accactcacc aacctcttgt cctccaattt gtcctggtta taggtggatg tgtttgagga    240
ggttcatcat cttcctcttc atcctcctct tgtgcctcat cttcttgttg gttcttttgg    300
```

```
actaccaagg tatgttgcca gtttgtcctc tccttccaag aacatcaact actagcactg    360
gaccatgcaa gacttgcacc atccctgctc aaggaacctc tatgttcccc tcttgttgtt    420
gtacaaagcc ttctgatgga aattgcactt gtatccccat cccatcatct tgggcttttg    480
caagattctt gtgggagtgg gcctcagtga ggttctcttg gttgagcctc ttggtgccat    540
ttgttcaatg gtttgtggga ctttcccccca ctgtttggct ttcagttatt tggatgatgt    600
ggtattgggg accaagcctc tacaacatct tgagccccett cctccctctc ctcccaatct    660
tcttttgtct ttgggtgtac atctaagtct tcgagctccc                          700
```

```
<210> SEQ ID NO 4
<211> LENGTH: 6
<212> TYPE: PRT
<213> ORGANISM: Unknown
<220> FEATURE:
<223> OTHER INFORMATION: Microsomal retention signal
<221> NAME/KEY: misc_feature
<223> OTHER INFORMATION: Microsomal retention signal

<400> SEQUENCE: 4

Ser Glu Lys Asp Glu Leu
1               5
```

```
<210> SEQ ID NO 5
<211> LENGTH: 492
<212> TYPE: DNA
<213> ORGANISM: Unknown
<220> FEATURE:
<223> OTHER INFORMATION: Plant optimized sequence for pre-S (pre-S1/S2)
<221> NAME/KEY: misc_feature
<223> OTHER INFORMATION: Plant optimized sequence for pre-S (pre-S1/S2)

<400> SEQUENCE: 5
atgggacaaa atctttcaac cagcaatcct ttgggattct ttccagacca ccaacttgat    60
ccagccttca gagcaaacac tgcaaatcca gattgggact caatcccaa caaggacacc    120 tggccagatg ccaacaaggt gggagctgga gcatttggat tgggtttcac cccaccacat    180
ggtggccttt tgggatggag ccctcaagct caaggcatct tgcaaacttt gccagcaaat    240
ccacctcctg cctcaaccaa tagacaatca ggaaggcaac ctaccccatt gtctccacct    300
ttgagaaaca ctcatcctca agccatgcaa tggaactcaa caaccttcca ccaaactttg    360
caagatccca gagtgagagg cttgtatttc cctgctggtg gctcaagctc aggaacagtg    420
aaccctgttt tgactactgc ctctcccttg tcctcaatct tcagcagaat tggagaccct    480
gctttgaaca tg                                                        492
```

```
<210> SEQ ID NO 6
<211> LENGTH: 12
<212> TYPE: PRT
<213> ORGANISM: Unknown
<220> FEATURE:
<223> OTHER INFORMATION: Isolated peptide homologous to "a" determinant
      of HBsAg
<221> NAME/KEY: misc_feature
<223> OTHER INFORMATION: Isolated peptide homologous to "a" determinant
      of HBsAg

<400> SEQUENCE: 6

Ala Val Cys Thr Arg Gly His Gly Ser Ser Leu Tyr
1               5                   10
```

```
<210> SEQ ID NO 7
<211> LENGTH: 26
```

-continued

```
<212> TYPE: DNA
<213> ORGANISM: Unknown
<220> FEATURE:
<223> OTHER INFORMATION: Isolated oligonucleotide HBNco
<221> NAME/KEY: misc_feature
<223> OTHER INFORMATION: Isolated oligonucleotide HBNco

<400> SEQUENCE: 7
catgccatgg agaacacaac atcagg                                      26

<210> SEQ ID NO 8
<211> LENGTH: 29
<212> TYPE: DNA
<213> ORGANISM: Unknown
<220> FEATURE:
<223> OTHER INFORMATION: Isolated oligonucleotide HBSac
<221> NAME/KEY: misc_feature
<223> OTHER INFORMATION: Isolated oligonucleotide HBSac

<400> SEQUENCE: 8
gccggagctc aaatgtatac ccaaagaca                                   29

<210> SEQ ID NO 9
<211> LENGTH: 30
<212> TYPE: DNA
<213> ORGANISM: Unknown
<220> FEATURE:
<223> OTHER INFORMATION: Isolated oligonucleotide aSEKDELs-F
<221> NAME/KEY: misc_feature
<223> OTHER INFORMATION: Isolated oligonucleotide aSEKDELs-F

<400> SEQUENCE: 9
atactctgag aaagatgagc tatgagagct                                  30

<210> SEQ ID NO 10
<211> LENGTH: 24
<212> TYPE: DNA
<213> ORGANISM: Unknown
<220> FEATURE:
<223> OTHER INFORMATION: Isolated oligonucleotide aSEKDELs-R
<221> NAME/KEY: misc_feature
<223> OTHER INFORMATION: Isolated oligonucleotide aSEKDELs-R

<400> SEQUENCE: 10
ctcatagctc atctttctca gagt                                        24

<210> SEQ ID NO 11
<211> LENGTH: 65
<212> TYPE: DNA
<213> ORGANISM: Unknown
<220> FEATURE:
<223> OTHER INFORMATION: Sequence encoding soybean VSP "alpha-S"
      signal peptide
<221> NAME/KEY: misc_feature
<223> OTHER INFORMATION: Sequence encoding soybean VSP "alpha-S"
      signal peptide

<400> SEQUENCE: 11
ccatggcaat gaaggtcctt gttttcttcg ttgctacaat tttggtagca tggcaatgcc  60
atacc                                                             65

<210> SEQ ID NO 12
<211> LENGTH: 107
<212> TYPE: DNA
<213> ORGANISM: Unknown
<220> FEATURE:
<223> OTHER INFORMATION: Sequence encoding 34 amino acid VSP "alpha-L"
      signal peptide
```

<221> NAME/KEY: misc_feature
<223> OTHER INFORMATION: Sequence encoding 34 amino acid VSP "alpha-L"
      signal peptide

<400> SEQUENCE: 12
ccatggcaat gaaggtcctt gttttcttcg ttgctacaat tttggtagca tggcaatgcc      60
atgcgtacga tatgttccct ctccgaatga acactggcta tggtgcc                  107

<210> SEQ ID NO 13
<211> LENGTH: 65
<212> TYPE: DNA
<213> ORGANISM: Unknown
<220> FEATURE:
<223> OTHER INFORMATION: Sequence encoding 21 amino acid VSP "alpha-S"
      signal peptide
<221> NAME/KEY: misc_feature
<223> OTHER INFORMATION: Sequence encoding 21 amino acid VSP "alpha-S"
      signal peptide

<400> SEQUENCE: 13
ccatggcaat gaaggtcctt gttttcttcg ttgctacaat tttggtagca tggcaatgcc      60
atacc                                                                  65

<210> SEQ ID NO 14
<211> LENGTH: 107
<212> TYPE: DNA
<213> ORGANISM: Unknown
<220> FEATURE:
<223> OTHER INFORMATION: Sequence encoding 34 amino acid VSP "alpha-L"
      signal peptide
<221> NAME/KEY: misc_feature
<223> OTHER INFORMATION: Sequence encoding 34 amino acid VSP "alpha-L"
      signal peptide

<400> SEQUENCE: 14
ccatggcaat gaaggtcctt gttttcttcg ttgctacaat tttggtagca tggcaatgcc      60
atgcgtacga tatgttccct ctccgaatga acactggcta tggtgcc                  107

<210> SEQ ID NO 15
<211> LENGTH: 253
<212> TYPE: DNA
<213> ORGANISM: Unknown
<220> FEATURE:
<223> OTHER INFORMATION: Sequence encoding 82 amino acids of pea rbcS
<221> NAME/KEY: misc_feature
<223> OTHER INFORMATION: Sequence encoding 82 amino acids of pea rbcS

<400> SEQUENCE: 15
ccatggcttc tatgatatct tcttccgctg tgacaacagt cagccgtgcc tctagggggc      60
aatccgccgc aatggctcca ttcggcggcc tcaaatccat gactggattc ccagtgaaga     120
aggtcaacac ttgacattac ttccattaca agcaatggtg gaagagtaaa gtgcatgcag     180
gtgtggcctc caattggaaa gaagaagttt gagactcttt cctatttgcc accattgacc     240
agagattcca tgg                                                       253

<210> SEQ ID NO 16
<211> LENGTH: 25
<212> TYPE: DNA
<213> ORGANISM: Unknown
<220> FEATURE:
<223> OTHER INFORMATION: PCR primer 5'TPSS
<221> NAME/KEY: misc_feature
<223> OTHER INFORMATION: PCR primer 5'TPSS

<400> SEQUENCE: 16

```
ggatccatgg cttctatgat atctt                                              25

<210> SEQ ID NO 17
<211> LENGTH: 29
<212> TYPE: DNA
<213> ORGANISM: Unknown
<220> FEATURE:
<223> OTHER INFORMATION: PCR primer 3'TPSS
<221> NAME/KEY: misc_feature
<223> OTHER INFORMATION: PCR primer 3'TPSS

<400> SEQUENCE: 17
ggatccatgg aatctctggt caatggtgg                                          29

<210> SEQ ID NO 18
<211> LENGTH: 27
<212> TYPE: DNA
<213> ORGANISM: Unknown
<220> FEATURE:
<223> OTHER INFORMATION: Mutagenic primer "Omega-Bam"
<221> NAME/KEY: misc_feature
<223> OTHER INFORMATION: Mutagenic primer "Omega-Bam"

<400> SEQUENCE: 18
gatcggatcc ttacaacaat taccaac                                            27

<210> SEQ ID NO 19
<211> LENGTH: 18
<212> TYPE: DNA
<213> ORGANISM: Unknown
<220> FEATURE:
<223> OTHER INFORMATION: PCR primer "NOS"
<221> NAME/KEY: misc_feature
<223> OTHER INFORMATION: PCR primer "NOS"

<400> SEQUENCE: 19
cggcaacagg attcaatc                                                      18

<210> SEQ ID NO 20
<211> LENGTH: 24
<212> TYPE: DNA
<213> ORGANISM: Unknown
<220> FEATURE:
<223> OTHER INFORMATION: Isolated oligonucleotide cleavage recognition
      site
<221> NAME/KEY: misc_feature
<223> OTHER INFORMATION: Isolated oligonucleotide cleavage recognition
      site

<400> SEQUENCE: 20
atctctgaga aggatgagct ttaa                                               24

<210> SEQ ID NO 21
<211> LENGTH: 24
<212> TYPE: DNA
<213> ORGANISM: Unknown
<220> FEATURE:
<223> OTHER INFORMATION: Isolated oligonucleotide cleavage recognition
      site
<221> NAME/KEY: misc_feature
<223> OTHER INFORMATION: Isolated oligonucleotide cleavage recognition
      site

<400> SEQUENCE: 21
gactcttcct actcgaaatt taga                                               24

<210> SEQ ID NO 22
```

```
<211> LENGTH: 4
<212> TYPE: PRT
<213> ORGANISM: Unknown
<220> FEATURE:
<223> OTHER INFORMATION: Microsomal retention signal
<221> NAME/KEY: misc_feature
<223> OTHER INFORMATION: Microsomal retention signal

<400> SEQUENCE: 22

Lys Asp Glu Leu
1

<210> SEQ ID NO 23
<211> LENGTH: 21
<212> TYPE: DNA
<213> ORGANISM: Unknown
<220> FEATURE:
<223> OTHER INFORMATION: PCR primer TEV
<221> NAME/KEY: misc_feature
<223> OTHER INFORMATION: PCR primer TEV

<400> SEQUENCE: 23
gcattctact tctattgcag c                                              21

<210> SEQ ID NO 24
<211> LENGTH: 25
<212> TYPE: DNA
<213> ORGANISM: Unknown
<220> FEATURE:
<223> OTHER INFORMATION: Beta-actin forward PCR primer
<221> NAME/KEY: misc_feature
<223> OTHER INFORMATION: Beta-actin forward PCR primer

<400> SEQUENCE: 24
tggaatcctg tggcatccat gaaac                                          25

<210> SEQ ID NO 25
<211> LENGTH: 25
<212> TYPE: DNA
<213> ORGANISM: Unknown
<220> FEATURE:
<223> OTHER INFORMATION: Beta-actin reverse PCR primer
<221> NAME/KEY: misc_feature
<223> OTHER INFORMATION: Beta-actin reverse PCR primer

<400> SEQUENCE: 25
taaaacgcag ctcagtaaca gtccg                                          25

<210> SEQ ID NO 26
<211> LENGTH: 24
<212> TYPE: DNA
<213> ORGANISM: Unknown
<220> FEATURE:
<223> OTHER INFORMATION: IFN-gamma forward PCR primer
<221> NAME/KEY: misc_feature
<223> OTHER INFORMATION: IFN-gamma forward PCR primer

<400> SEQUENCE: 26
tgaacgctac acactgcatc ttgg                                           24

<210> SEQ ID NO 27
<211> LENGTH: 23
<212> TYPE: DNA
<213> ORGANISM: Unknown
<220> FEATURE:
<223> OTHER INFORMATION: INF-gamma reverse PCR primer
<221> NAME/KEY: misc_feature
<223> OTHER INFORMATION: INF-gamma reverse PCR primer
```

<400> SEQUENCE: 27
cgactccttt tccgcttcct gag                23

<210> SEQ ID NO 28
<211> LENGTH: 23
<212> TYPE: DNA
<213> ORGANISM: Unknown
<220> FEATURE:
<223> OTHER INFORMATION: IL-2 forward PCR primer
<221> NAME/KEY: misc_feature
<223> OTHER INFORMATION: IL-2 forward PCR primer

<400> SEQUENCE: 28
atgtacagca tgcagctcgc atc                23

<210> SEQ ID NO 29
<211> LENGTH: 25
<212> TYPE: DNA
<213> ORGANISM: Unknown
<220> FEATURE:
<223> OTHER INFORMATION: IL-2 reverse PCR primer
<221> NAME/KEY: misc_feature
<223> OTHER INFORMATION: IL-2 reverse PCR primer

<400> SEQUENCE: 29
ggctggttga gatgatgctt tgaca              25

<210> SEQ ID NO 30
<211> LENGTH: 24
<212> TYPE: DNA
<213> ORGANISM: Unknown
<220> FEATURE:
<223> OTHER INFORMATION: IL-4 forward PCR primer
<221> NAME/KEY: misc_feature
<223> OTHER INFORMATION: IL-4 forward PCR primer

<400> SEQUENCE: 30
atgggtctca accccaggga agtc               24

<210> SEQ ID NO 31
<211> LENGTH: 24
<212> TYPE: DNA
<213> ORGANISM: Unknown
<220> FEATURE:
<223> OTHER INFORMATION: IL-4 reverse PCR primer
<221> NAME/KEY: misc_feature
<223> OTHER INFORMATION: IL-4 reverse PCR primer

<400> SEQUENCE: 31
gctctttagg ctttccagga agtc               24

<210> SEQ ID NO 32
<211> LENGTH: 25
<212> TYPE: DNA
<213> ORGANISM: Unknown
<220> FEATURE:
<223> OTHER INFORMATION: IL-5 forward PCR primer
<221> NAME/KEY: misc_feature
<223> OTHER INFORMATION: IL-5 forward PCR primer

<400> SEQUENCE: 32
atgactgtgc ctctgtgcct ggagc              25

<210> SEQ ID NO 33
<211> LENGTH: 25
<212> TYPE: DNA
<213> ORGANISM: Unknown

```
<220> FEATURE:
<223> OTHER INFORMATION: IL-5 reverse PCR primer
<221> NAME/KEY: misc_feature
<223> OTHER INFORMATION: IL-5 reverse PCR primer

<400> SEQUENCE: 33 ctgttttcc tggagtaaac tgggg                                        25

<210> SEQ ID NO 34
<211> LENGTH: 25
<212> TYPE: DNA
<213> ORGANISM: Unknown
<220> FEATURE:
<223> OTHER INFORMATION: IL-6 forward PCR primer
<221> NAME/KEY: misc_feature
<223> OTHER INFORMATION: IL-6 forward PCR primer

<400> SEQUENCE: 34 ctgttttcc tggagtaaac tgggg                                        25

<210> SEQ ID NO 35
<211> LENGTH: 25
<212> TYPE: DNA
<213> ORGANISM: Unknown
<220> FEATURE:
<223> OTHER INFORMATION: IL-6 reverse PCR primer
<221> NAME/KEY: misc_feature
<223> OTHER INFORMATION: IL-6 reverse PCR primer

<400> SEQUENCE: 35
tctgaccaca gtgaggaatg tccac                                       25

<210> SEQ ID NO 36
<211> LENGTH: 25
<212> TYPE: DNA
<213> ORGANISM: Unknown
<220> FEATURE:
<223> OTHER INFORMATION: IL-10 forward PCr primer
<221> NAME/KEY: misc_feature
<223> OTHER INFORMATION: IL-10 forward PCr primer

<400> SEQUENCE: 36
acctggtaga agtgatgccc caggc                                       25

<210> SEQ ID NO 37
<211> LENGTH: 22
<212> TYPE: DNA
<213> ORGANISM: Unknown
<220> FEATURE:
<223> OTHER INFORMATION: IL-10 reverse PCR primer
<221> NAME/KEY: misc_feature
<223> OTHER INFORMATION: IL-10 reverse PCR primer

<400> SEQUENCE: 37
ctatgcagtt gaagatgtca aa                                          22

<210> SEQ ID NO 38
<211> LENGTH: 32
<212> TYPE: DNA
<213> ORGANISM: Unknown
<220> FEATURE:
<223> OTHER INFORMATION: TNF-alpha forward PCR primer
<221> NAME/KEY: misc_feature
<223> OTHER INFORMATION: TNF-alpha forward PCR primer

<400> SEQUENCE: 38
ttctgtctac tgaacttcgg ggtgatcggt cc                               32
```

```
<210> SEQ ID NO 39
<211> LENGTH: 32
<212> TYPE: DNA
<213> ORGANISM: Unknown
<220> FEATURE:
<223> OTHER INFORMATION: TNF-alpha reverse PCR primer
<221> NAME/KEY: misc_feature
<223> OTHER INFORMATION: TNF-alpha reverse PCR primer

<400> SEQUENCE: 39
gtatgagata gcaaatcggc tgacggtgtg cc                                    32

<210> SEQ ID NO 40
<211> LENGTH: 226
<212> TYPE: PRT
<213> ORGANISM: Unknown
<220> FEATURE:
<223> OTHER INFORMATION: Plant optimized HBsAg amino acid sequence
<221> NAME/KEY: misc_feature
<223> OTHER INFORMATION: Plant optimized HBsAg amino acid sequence

<400> SEQUENCE: 40
```

Met Glu Asn Thr

-continued

```
<221> NAME/KEY: misc_feature
<223> OTHER INFORMATION: Plant optimized pre-S (pre-S1/S2)  amino acid
      sequence

<400> SEQUENCE: 41

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
            35                  40                  45

Ala Gly Ala Phe Gly Leu Phe Gly Thr Pro Pro His Gly Gly Leu Leu
        50                  55                  60

Gly Trp Ser Pro Gln Ala Gln Gly Ile Leu Gln Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asn Thr His Pro Gln Ala Met Gln Trp Asn
            100                 105                 110

Ser Thr Thr Phe His Gln Thr Leu Gln Lys Pro Arg Val Arg Gly Leu
        115                 120                 125

Tyr Phe Pro Ala Gly Gly Ser Ser Ser Gly Thr Val Asn Pro Val Leu
    130                 135                 140

Thr Thr Ala Ser Pro Leu Ser Ser Ile Phe Ser Arg Ile Gly Asp Pro
145                 150                 155                 160

Ala Leu Asn Met
```

EXPRESSION OF IMMUNOGENIC HEPATITIS B SURFACE ANTIGENS IN TRANSGENIC PLANTS

RELATED APPLICATION

This application claims the benefit of U.S. application Ser. No. 60/113,827 filed Dec. 23, 1998, which is incorporated in its entirety by reference.

TECHNICAL FIELD

The present invention relates to oral vaccines, particularly those provided by edible plants. The invention employs genetic engineering techniques to produce transgenic plants capable of expressing immunogenic polypeptides, including hepatitis B antigen (HBsAg) in quantities sufficient to elicit an immune response in a human or animal that consumes all or a part of the plant.

BACKGROUND OF THE INVENTION

A vaccine for hepatitis B was the first "new generation" recombinant vaccine licensed by the FDA for human use. The immunogenic subunit in this formulation is produced by expressing the gene encoding HBsAg in recombinant yeast; the protein is purified from the genetically engineered yeast and is used for parenteral delivery. In the developed world, the recombinant vaccine has displaced the use of an earlier vaccine derived from the plasma of infected individuals. Both plasma-derived and rHBsAg vaccines are shown to be reasonably safe and effective in high-risk adult populations and newborn infants. However, the cost of the rHBsAg vaccine prevents its extensive availability in developing countries.

The envelope of the hepatitis B virus (HBV) contains three size classes of proteins that share carboxy-terminal sequences. These proteins, called hepatitis B surface antigens (HBsAgs), include large (L, containing a pre-$S_2$ domain), medium ($M_1$ containing a pre-$S_1$ domain), and small (S, containing only the S domain) size classes. All three proteins are found in infectious virions (often referred to as Dane particles) recovered as 42 nm spheres from the serum of infected patients. Serum samples also contain empty spherical particles averaging 22 nm, which contain primarily S class proteins. Mammalian cell lines transfected exclusively with DNA encoding the S protein release 20 nm empty spheres similar to those from infected cells. Moreover, yeast cells transformed with the same gene form analogous spheres, which are found to be equally immunogenic as the 22 nm spheres from infected cells. The yeast-derived material forms the active constituents of the currently available commercial vaccines ENGERIX (SKB) and RECOMBIVAX (Merck).

In mammalian cells, newly synthesized L, M, or S proteins insert into the membrane of the endoplasmic reticulum (ER). The S protein consists of 226 amino acids; its N and C-termini are thought to be on the ER lumen side and it has four transmembrane helices. All three proteins have a glycosylation site at position 146 of the S domain. The three proteins differ in the available sites for and the extent of glycosylation. Improper glycosylation can prevent virion formation, presumably due to misfolding of the proteins. Also, multiple disulfide bonds among cysteines in the proteins are known to be important to the structure of the assembled virion or particles and to the structure of antigenic loops in the protein. Incorrectly assembled particles may interact with cellular chaperones because of the incorrect folding to prevent secretion.

Higher levels of preS1 and preS2 are present in HBV than in 17–25 nm HBsAg particles therefore, immunization with HBsAg particles may not generate high titer antibodies to the preS sequences expressed on HBV. During the course of HBV infection in humans the levels of preS proteins increase during active replication, and anti-preS antibodies and T cells are generated prior to S protein-specific responses. Once anti-HBsAg antibodies rise, anti-preS antibodies decline.

The roles of preS1 and preS2 in virus attachment and neutralization have led to the development of vaccines containing these sequences as well as the entire S region. Vaccines incorporating preS sequences include HEPAGEN (Merck) and BIO-HEP-B (BTG); both are produced in mammalian cell lines. In formulating whole particles that contain S and preS proteins it is important to note that the relative amounts of S, M, and L proteins affect HBsAg assembly, e.g., high levels of L protein reduce the amount of HBsAg particle formation and secretion.

The assembly of the S, M and L surface proteins into particles occurs during budding of the complex into the ER, followed by transport of the particles through the Golgi apparatus to the exterior of the cells. Nanometer scale biological structures, such as viral capsids, assemble through polymerization of similarly folded protein subunits using a small number of well-defined bonding contacts. The driving force for polymerization is the formation of favorable bonding interactions as free subunits are incorporated into the growing polymer. For envelope proteins such as HBsAg, essential steps in the polymerization process are appropriate integration of the polypeptide into the ER membrane followed by establishment of contact among the protein subunits. Normal cellular transport and sorting of proteins in the endomembrane system may contribute to this process.

U.S. Pat. No. 4,710,463 to Murray proposes a method of producing a polypeptide having the antigenicity of a hepatitis B core or surface antigen, which employs a unicellular host. U.S. Pat. No. 5,738,855 to Szu et al. proposes a modified oligosaccharide immunogen similar to the Vi antigen of *Salmonella typhi*, which can be conjugated to a carrier, such as hepatitis B surface antigen. U.S. Pat. No. 4,847,080, EU 0154902 B1, and subsequent papers of Neurath et al. identify peptide epitopes in the preS1 and preS2 regions for both hepatocyte binding and neutralization, as well as peptides that can be included in a vaccine.

Mammals infected by a pathogen mount an immune response when overcoming the invading microorganism by initiating at least one of three branches of the immune system: mucosal, humoral, or cellular immunity. Mucosal immunity largely results from the production of secretory IgA antibodies in secretions that bathe mucosal surfaces in the respiratory tract, the gastrointestinal tract, the genitourinary tract, and the secretory glands. These mucosal antibodies act to limit colonization of the pathogen on mucosal surfaces, thus establishing a first line of defense against invasion. The production of mucosal antibodies can be initiated by local immunization of the secretory gland or tissue or by presentation of the antigen to either the gut-associated lymphoid tissues (GALT; Peyer's Patches) or the bronchial-associated lymphoid tissue (BALT).

Mucosal immunization can be achieved by oral presentation of antigens. Specialized epithelial cells (M cells) overlying organized mucosal lymphoid tissues along the intestinal tract sample the antigens by taking up (by endocytosis) infectious bacteria, viruses, and macromolecules. These are passed to the underlying follicles where immune responses are initiated and cells are dispersed to both mucosal and systemic immune compartments. Epithelial cells are also an integral component of the regulatory cytokine network, including those that are important in the differentiation of B cells.

Oral immunization also induces strong humoral immune responses. Humoral immunity results from the production of circulating antibodies in the serum (especially IgG and IgM), precipitating phagocytosis of invading pathogens, neutralization of viruses, or complement-mediated cytotoxicity against the pathogen. A well-documented relationship exists between HBV protection and the amplitude of the systemic antibody and T cell response to HBsAg proteins, and this protection is likely to be achieved by oral immunization.

In contrast to the large variety of currently available injectable vaccines that provide systemic immunity, vaccines administered non-systemically to stimulate mucosal immunity are rare. Recently, however, there has been a surge of interest in developing novel strategies for vaccine development with oral delivery as the preferred route of delivery. In the design of a successful oral vaccine, two aspects deserve special attention—the use of an appropriate adjuvant and the development of an appropriate antigen delivery system.

Most protein antigens studied for use as adjuvants when administered orally in large doses fail to provoke a mucosal antibody response, but instead induce a state of unresponsiveness or oral tolerance. Cholera toxin (CT) and E. coli heat-labile toxin (LT) are exceptions. The feeding of either CT or LT does not induce tolerance for antibody response and additionally can prevent induction of oral tolerance to unrelated antigens that are administered orally along with the CT or LT (Elson, C. et al., J. Imnmunol. 133:2892–2887 (1984)). These results suggest that CT/LT direct the overall outcome in favor of responsiveness rather than tolerance. In other studies, it is found that CT does not increase the immune response against an antigen that has been previously fed without CT (Xu-Amano, J. Exp. Med. 178:1309–1320 (1993)). This is significant because it indicates that no immune response is mounted against normal dietary antigens in the presence of CT. Generally, two different approaches are taken to induction of tolerance versus immunization following the oral administration of antigen: for the induction of oral tolerance, soluble or aqueous antigen is administered alone; whereas for vaccination protocols, antigens are usually administered in conjunction with mucosal adjuvants.

Recent advances in genetic engineering have provided the tools necessary to transform plants as relatively low-cost candidates for the expression of immunogenic proteins. Both monocotyledonous and dicotyledonous plants have been stably transformed. For instance, tobacco, a dicot, has been transformed with a gene encoding the S protein and the cells can be disrupted to release spheres (or virus-like particles; VLPs) (Mason et al., PNAS USA, 89: 11745–11749 (1992)). When injected into mice, the particles qualitatively mimic the immunogenic properties of the commercial vaccine (Thanavala et al., PNAS USA, 92: 3358–3361 (1995)). This suggests that the process of protein synthesis and assembly may be similar in plant and mammalian cells. Unfortunately, low rates of protein synthesis in the transgenic plants have precluded detailed studies of the formation of the VLPs in vivo.

U.S. Pat. No. 5,679,880 to Curtiss, III proposes a transgenic plant that expresses an antigen or antigenic determinant of a pathogenic microorganism that may elicit a secretory immune response in an animal. U.S. Pat. Nos. 5,484,719 and 5,612,487 to Lam et al. disclose obtaining antigenic particles from transgenic tobacco transformed to express HBsAg. Presently, no method exists to predict the efficiency by which newly synthesized HBsAg proteins will polymerize into antigenic structures in plant cells since the rate-limiting factor(s) are not known. Accordingly, previous studies showing particle formation in transgenic plants may involve non-specific insertion of the newly synthesized protein into various cellular membranes, which could explain the low level of particles accumulating in transgenic plants described to date.

It is desired to develop an inexpensive, safe, and highly effective oral vaccine that elicits systemic, and preferably, mucosal immunity to prevent hepatitis B virus infection. Such a vaccine should be based upon a hepatitis B antigen or primary epitope thereof. An approach that could increase formation of HBsAg virus like particles can employ fusion proteins designed to alter the cellular targeting of the newly synthesized protein subunits. The fusion proteins can have, for instance, a N-terminal leader peptide known to enter the endomembrane system or a C-terminal KDEL (SEQ ID NO:22) extension known to regulate microsomal retention. A particularly satisfactory approach for application in developing countries would be the development of transgenic plants having edible parts that consistently establish oral immunity against HBV when consumed.

SUMMARY OF THE INVENTION

It is an object of the invention to provide plant expression vectors comprising at least two expression cassettes that function to reduce transcriptional silencing of polynucleotide expression. It is another object of the invention to provide novel plant expression vectors for expression of immunogenic polypeptides, including HBsAg. The plant expression vectors can be used to produce immunogenic polypeptides, including HBsAg, in edible plant tissues. It is a further object of the invention to provide such immunogenic polypeptides in edible plant tissue to elicit an immune response in humans and animals when the plant tissues are consumed. These and other objects of the invention are provided by one or more of the embodiments described below.

One embodiment of the invention provides a plant expression vector comprising two expression cassettes. The first cassette comprises a polynucleotide encoding an antigen and the second expression cassette comprises a polynucleotide encoding the same antigen as the polynucleotide of the first expression cassette. The polynucleotide of the second expression cassette is non-identical to the polynucleotide of the first expression cassette. The first cassette can optionally comprise a polynucleotide encoding a hepatitis B surface antigen (HBsAg) and the second expression cassette can comprise a non-identical polynucleotide encoding a HBsAg. Optionally the first expression cassette can comprise a polynucleotide encoding a plant-optimized HBsAg polypeptide, preferably, with at least one plant optimized codon, and wherein the second expression cassette comprises a polynucleotide encoding a native virus-derived HBsAg polypeptide. Even more preferably, the polynucleotide of the first expression cassette comprises SEQ ID NO:3 and the polynucleotide of the second expression cassette comprises SEQ ID NO:1.

Preferably, gene silencing, including RNA-mediated transcriptional gene silencing, is reduced or eliminated when both polynucleotides are expressed in a cell. Optionally, the plant expression vector can have a polynucleotide of the first cassette and a polynucleotide of the second cassette wherein said polynucleotides comprise no more than 90 or no more than 60 contiguous identical nucleotides.

The plant expression vector may further comprise a first expression cassette farther comprising a 5' transcribed, untranslated region and a second expression cassette comprising a non-identical 5' transcribed, untranslated region. The plant expression vector can also comprise a first expression cassette further comprising a 3' transcribed, untranslated region and a second expression cassette comprising a non-identical 3' transcribed, untranslated region. Additionally, the plant expression vector can comprise a first expression cassette further comprising a 5' transcribed, untranslated region and a 3' transcribed, untranslated region. The second expression cassette can comprise a non-identical 5' transcribed, untranslated region and a non-identical 3' transcribed, untranslated region as compared to the first expression cassette. The first expression cassette can comprise a TEV 5' transcribed, untranslated region and a vspB 3' transcribed, untranslated region, and a second expression cassette comprising a TMV 5' transcribed, untranslated region and apin2 3' transcribed, untranslated region. The plant expression vector can additionally comprise a first expression cassette comprising a plant-optimized HBsAg polypeptide and a second expression cassette comprising a native virus-derived HBsAg polypeptide.

In still another embodiment of the invention, an *E. coli* cell is transformed with the plant expression vector described above. Virus like particles can assemble in the cell.

In yet another embodiment of the invention, an Agrobacterium cell is transformed with the plant expression vector described above. Virus like particles can assemble in the cell.

In another embodiment of the invention a plant cell is transformed with the plant expression vector described above. Virus like particles can assemble in the cell. Preferably the plant cell is selected from the group consisting of tomato, potato, banana, and carrot cells. Even more preferably, the plant expression vector is integrated into the nuclear genome of the plant cell.

In even another embodiment of the invention a plant seed comprising the plant expression vector described above is provided.

In still another embodiment of the invention a polynucleotide comprising a nucleic acid sequence encoding a hepatitis B surface antigen (HBsAg) is provided. The polynucleotide is operably linked to a plant functional promoter; a translation enhancement sequence; and a termination sequence. The polynucleotide lacks an untranscribed region between the translation enhancement sequence and the HBsAg encoding sequence. The nucleic acid sequence encoding the HBsAg can comprise at least one altered codon, wherein the altered codon is a plant preferred codon. The plant-functional promoter can be selected from the group consisting of cauliflower mosaic virus (CaMV) 35S, tomato E8, ubiquitin, mannopine synthase, patatin, and granule-bound starch synthase (GBSS) promoters. The promoter may include a dual enhancer region. The translation enhancement sequence can be selected from the group consisting of tobacco etch virus (TEV) and tobacco mosaic virus (TMV) omega translation enhancers. The termination sequence may be selected from the group consisting of a nopaline synthase (nos), a vegetative storage protein (vsp), or a proteinase inhibitor—2 (pin2) termination sequence.

Further the polynucleotide may lack an untranscribed region between the HBsAg encoding sequence and the termination sequence. The polynucleotide can further comprise a nucleic acid sequence encoding a microsomal retention signal operably linked to the 3' end of the HBsAg encoding sequence. The microsomal retention signal can be Ser-Glu-Lys-Asp-Glu-Leu (SEQ ID NO:4). The polynucleotide can lack an untranscribed region between the microsomal retention signal and the termination sequence. The polynucleotide can further comprise a nucleic acid sequence encoding a signal polypeptide operably linked to the 5' end of the HBsAg encoding sequence. The signal peptide can be selected from the group consisting of a vegetative storage protein (VSP) αS signal peptide and a VSP αL signal peptide.

Additionally, the polynucleotide can comprise an HBsAg encoding sequence further comprising a pre-S region. Optionally, the polynucleotide can comprise an HBsAg encoding sequence which comprises the nucleic acid sequence optimized for expression in plants shown in SEQ ID NO:3. The polynucleotide can be selected from the group of polynucleotides consisting of HB104, HB105, HB106, HB107, HB111, HB114, HB115, HB116, HB117, HB118, HB119, HB120, HB121, HB122, HB123, HB131, HB140.3 HB145 and HB165.

In yet another embodiment of the invention an expression vector comprising a polynucleotide described above is provided. The expression vector can comprise a selectable marker, an *E. coli* origin of replication, and/or an *Agrobacterium tumefaciens* origin of replication.

In another embodiment of the invention an *E. coli* cell transformed with the expression vector described above is provided. A virus like particle can assemble in the cell.

In even another embodiment of the invention an Agrobacteriurn cell is transformed with the expression vector described above. A virus like particle can assemble in the cell. The Agrobacterium cell can further comprise a helper Ti plasmid.

In still another embodiment of the invention a transgenic plant cell comprising the polynucleotide, as described above, is provided. A virus like particle can be assembled in the cell. The plant cell can be selected from the group consisting of tomato, potato, banana, and carrot cells. The plant expression vector can be integrated into the nuclear genome of the plant cell.

In yet another embodiment of the invention a plant seed comprises the plant expression vector as described above.

In still another embodiment of the invention an immunogenic composition comprising any of the plant cells described above is provided. The plant cell can be present in plant tissue selected from the group consisting of a fruit, leaf, tuber, plant organ, seed protoplast, and callus. The immunogenic composition can comprise juice or extract of the plant cell. The immunogenic composition can also comprise an adjuvant. The adjuvant can be expressed as a fusion protein with an antigen of the immunogenic composition.

In yet another embodiment of the invention a method of eliciting an immune response in a mammal is provided. The method comprises the step of administering the composition described above to a human or animal. An immune response is elicited. The composition can be administered orally. The administration can comprise consuming the transgenic plant cell. The polypeptide can be administered by a technique selected from the group consisting of intramuscular, oral, intradermal, intraperitoneal, subcutaneous, and intranasal.

Optionally an adjuvant can be administered. The adjuvant can be selected from the group consisting of cholera toxin (CT), E. coli heat labile toxin (LT), anti-idiotypic antibody 2F 10, colonization factor, shiga-like toxin, and intimin. The immune response elicited can be selected from the group of immune responses consisting of humoral; mucosal; cellular; humoral and mucosal; humoral and cellular; mucosal and cellular; and humoral, mucosal and cellular.

In another embodiment of the invention a method of isolating a recombinant HBsAg polypeptide expressed in a plant material is provided. The method comprises subjecting the plant material to a detergent having a concentration of greater than 0.1% and less than 0.5%.

In even another embodiment of the invention a transgenic plant or plant cell is provided. When the transgenic plant or plant cell is consumed as a foodstuff in four or less feedings, it elicits an immune response comprising anti-HBsAg serum antibodies of greater than 50 mIU/mL in a mammal. The immune response can be a primary immune response. The transgenic plant cell can comprise any plant cell described above.

Still another embodiment of the invention provides a transgenic plant or plant cell that, when consumed as a foodstuff in four or less feedings, elicits an anti-HBsAg boosting immune response that increases serum anti-HBsAg antibody levels at least four-fold or to levels greater than 500 mIU/mL in a mammal. The transgenic plant or plant cell can comprise any plant cell described above.

As used herein, an "antigen" is a macromolecule capable of eliciting an immune response in a human or in an animal.

An "epitope" is a portion of an antigen that comprises the particular part of the antigen to which the antibody binds.

A "colonization or virulence antigen" is an antigen of a pathogenic microorganism that is associated with the ability of the microorganism to colonize or invade its host.

A "polynucleotide," "nucleic acid," and the like is a polynucleotide that encodes a polypeptide. The polynucleotide or nucleic acid can include introns, marker genes, signal sequences, regulatory elements, such as promoters, enhancers and termination sequences, and the like.

A first polynucleotide is "non-identical" to a second polynucleotide where at least one nucleotide, and up to and including 85% of overall identity of the first polynucleotide, is different from that of the second polynucleotide.

An "expression vector" is a plasmid, such as pBR322, pUC, or ColE1; a virus such as an adenovirus, Sindbis virus, simian virus 40, alphavirus vectors, and cytomegalovirus and retroviral vectors, such as murine sarcoma virus, mouse mammary tumor virus, Moloney murine leukemia virus, and Rous sarcoma virus. Bacterial vectors, such as Salmonella ssp., Yersinia enterocolitica, Shigella spp., Vibrio cholerae, Mycobacterium strain BCG, and Listeria monocytogenes can be used. Minichromosomes such as MC and MC1, bacteriophages, virus particles, virus-like particles, cosmids (plasmids into which phage lambda cos sites have been inserted) and replicons (genetic elements that are capable of replication under their own control in a cell) can also be used as expression vectors. Preferably, an expression vector is capable of transforming eukaryotic cells, including, for example plant tissue.

A "foodstuff" or "edible plant material" and the like is any plant material that can be directly ingested by animals or human as a nutritional source or dietary complement. An edible plant material includes a plant or any material obtained from a plant, which is suitable for ingestion by mammal or other animals including humans. This term is intended to include raw plant material that may be fed directly to animals or processed plant material that is fed to animals, including humans.

An "immune response" comprises the response of a host to an antigen. A humoral immune response comprises the production of antibodies in response to an antigen or antigens. A cellular immune response includes responses such as a helper T-cell ($CD4^+$) response and a cytotoxic T-cell lymphocyte ($CD8^+$) response. A mucosal immune response (or secretory immune response) comprises the production of secretory (sIgA) antibodies. An immune response can comprise one or a combination of these responses.

An "immunogenic agent" or immunogenic polypeptide" is an antigen or antigens capable of eliciting an immune response. Preferably, the immune response is elicited in a human or animal upon oral ingestion of a eukaryotically expressed antigen. An "immunogenic composition" contains one or more immunogenic agents, optionally in combination with a carrier, adjuvant, or the like.

A "fusion protein" is a protein containing at least 2, 3, 4, 5, 10, or more same or different amino acid sequences linked in a polypeptide where the sequences are not natively expressed as a single protein. Fusion proteins can be produced by well known genetic engineering techniques.

DESCRIPTION OF THE FIGURES

FIG. 1A depicts diagrams of expression cassettes of the present invention. Abbreviations: 35S=35S promoter of cauliflower mosaic virus; GBSS=granule bound starch synthase promoter specific for activity in tubers; TEV=tobacco etch virus, Ω=tobacco mosaic virus omega untranslated leader sequence; NOS=nopaline synthase; VSP=vegetative storage protein; PIN2=proteinase inhibitor 2; TPSS=transit peptide signal sequence for the small sub-unit of rubisco. VSP αS and αL are signal peptides with αL including a putative vacuolar targeting signal. FIG. 1B shows a map of pHB131 and pBB 140.3 with selected restriction endonuclease sites indicated.

FIG. 3 depicts anti-HBsAg antibody responses elicited in mice following oral feeding with HBsAg transgenic potatoes (5 g/mouse) plus 10 μg CT on days 0, 10, 20 and challenged with yeast-derived rHBsAg (Merck, Sharpe & Domme) 0.5 μg i.p. on day 60. A control group received control potato (5 g/mouse) plus the same adjuvant and recombinant challenge on day 60. Both experimental and control groups of mice were fasted overnight prior to feeding the potatoes. Individual mice were monitored to verify consumption of the entire dose. Results are expressed as OD 492:660 nm.

FIG. 5 depicts a plant-optimizes coding sequence for the pre-S (pre-S1/S2) peptide (SEQ ID NO:5) and the corresponding amino acid sequence (SEQ ID NO:41). To obtain the depicted sequence, the wild-type coding sequence for pre-S was examined and one RNA polymerase II termination sequence as well as twelve "CG" potential methylation sites were found, The plant-optimizes sequence contains no cryptic signals and no CG sequences.

FIG. 6 shows a plasmid map of pHB117.

FIG. 7 shows a plasmid map of pHB118.

FIG. 8 shows a plasmid map of pHB119.

FIG. 9 shows a plasmid map of pHB120.

FIG. 10 shows a plasmid map of pHB121.

FIG. 11 shows a plasmid map of pHB122.

FIG. 12 shows a plasmid map pHB123.

FIG. 13 shows a graph demonstrating that sucrose gradients of HB114–16 tubers produce virus like particles.

FIG. 14 shows a western blot of an HB114–6 tuber extract.

FIG. 15 shows a northern blot of HB114–16 tuber and leaf RNA.

FIG. 16 shows a gel of genomic DNA of HV114–16 subjected to PCR, which verifies the presence of the transgene.

FIG. 17 shows a Southern blot of HB114–6 demonstrating at least four insertions of HB114.

FIG. 18 shows a graph demonstrating the stability of HBsAg transformed tubes stored for 9 months.

FIG. 19 shows a western blot analysis of transgenic NT1 cells expressing 3 different forms of HBsAg.

FIG. 20 shows a western blot analysis of transgenic NT1 cells expressing 6 different forms of HBsAg.

FIG. 21 shows synthetic HBsAg constructs of the invention.

FIG. 22 shows a wild-type HBsAg nucleotide sequence (SEQ ID NO:1) and a plant optimized HBsAg nucleotide sequence (SEQ ID NO:3).

FIG. 23 shows a wild-type HBsAg amino acid sequence (SEQ ID NO:2) and a plant-optimized HBsAg amino acid sequence (SEQ ID NO:40).

DETAILED DESCRIPTION OF THE INVENTION

Immunogenic Polypeptides of the Invention

The invention comprises bacterial, viral, and parasitic antigens capable of eliciting an immune response in an animal such as a mouse, rabbit, guinea pig, chicken, goose, duck, chimpanzee, macaque, baboon or a human. Preferably, the immune response is elicited in a mammal.

Viral antigens can be derived from viruses such as Orthomyxoviruses, such as influenza virus (hemagglutinin and nucleoprotein antigens, for example); Retroviruses, such as RSV and SIV, Herpesviruses, such as EBV, CMV, or herpes simplex virus (for example, the thymidine kinase antigen); Lentiviruses, such as HIV(for example, Nef, p24, gp120, gp41, Tat, Rev, and Pol antigens); Rhabdoviruses, such as rabies; Picornoviruses, such as poliovirus; Poxviruses, such as vaccinia; Rotavirus; Parvoviruses and Hepadnaviruses, such as hepatitis B virus (for example, HBsAg).

Bacterial antigens can be derived from, for example, Mycobacterium spp., Helicobacter pylori, Salmonella spp., Shigella spp. (such as the Shigella sonnei form 1 antigen), *E. coli* (such as the CFA/I fimbrial antigen and the heat labile toxin), Rickettsia spp., Listeria spp., *Legionella pneumoniae*, Pseudomonas spp., Vibrio spp. (such as the 0-antigen or cholera toxin), *Borellia burgdorferi, Bordetella pertussis* (such as pertactin and adenylate cyclase-hemolysin), and *Clostridium tetani* (such as the tetnus toxin).

Parasitic antigens can be derived from, for example Plasmodium spp. (for example, circumsporozoite antigens, merozoite surface antigen), Trypanosome spp., Giardia spp., Boophilus spp., Babesia spp., Entamoeba spp. (such as the galactose specific lectin), Eimeria spp., Leishmania spp. (such as gp63), Schistosome spp. (such as triose-phosphate isomerase), Brugia spp. (such as paramyosin), Fascida spp., Dirofilaria spp., Wuchereria spp., and Onchocerea spp.

In a preferred embodiment of the invention an immunogenic polypeptide comprises a hepatitis B surface antigen (HBsAg). The nucleic acid sequence of an HBsAg is shown in SEQ ID NO:1 (FIG. 22) and the amino acid sequence of an HBsAg is shown in SEQ ID NO:2 (FIG. 23). HBsAg epitopes are contained in three HBV-encoded envelope polypeptides and in their respective glycosylated forms. The two smallest polypeptides (24,000 and 27,000 daltons) represent a 226 amino acid polypeptide and the glycosylated form of the same polypeptide. These polypeptides are encoded by the S region of the S open reading frame of HBV. Two other proteins are a 33,000 dalton, 281 amino acid polypeptide comprising 55 amino acids encoded by the pre-S2 region of HBV and 226 amino acids encoded by the S region, and the glycosylated form of the same polypeptide (36,000 daltons). Two other proteins are a 39,000 dalton (389–400 amino acids) polypeptide comprising about 119 amino acids of the pre-S1 region of HBV and sequences encoded by the pre-S2 and S regions, and a glycosylated form of the same polypeptide. All of these proteins are found in infectious virions (often referred to as Dane particles) recovered as 42 nm spheres from the serum of infected patients. Serum samples also contain empty spherical particles averaging 22 nm, which contain primarily S class proteins. Mammalian cell lines transfected exclusively with DNA encoding the S protein release 20 nm empty spheres similar to those from infected cells. Moreover, yeast cells transformed with the same gene form analogous spheres, which are as immunogenic as the 22 nm spheres from infected cells.

The immunogenic polypeptides of the invention comprise at least one epitope that is recognized by an antibody. Epitopes within the polypeptides can be identified by several methods. For example, a polypeptide of the invention can be isolated by methods such as immunoaffinity purification using a monoclonal antibody for the polypeptide. The isolated polypeptide sequence can then be screened. A series of short peptides, which together span the entire polypeptide sequence, can be prepared by proteolytic cleavage. By starting with, for example, 50-mer polypeptide fragments, each fragment can be tested for the presence of epitopes recognized in, for example, an anti-HBsAg enzyme-linked immunosorbent assay (ELISA). Progressively smaller and overlapping fragments can then be tested from an identified 50-mer to map the epitope of interest.

An HBsAg polypeptide of this invention can comprise an S polypeptide and can further comprise a pre-S1 polypeptide. An HBsAg polypeptide of the invention can further comprise a pre-S2 polypeptide. An HBsAg can comprise any combination of S, pre-S1, and pre-S2 polypeptides. Optionally, an HBsAg polypeptide can comprise more than one S, Pre-S1, or pre-S2 polypeptides. The S, Pre-S1, and pre-S2 polypeptides may be derived from the same or different isolates of HBV. Also, S, pre-S1, and pre-S2 polypeptides can be prepared as a fusion protein or as separate polypeptides.

Figure 2A:
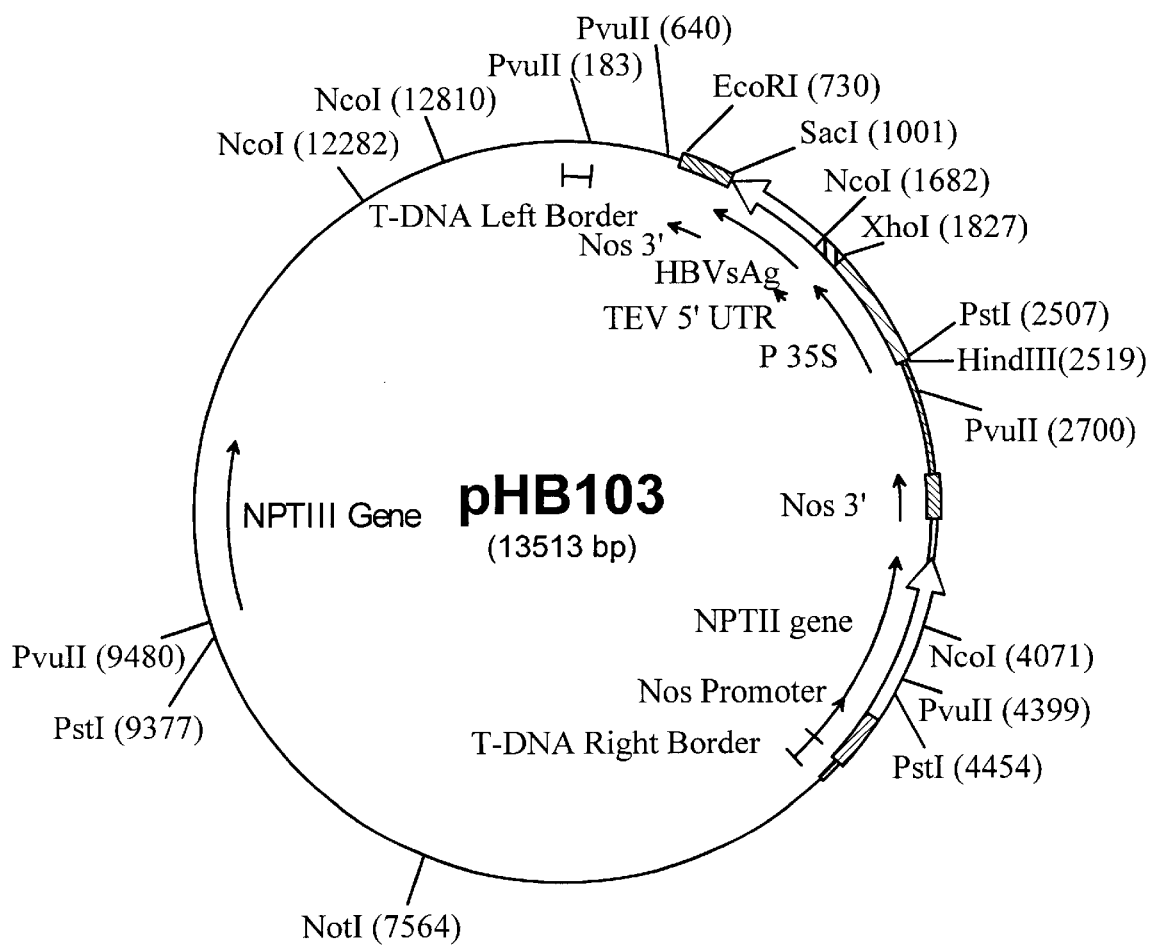
FIG. 2A depicts a restriction map of plasmid pHB103.
Figure 2B:
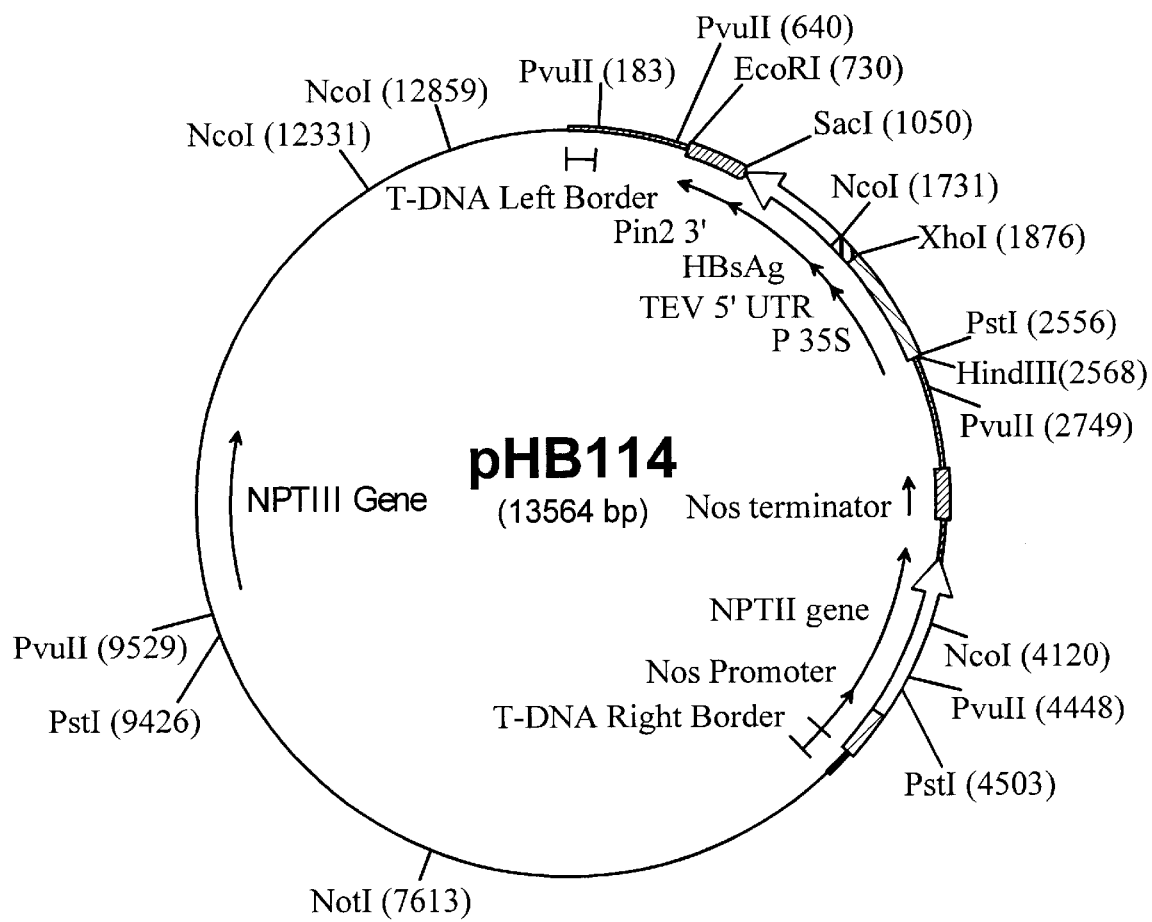
FIG. 2B depicts a restriction map of plasmid pHB114.
Figure 2C:
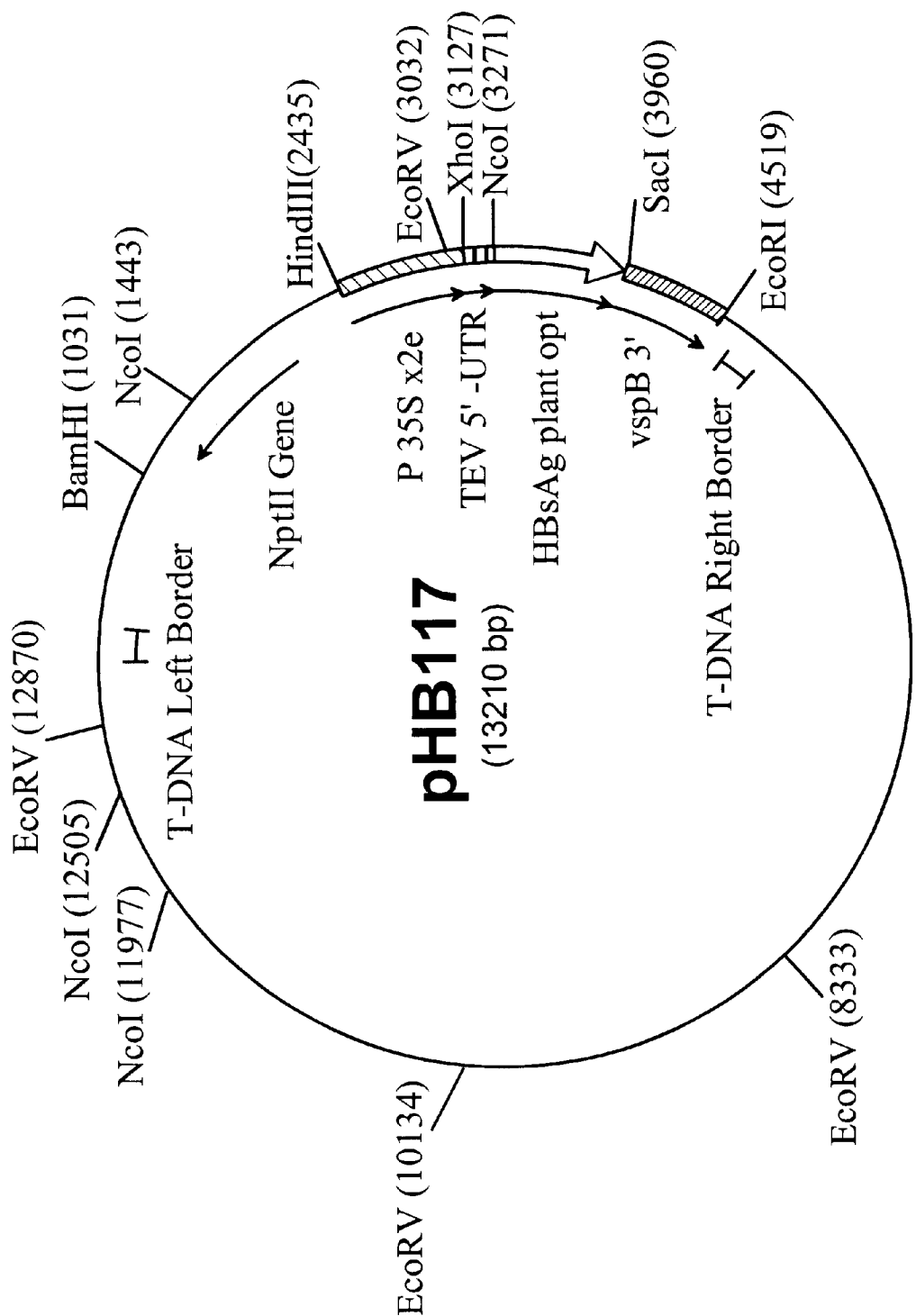
FIG. 2C depicts a restriction map of plasmid pHB117.
Figure 4A:
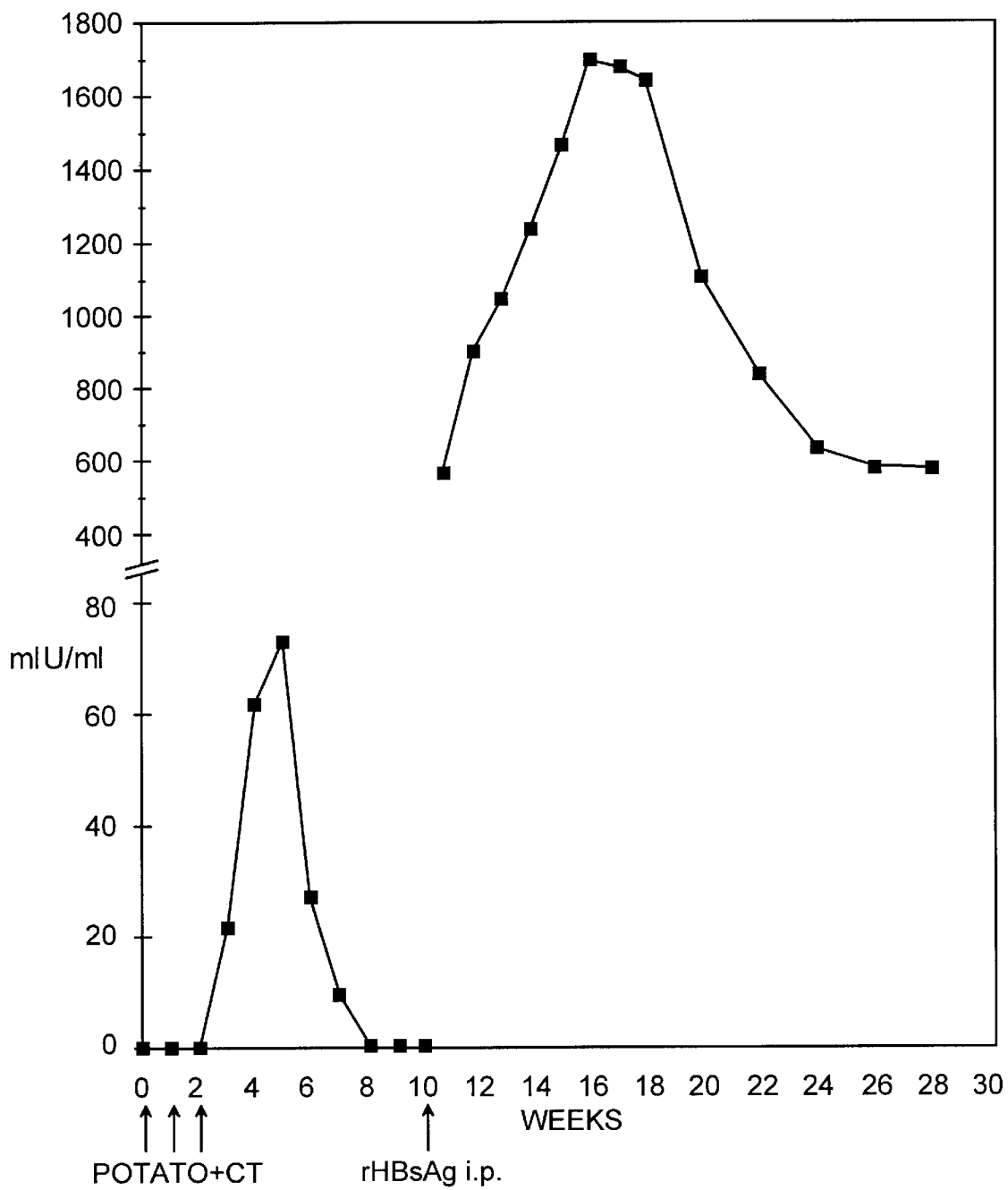
FIGS. 4A–E depict the results of various immunization protocols on mice fed with transgenic potato slices. Feeding Balb/c mice with 5 g recombinant potato coated with 10 μg cholera toxin (CT) three times at weekly intervals gave peak antibody titers of 70–110 mIU/mL, which could be boosted to titers of 1700–3400 mIU/mL by a single sub-immunogenic i.p. dose of HBsAg purified from recombinant yeast (Merck) (actual titers are related to HBsAg expression levels in potato). The level of response was dose-related with potatoes delivering 1.1 μg HBsAg per gram of potato (i.p. dose) (FIG. 4A) giving a lower and less prolonged response than potatoes delivering 8.3 μg/g (s.c. dose) (FIG. 4B). The same feeding regime (8.3 μg/g) was found to boost a single s.c. dose of HBsAg purified from recombinant yeast to give peak antibody titers of 1000 mIU/mL (FIG. 4C). Boiled tubers (5 min, 100° C. gave no detectable immune response (FIG. 4D) but a significant boost was observed on subsequent administration of a single i.p. dose of HBsAg purified from recombinant yeast (FIG. 4E).
Figure 4B:
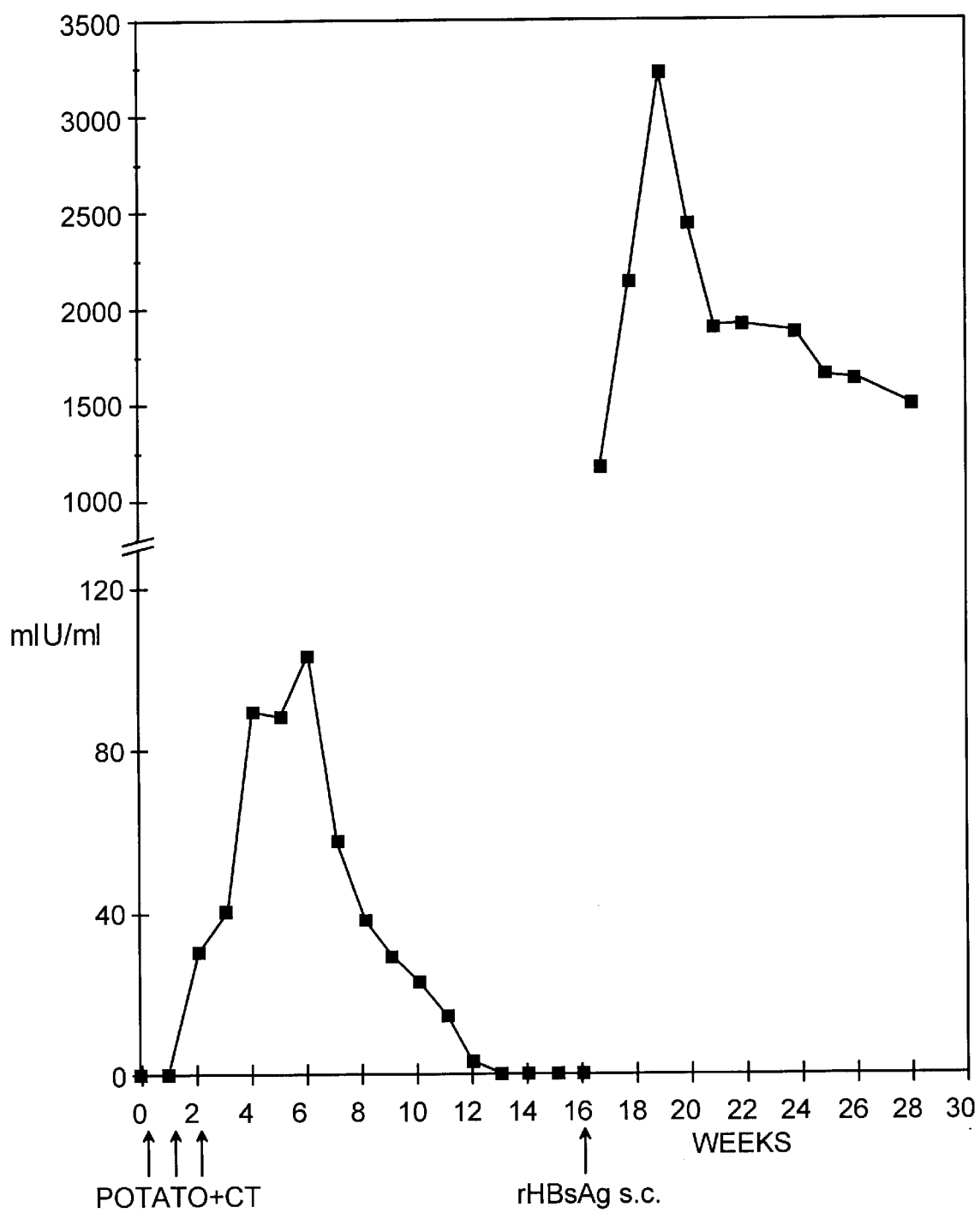
Figure 4C:
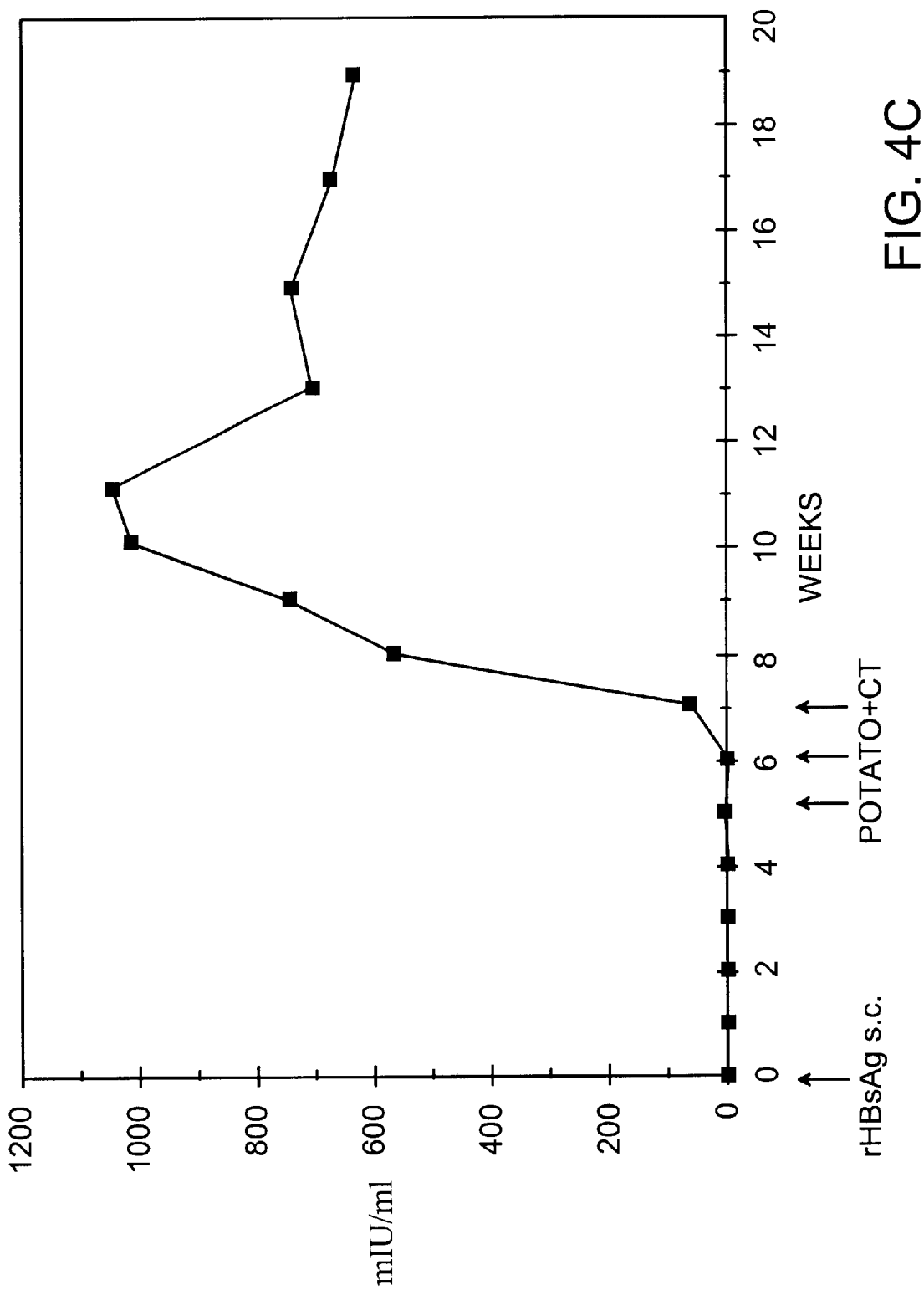
Figure 4D:
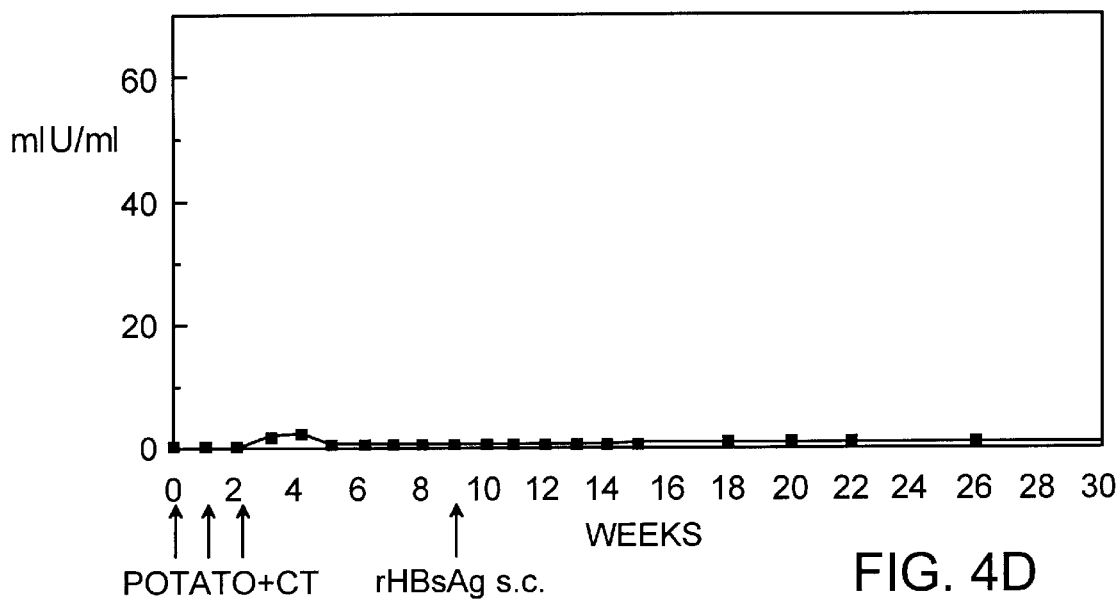
Figure 4E:
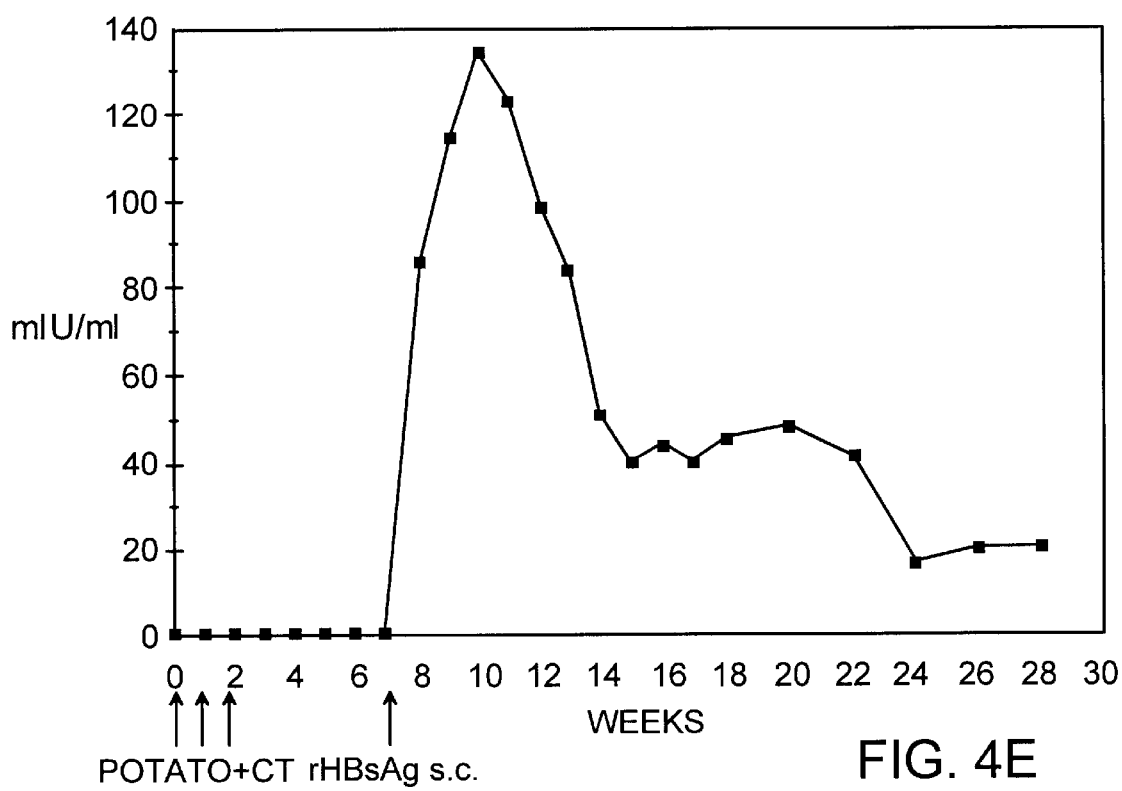

Some epitopes within the pre-S 1 and pre-S2 regions are effective in binding hepatocyte and can be neutralized. Neurath et al. U.S. Pat. No. 4,847,080 and EU-B1-0154902. Pre-S1 sequences spanning residues 1–21, 12–32, 21–47, 27–49, 32–53, 94–117, and 120–153 have be identified as immunogenic. (Neurath et al. 1986). Similarly, pre-S2 sequences spanning residues 120–145 are identified as being immunogenic. Therefore, these residues are useful as immunogenic polypeptides according to the invention. Other peptides involving insertions, deletions, or substitutions of an aforementioned sequence can also be expected to show immunogenicity, and synthesis of such mutants by site-directed mutagenesis is within the skill of the practitioner (Maniatis, T. (1988) *Molecular Cloning: A Laboratory Manual.* Cold Spring Harbor Laboratory). It should be appreciated that to effect immunogenicity it may be necessary to conjugate an epitope to a carrier, such as KLH or a liposome. It is not known precisely how the aforementioned epitopes signal an immune response, however, it is postulated that the IgA receptor, the IL-6 receptor, the asialoglycoprotein receptor, and GAPD may be involved.

A preferred polypeptide of the invention comprises a 15 amino acid peptide, as well as an inclusive 8 residue peptide, which is partially homologous to the group specific "a" determinant of HBsAg. This peptide, which has the sequence AVYYCTRGYHGSSLY (SEQ ID NO:6), reportedly has antigenic properties similar to the group specific "a" determinant, and can duplicate the B and T cell stimulatory activities of anti-idiotypic antibody 2F10 and HBsAg (see, e.g., U.S. Pat. Nos. 5,744,153; 5,531,990; 5,668,253 to Thanavala, Y. et al.). Accordingly, this peptide, and variants thereof, can be an HBsAg immunogenic polypeptide as discussed herein, and a polynucleotide encoding such a peptide is contemplated within the present invention. The polypeptide can serve as an adjuvant itself, similarly to antibody 2F10, when administered with another HBsAg or an immunogenic polypeptide of the invention.

Some of polypeptides of the invention differ from previously obtained polypeptides by virtue of the various leader and retention signals employed to sort the protein. For instance, one such polypeptide comprises an HBsAg amino acid sequence covalently linked to a C-terminal Ser-Glu-Lys-Asp-Glu-Leu sequence (SEQ ID NO:4), with the latter sequence believed to target the protein to the ER. The polypeptides of the present invention in some instances can also differ from previous proteins by virtue of having different glycosylation patterns, which may be a result of their retention time in the ER or the different glycosylation enzymes that may be present in the ER. Accordingly, immunogenic polypeptides obtained can vary somewhat in their immunogenic properties from previous proteins. However, as long as such immunogens share a sufficient number of epitopes with those of the native immunogenic polypeptide, an immune response can be mounted that is sufficiently cross-reactive with the antigen.

Preferably, an HBsAg polypeptide of the invention is capable of forming virus like particles (VLPs). Even more preferably an HBsAg polypeptide of the invention is capable of forming VLPs when produced by a plant cell. In a preferred embodiment of the invention an HBsAg polypeptide is capable of forming cross-linked monomers via disulfide bridges. Highly crosslinked HBsAg can be more stable and more immunogenic. See example 12.

Various strains and isolates of hepatitis and other organisms providing the antigens of the invention occur and polypeptides of any of these strains and isolates can be used in the present invention. Immunogenic polypeptides of the invention, such as HBsAg, can either be full-length polypeptides, fragments of polypeptides, or truncated segments of polypeptides. For example fragments of immunogenic polypeptides can comprise at least 6, 10, 25, 50, 75, 100, 150, 200, 250, 300, or 350, 400, 500, 750, 1000, or 1500 amino acids or more of immunogenic polypeptides. The invention further comprises a mutation or mutations, i.e., amino acid substitutions, additions, deletions, truncations, or combinations thereof, in an immunogenic polypeptide.

An immunogenic polypeptide of the invention can be combined or synthesized with another truncated immunogenic polypeptide, a fragment of another immunogenic polypeptide, or a full-length immunogenic polypeptide. For example a fragment of an immunogenic polypeptide can comprise at least 6, 10, 25, 50, 75, 100, 200, 300, 4000, 500, or 1000 amino acids of an immunogenic polypeptide. The two immunogenic polypeptides may be from the same or different strains. Further, one or more (i.e., 2, 3, 4, 5, 10, 25, or 50) immunogenic polypeptides of the invention, from the same or different strains can be combined.

Preferably, a polypeptide of the invention is produced recombinantly. A polynucleotide encoding a polypeptide of the invention can be introduced into an expression vector which can be expressed in a suitable expression system using techniques well known in the art. A variety of bacterial, yeast, plant, mammalian, and insect expression systems are available in the art and any such expression system can be used. A polypeptide of the invention can be isolated and purified from for example, a eukaryotic cell, such as a plant cell, by methods well known in the art such as immunoaffinity purification. Optionally, a polynucleotide encoding a polypeptide of the invention can be translated in a cell-free translation system.

If desired, a polypeptide of the invention can be produced as a fusion protein, which can also contain other amino acid sequences, such as amino acid linkers or signal sequences, as well as ligands useful in protein purification, such as glutathione-S-transferase, histidine tag, and staphylococcal protein A. Optionally, one or more antigens such as HBsAg, colonization antigens, virulence antigens, and epitopes thereof, and other compositions useful for the stimulation of animmune response in an animal or human can be present in a fusion protein. More than one immunogenic polypeptide, such as HBsAg can be present in a fusion protein. If desired, various combinations of, for example HBsAg polypeptides from different hepatitis strains or isolates can be included in a fusion protein.

Polynucleotides Encoding Immunogenic Polypeptides

Polynucleotides of the invention contain less than an entire bacterial, viral, or protozoan genome and can be single- or double-stranded DNA. Preferably, the polynucleotides are purified free of other components, such as proteins. The polynucleotides encode the immunogenic polypeptides described above. Polynucleotides of the invention can be isolated from a genomic library derived from nucleic acid sequences present in, for example, bacterial, virus, or protozoan cell cultures. Preferably, a polynucleotide is isolated from nucleic acid sequences present in, for example, the plasma, serum, or liver of an HBV infected individual or a cell culture infected with HBV. An amplification method such as PCR can be used to amplify polynucleotides from either bacterial, viral, or protozoan genomic RNA or cDNA encoding an immunogenic polypeptide. The polynucleotides can also be synthesized in the laboratory, for example, using an automatic synthesizer. If desired, the polynucleotides can be cloned into an expression vector and transformed into, for example, bacterial, yeast, insect, plant, or mammalian cells so that the polypeptides of the invention can be expressed in and isolated from cell culture.

The polynucleotides can comprise coding sequences for naturally occurring immunogenic polypeptides or can encode altered immunogenic polypeptides, which do not occur in nature. A mutation or mutations in an immunogenic polynucleotide can be made by site-directed mutagenesis using conventional techniques. A library of mutant polynucleotides comprising single, double, or higher mutations, can also be prepared using random mutagenesis techniques. Mutagenesis techniques are described generally, e.g., in *Current Protocols in Molecular Biology*, Ausubel, F. et al. eds., John Wiley (1998), and random mutagenesis (also referred to as "DNA shuffling") is the subject of U.S. Pat. Nos. 5,605,793, 5,811,238, 5,830,721, 5,834,252, and 5,837,458 to Stemmer et al. A polynucleotide comprising mutations of an immunogenic polypeptide can also be synthesized in a laboratory.

Preferably, an immunogenic polynucleotide of the invention is engineered such that the bacterial codons are systematically replaced by plant-preferred codons. For example, the coding sequence of an HBsAg, or a portion thereof, can be analyzed for its codon usage. This codon usage can then be compared with the frequency of codon usage in abundant proteins found in a particular plant. See, e.g. WO 96/12801. The codons of a polynucleotide which have low or zero frequency of use in a plant can be modified by, for example, site directed mutagenesis or a polynucleotide can be synthesized in the laboratory. The codon modifications are made to conform with the plant codons used in the genes for the abundantly expressed plant proteins. Further, segments of codons with possible poly-A signal sequences can be modified to other codons for the same amino acids. Further, cryptic signal sequences, intron splice sites, and potential methylation sites can be modified. See WO 96/12801; SEQ ID NO:3 (FIG. 22) (showing a nucleic acid sequence encoding HBsAg that has been optimized for expression in plants). The replacement or substitution of plant-preferred codons for the corresponding viral, bacterial, or protozoan-preferred codons can enhance the expression of the immunogenic polynucleotides and can facilitate expression of the encoded polypeptide or polypeptides in a particular part, e.g., the fruit or tuber, of the plant. An immunogenic polynucleotide sequence, such as HBsAg, which has had at least 1, 2, 3, 4, 5, 10, 20, 50, or more codons modified to plant-preferred codons is said to be plant-optimized. Preferably, plant-optimization further comprises modification of codons encoding possible signal sequences, intron splice sites, and methylation sites.

Preferably, a polynucleotide of the invention encoding an immunogenic polypeptide, such as HBsAg, is operably linked to a plant functional promoter. As used herein, "operably linked" refers to the coding sequence for an immunogenic polypeptide, being fused in-frame to a promoter, transcription or translation enhancer, termination sequence, and the like, so that the respective coding sequences are faithfully transcribed and translated. Accordingly, the respective nucleotide sequences need not be contiguously fused, i.e., covalently, to adjoining defined sequences, but may be provided with synthetic adaptors and linkers, and the like, to facilitate assembly of the construct and expression vectors.

A promoter can be a constitutive promoter, whereby expression of an immunogenic polypeptide continually takes place within a cell. Alternatively, a promoter can be inducible, whereby a chemical inducing agent or a tissue-specific agent activates the promoter, such as upon the plant reaching a desired stage of differentiation. Inducible promoters comprise any promoter capable of increasing the amount of polynucleotide product produced by a given polynucleotide in response to exposure to an inducer. Inducible promoters include, but are not limited to a heat shock promoter, a glucocorticoid system, wound inducible, steroid inducible, phosphate deficiency inducible, and any chemically-inducible promoter, including, but not limited to tetracycline, ethylene, copper, salicylic acid, and benz-1,2,3,-thiadiazol. See, e.g., U.S. Pat. Nos. 5,942,662, 5,977,441, 5,684,239, and 5,922,564.

A preferred plant promoter is CaMV 35S containing a dual enhancer region. This promoter is a constitutive promoter and is effective in causing expression in leaves and tubers. Other preferred promoters include patatin, mas, tomato E8 (Giovanni et al., Plant Cell, 1:53–63 (1989)), ubiquitin (Quail et al. U.S. Pat. No. 5,510,474), mannopine synthase (Ellis et al., Mol. Gen. Genet. 195: 466–473 (1984)), nopaline synthase (Ebert et al. PNAS, 84:5745–5749 (1987)), figwort mosaic virus (FMV) (Rogers, U.S. Pat. No. 5,378,619), sucrose synthase (Yang et al. PNAS, 87:4144–4148 (1990)), actin (Wang et al., *Mol. Cell. Biol.*, 12:3399–3406 (1992)), isocitrate lyase (Harada et al. U.S. Pat. No. 5,689,040), and granule-bound starch synthase (GBSS) promoters. Preferably, the promoter includes a dual (or double) enhancer. See Artzen, U.S. Pat. No. 5,914,123; Lam, U.S. Pat. No. 5,612,487; and Maiti, U.S. Pat. No. 5,994,521.

Some exemplary plant functional promoters, which can be used to express a structural gene of the present invention, are among the following: U.S. Pat. No. 5,352,605 and U.S. Pat. No. 5,530,196—CaMV 35S and 19S promoters; U.S. Pat. No. 5,436,393—patatin promoter; U.S. Pat. No. 5,436,393—B33 promoter sequence of a patatin gene derived from Solanum tuberosum, and which leads to a tuber specific expression of sequences fused to the B33 promoter; WO 94/24298—tomato E8 promoter; U.S. Pat. No. 5,556,653—tomato fruit promoters; U.S. Pat. No. 5,614,399 and 5,510,474—plant ubiquitin promoter system; U.S. Pat. No. 5,824,865—5' cis-regulatory elements of abscisic acid-responsive gene expression; U.S. Pat. No. 5,824,857—promoter from badnavirus, rice tungro bacilliform virus (RTBV); U.S. Pat. No. 5,789,214—chemically inducible promoter fragment from the 5' flanking region adjacent the coding region of a tobacco PR-1a gene; U.S. Pat. No. 5,783,394—raspberry drul promoter; WO 98/31812 strawberry promoters and genes; U.S. Pat. No. 5,773,697—napin promoter, phaseolin promoter, and DC3 promoter.; U.S. Pat. No. 5,723,765—LEA promoter; U.S. Pat. No. 5,723,75 7—5' transcriptional regulatory region for sink organ specific expression; U.S. Pat. No. 5,723,751—G-box related sequence motifs, specifically Iwt and PA motifs, which function as cis-elements of promoters, to regulate the expression of heterologous genes in transgenic plants; U.S. Pat. No. 5,633,440—P 119 promoters and their use; U.S. Pat. No. 5,608,144—Group 2 (Gp2) plant promoter sequences; U.S. Pat. No. 5,608,143—nucleic acid promoter fragments derived from several genes from corn, petunia and tobacco; U.S. Pat. No. 5,391,725—promoter sequences from the nuclear gene for chloroplast GS2 glutamine synthetase and from two nuclear genes for cytosolic GS3 glutamine synthetase in the pea plant, *Pisum sativum*; U.S. Pat. No. 5,378,619—full-length transcript promoter from flagwort mosaic virus (FMV); U.S. Pat. No. 5,689,040—isocitrate lyase promoter; U.S. Pat. No. 5,633,438—microspore-specific regulatory element; U.S. Pat. No. 5,595,896—expression of heterologous genes in transgenic plants and plant cells using plant asparagine synthetase promoters; U.S. Pat. No. 4,771,002—promoter region that drives expression of a 1450 base TR transcript in octopine-type crown gall tumors; U.S. Pat. No. 4,962,028—promoter sequences from the gene from the small subunit of ribulose-1,5-bisphosphate carboxylase; U.S. Pat. No. 5,491,288—Arabidopsis histone H4 promoter; U.S. Pat. No. 5,767,363—seed-specific plant promoter; U.S. Pat. No. 5,023,179—21 bp promoter element which is capable of imparting root expression capability to a rbcS-3A promoter, normally a green tissue specific promoter; U.S. Pat. No. 5,792,925—promoters of tissue-preferential transcription of associated DNA sequences in plants, particularly in the roots; U.S. Pat. No. 5,689,053—Brassica sp. polygalacturonase promoter; U.S. Pat. No. 5,824,863—seed coat-specific cryptic promoter region; U.S. Pat. No. 5,689,044—chemically inducible nucleic acid promoter fragment isolated from the tobacco PR-1a gene is inducible by application of a benzo-1,2,3-thiadiazole, an isonicotinic acid compound, or a salicylic acid compound; U.S. Pat. No. 5,654,414—promoter fragment isolated from a cucumber chitinase/lysozyme gene that is inducible by application of benzo-1,2,3-thiadiazole; U.S. Pat. No. 5,824,872—constitutive promoter from tobacco that directs expression in at least ovary, flower, immature embryo, mature embryo, seed, stem, leaf and root tissues; U.S. Pat. No. 5,223,419—alteration of gene expression in plants; U.S. Pat. No. 5,290,924—recombinant promoter for gene expression in momocotyledenous plants; WO 95/21248—method for using TMV to overproduce peptides and proteins; WO 98/05199—nucleic acid comprising shoot meristem-specific promoter and regulated sequence; EP-B-0122791—phaseolin promoter and structural gene; U.S. Pat. No. 5,097,025—plant promoters (sub domain of CaMV 35S); WO 94/24294—use of tomato E8-derived promoters to express heterologous genes, e.g. 5-adenosylmethionine hydrolase in ripening fruit; U.S. Pat. No. 5,801,027—method of using transactivation proteins to control gene expression in transgenic plants; U.S. Pat. No. 5,821,398—DNA molecules encoding inducible plant promoters and tomato Adh2 enzyme; WO 97/47756—synthetic plant core promoter and upstream regulatory element; U.S. Pat. No. 5,684,239 —monocot having dicot wound inducible promoter; U.S. Pat. No. 5,110,732—selective gene expression in plants; U.S. Pat. No. 5,106,739—CaMV 35S enhanced mannopine synthase promoter and method for using the same; U.S. Pat. No. 5,420,034—seed specific transcription regulation; U.S. Pat. No. 5,623,067—seed specific promoter region; U.S. Pat. No. 5,139,954—DNA promoter fragments from wheat; WO 95/14098—chimeric regulatory regions and gene cassettes for use in plants; WO 90/13658—production of gene products to high levels; U.S. Pat. No. 5,670,349—HMG promoter expression system and post harvest production of gene products in plants and plant cell cultures; U.S. Pat. No. 5,712,112—gene expression system comprising the promoter region of the alpha amylase genes in plants.

A preferred polynucleotide comprises a tobacco mosaic virus (TMV) 5' transcribed, untranslated region (UTR) (omega) (Gallie et al. Nucleic Acids Res 20: 4631–4638 (1992)) or a tobacco etch virus (TEV) 5' transcribed, untranslated region (Carrington, et al., J. Virol. 64:1590–1597 (1990)) or fragments thereof, between the promoter and a polynucleotide sequence encoding an immunogenic polypeptide. A TMV 5' UTR facilitates translation of the coding sequence. A polynucleotide may further comprise a TMV 3'-UTR or fragments thereof, which can further facilitate translation. Zeyenko et al., FEBS Lett. 354:271–273 (1994); Leathers et al., Mol. Cell. Biol. 13:5331–5347 (1993); Gallie et al., Nucl. Acids Res. 20:4631–4638 (1992).

Preferably, an expression vector comprises one or more enhancers. Some enhancers that can be used with the present invention are among the following: U.S. Pat. No. 5,424,200 and U.S. Pat. No. 5,196,525—CaMV 35S enhancer sequences; U.S. Pat. No. 5,359,142, U.S. Pat. No. 5,322,938, U.S. Pat. No. 5,164,316, and U.S. Pat. No. 5,424,200—tandemly duplicated CaMV 35S enhancers; WO 87/07664—Ω' region of TMV; WO 98/14604—intron 1 and/or intron 2 of the PAT1 gene.; U.S. 5,593,874-HSP70 introns that when present in a non-translated leader of a chimeric gene enhance expression in plants; U.S. Pat. No. 5,710,267, U.S. Pat. No. 5,573,932, and U.S. Pat. No. 5,837,849—plant enhancer element capable of being bound by an OCS transcription factor; U.S. Pat. No. 5,290,924—a maize Adh1 intron; JP 8256777—translation enhancer sequence.

A polynucleotide of the present invention can also include a transcription termination sequence functional in a plant host. Exemplary termination sequences include nopaline synthase (nos) (Bevan, Nucleic Acids Res., 12: 8711–8721 (1984)), vegetative storage protein (vsp) (Mason et al., Plant Cell. 5:241–251 (1993)) and proteinase inhibitory –2 (pin2) termination sequences (An et al. Plant Cell 1:115–122 (1989)). These sequences are transcribed, but untranslated.

A polynucleotide of the invention can also encode a microsomal retention signal sequence, such as SEKDEL (Ser-Glu-Lys-Asp-Glu-Leu) (SEQ ID NO:4) or KDEL (SEQ ID NO:22), in order to increase retention of the expressed polypeptide in the cell. For example, concentration of HBsAg antigen complex can be obtained by providing the nascent polypeptide with a microsomal retention signal, which signals that the protein is to be recycled to the endoplasmic reticulum (ER) or other organelle. The microsomal retention signal sequence can be operably linked to the 3' end of the immunogenic polypeptide. Preferably, the polynucleotide lacks an untranscribed region between the microsomal retention signal and the termination sequence. The signal can be separated from the immunogenic polypeptide by, for example, a hinge region.

Further, a polynucleotide of the invention can comprise a signal polypeptide operably linked to the 5' end of the immunogenic polypeptide. Signal polypeptides include, for example, a vegetative storage protein (VSP) αS signal peptide or a VSP αL signal peptide. Mason et al., Plant Mol. Biol. 11:845–856 (1988). A signal peptide serves to sort a protein along a predefined pathway, such as to the ER or putative storage vesicles in the cell. A signal peptide thereby permits accumulation and/or further processing of a polypeptide at a targeted site. A signal peptide can be physically separated from an immunogenic polypeptide coding sequence by a hinge region.

In a preferred embodiment, a polynucleotide of the invention comprises a nucleic acid sequence encoding an immunogenic polypeptide, such as HBsAg, operably linked to a plant functional promoter, a translation enhancement sequence, and a termination sequence. Even more preferably, a polynucleotide of the invention lacks an untranscribed region between the translation enhancement sequence and the immunogenic polypeptide encoding sequence. That is, a RNA polymerase that transcribes the translation enhancement sequence does not terminate transcription, but continues on to transcribe the immunogenic polypeptide encoding sequence. Even more preferably, the polynucleotide lacks an untranscribed region between the immunogenic polypeptide sequence and the termination sequence.

Preferably, a polynucleotide of the invention comprises a native virus-derived (or wild-type) HBsAg-encoding nucleotide sequence shown in SEQ ID NO: 1. The corresponding HBsAg amino acid sequence is shown in SEQ ID NO: 2. An HBsAg encoding sequence can be synthesized directly by assembly of synthetic oligomers, or can be derived from a cDNA library, plasmid carrying the sequence, or other vector, such as those discussed hereinbelow.

Alternatively, a polynucleotide of the invention can comprise a synthetic version of the HBsAg encoding sequence, which incorporates one or more insertions, deletions, or mutations designed to improve the efficiency of transformation, transcription, or translation in an eukaryotic expression system, e.g., a plant cell. One such synthetic sequence encoding the HBsAg S protein is shown in SEQ ID NO:3 (FIG. 22); the corresponding amino acid sequence is shown in SEQ ID NO:40 (FIG. 23). Another such sequence adapted for expression in plants, which encodes the preS peptide, is shown in FIG. 5 (SEQ ID NO:5).

Nucleotide sequences having a high degree of homology to these HBsAg sequences are also contemplated. Preferably, the encoded amino acid sequence remains substantially or wholly unchanged. In particular, sequences at least 80%, more preferably 90%, homologous with an HBsAg polynucleotide are contemplated. In the calculation of a percent homology, the percentage of identical base pairs with reference to a polynucleotide is determined, taking into account any occurrence of insertions, deletions, or substitutions in the nucleic acid sequence. Further, the invention contemplates polynucleotides encoding epitopes of an HBsAg polypeptide essential for generating an immune response. Accordingly, C-terminal, N-terminal or any other fragments of the HBsAg protein comprising an epitope are contemplated within the invention. Such fragments can be encoded in a polynucleotide of the invention as a single or repeat sequence. Fragments can be at least 12, 15, 25, 50, 75, 100, 200, 300, 400, 500, 750, or 1000 nucleic acids in length.

Particularly preferred polynucleotides of the invention include those designated herein as HB103, HB104, HB105, HB106, HB107, HB111, HB114, HB115, HB116, HB117, HB118, HB119, HB120, HB121, HB122, HB123, HB145, and HB165, HB131 and HB140.3, which contain various combinations of the structural features mentioned above. The relevant expression cassettes of these plasmids are shown in FIGS. 1A and 1B. Most preferred is construct HB1114, which uses a 35S promoter and a TEV translation enhancer, as well as a proteinase inhibitor 2 (pin2) termination sequence. The kanamycin resistance gene is used as a selectable marker in this plasmid. The vector is derived from a binary vector in *A. tumefaciens*, such as pBIN19 (Bevan 1984) or (pGPTV-KAN) (Becker et al. Plant Mol. Biol. 20:1195–1197(1992)). The 35S promoter is "constitutive" and has a dual enhancer (Mason et al. 1992).

Preferably, the polynucleotide of the invention comprises an expression cassette. That is, the polynucleotide is operably linked to a promoter. Optionally, a translation enhancement sequence, and/or a termination polynucleotide sequence can be included in an expression cassette. Other polynucleotides can also be present in an expression cassette, such as a signal sequences.

In a preferred expression cassette of the invention a polynucleotide encoding a plant optimized or wild-type immunogenic polynucleotide, such as HFBsAg, is operably linked to a plant functional promoter, such as CaMV 35S or tomato E8. Further, a cassette can comprise a tobacco etch virus (TEV) or tobacco mosaic virus (TMV) omega translation enhancer, which is transcribed, but untranslated. A cassette can also comprise a 3' transcribed, untranslated region such as nopaline synthase (nos), a vegetative storage protein (vsp), or a proteinase inhibitor such as pin2. An expression cassette can lack an untranscribed region between the translation enhancement sequence and the immunogenic polypeptide encoding sequence and/or between the 3' transcribed, untranslated region. (Mason, 1992).

Expression cassettes of the invention can be designed to comprise promoters that direct polypeptide expression in particular parts of the plant. For example, expression cassettes including the CaMV 35S promoter and a polynucleotide of the invention can be used to constitutively transform plants so that a polypeptide expressed by a polynucleotide of the invention is produced in the leaves of the plant. This allows for rapid analysis of polynucleotide expression and biochemical characterization of polynucleotide products.

Expression cassettes comprising a 2S albumin promoter and a polynucleotide of the invention can be used to cause seed-specific polynucleotide expression to create the production of a polypeptide of the invention in seed tissues, for example canola (*Brassica napus*) seeds.

Expression cassettes comprising a patatin promoter or a soybean vspB promoter and a polynucleotide of the invention can be used to cause tuber-specific polynucleotide expression and tuber specific production of a polypeptide in tuber tissues such as potato (*Solanum tuberosum*).

Expression cassettes comprising fruit ripening specific promoters and polynucleotides of the invention can be used to transform plants that produce a polypeptide of the invention in ripened fruit, such as banana (*Musa acuminata*).

Expression Vectors

If desired, a polynucleotide or an expression cassette comprising polynucleotides of the invention can be cloned into an expression vector and transformed into, for example, bacterial, yeast, insect, plant, or mammalian cells so that the polypeptides of the invention can be expressed in and isolated from cell culture. The polynucleotides can be contained within a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, and cytomegalovirus and retroviral vectors, such as murine sarcoma virus, mouse mammary tumor virus, Moloney murine leukemia virus, and Rous sarcoma virus. Bacterial vectors, such as Salmonella ssp., *Yersinia enterocolitica*, Shigella spp., *Vibrio cholerae*, Mycobacterium strain BCG, *Listeria monocytogenes*, and Agrobacterium spp. can be used. Minichromosomes such as MC and MC1, bacteriophages, virus particles, virus-like particles, cosmids (plasmids into which phage lambda cos sites have been inserted) and replicons (genetic elements that are capable of replication under their own control in a cell) can also be used.

Preferably, an expression vector comprises a selectable marker in addition to a polynucleotide of the invention. Examples of selectable markers include a kanamycin gene, a β-glucuronidase gene, a neomycin transferase gene, a tfdA gene, a Pat gene, a hyg gene, a methotrexate-resistant DHFR gene, a dehalogenase gene, and a bar gene. An expression vector can also comprise an *E. coli* origin of replication, for example the Co1E1 or pBR322 origin of replication, to facilitate replication of the vector in *E. coli*. An expression vector of the invention can also comprise an *A. tumefaciens* origin of replication, to permit replication of the vector therein, such as when *A. tumefaciens* is to be used for plant transformation.

Gene silencing can affect the level of expression of a polynucleotide of the invention. There are two different kinds of gene silencing: transcriptional gene silencing (TGS) and post-transcriptional gene silencing (TPGS). Vaucheret et al. Plant J. 16:651–9. One type of TGS is cis-inactivation in which a DNA locus that is methylated affects the DNA connected to it. In plants, methylation may spread from adjacent sequences into transgenes and cause gene silencing. Prols and Meyer, Plant J. 2:463–75 (1992). A plant optimized sequence will have a reduced number of sites or no sites upon which methylation can occur, therefore, this type of gene silencing may be minimized by use of a plant optimized sequence for the transgenic protein. Another type of cis-inactivation occurs with multiple copies of the same nucleotide sequence integrated at one locus. Again, the mechanism of silencing seems to involve methylation (Ye and Signer, PNAS USA 93:10881–6 (1996). A plant optimized sequence without potential methylation sites may avoid this type of silencing.

Post-transcriptional gene silencing can occur when transgene RNA is produced at high levels. If more than one copy of a transgene is producing RNA, then RNA may accumulate to a threshold level that will stimulate post-transcriptional gene silencing (Vaucheret et al. Plant J. 16:651–9 (1998). Some studies suggest that as little as 60 bp of sequence identity within the transcribed region can mediate this process. Depicker & Van Mantagu, Curr. Opin. Cell. Biol. 9:373–82 (1997). Combining non-identical copies of a coding sequence in a transgenic plant can thus increase levels of mRNA that encode the same polypeptide without stimulation of the RNA-mediated silencing process.

In a preferred embodiment, an expression vector comprises two expression cassettes. The first expression cassette can comprise a polynucleotide encoding an immunogenic polypeptide (or antigen). The second expression cassette can comprise a non-identical polynucleotide encoding the same immunogenic polypeptide. For example, the first expression cassette can comprise a polynucleotide encoding HBsAg wherein the polynucleotide has been plant-optimized. See, e.g., SEQ ID NO:3 (FIG. 22). The second expression cassette can then comprise a polynucleotide encoding a native virus-derived (wild-type) HBsAg. An expression vector comprising two or more expression cassettes encoding the same immunogenic polypeptide will increase the production of the immunogenic polypeptide by increasing the copy number. However, sequence duplication from multiple copies or an identical sequence can lead to undesirable post-transcriptional gene silencing. Depicker & Van Montagu, Curr. Opin. Cell Biol. 9:373–82 (1997); Vaucheret et al., Plant J. 16:651–9 (1998). Therefore, it is an object of the invention to reduce or eliminate transcriptional gene silencing, such as RNA-mediated post-transcriptional gene silencing, by providing two or more expression cassettes in an expression vector that each comprise non-identical polynucleotides encoding the same immunogenic polypeptide. Preferably, the cassettes comprise further minimal sequence identity by the use of different or non-identical promoters, and 5' and 3' transcribed, untranslated regions, such as translation enhancement sequences and termination sequences. The expression cassettes can further comprise different polynucleotides encoding, for example, signal peptides.

Preferably, each expression cassette combined into one plant expression vector shares no length of sequence identity with another expression cassette that is greater than 90 base pairs, and more preferably no length of sequence identity with another expression cassette that is greater than 60 base pairs, and most preferably no length of sequence identity with another expression cassette that is greater than 30 base pairs. That is, no greater than 90 base pairs (or 60 base pairs, or 30 base pairs) are identical within any length of the expression cassette, when each component of one expression cassette (i.e., nucleic acids encoding a promoter, immunogenic polypeptide, 5' and 3' transcribed, untranslated regions, and any other components) is compared to each component of a second expression cassette.

A difference in transcriptional gene silencing can be measured by construction of a plant expression vector comprising for example, two identical expression cassettes each comprising a polynucleotide encoding an immunogenic polypeptide of interest. The amount of expression of this immunogenic polypeptide in a plant cell can be compared to the amount of expression of the immunogenic polypeptide when it is expressed by a plant expression vector comprising for example, two non-identical expression cassettes encoding the polypeptide of interest. A greater amount of the immunogenic polypeptide expressed by the plant expression vector comprising two non-identical expression cassettes indicates that post-transcriptional gene silencing has been reduced or has not been activated in the plant cell. Preferably, transcriptional gene silencing is reduced by at least 10, 25, 50, 75, or 100%.

Further, each expression cassette in a plant expression vector may comprise the same or different promoters, translation enhancement sequences, and termination sequences. Each expression cassette can also comprise other polynucleotide sequences encoding, for example, a signal sequence. Preferably, when two or more expression cassettes are used in one plant expression vector, each expression cassette comprises a non-identical immunogenic polypeptide, a non-identical or different translation enhancement sequence, and a non-identical or different termination sequence.

In another preferred embodiment, separate non-identical expression vectors that each contain an expression cassette for the same polypeptide (or antigen) can be used to transform a plant sequentially. Further, two transgenic plants that harbor non-identical expression cassettes for the same polypeptide (or antigen) can be sexually crossed to combine the two expression cassettes within the genomes of selected progeny. Similarly, breeding of different progeny lines, each containing multiple non-identical expression cassettes for the same polypeptide (or antigen) can yield even greater numbers of non-identical expression cassettes within the genome of the same individual plant. Thus the multiple expression cassettes need not be present on the same expression vector, but can be introduced separately by either sequential transformation or by sexual crossing.

Preferably, a plant expression vector of the invention comprises at least 2, 3, 4, 5, 10, or more expression cassettes. Each expression cassette can comprise the same polynucleotides or different polynucleotides.

Transformation and Regeneration of Plants with Polynucleotides and Expression Vectors A further aspect of the present invention is a eukaryotic or prokaryotic cell that comprises, e.g., is transformed with, a polynucleotide of the invention or a expression cassette comprising a polynucleotide of the invention. Preferably, the cell is a plant cell, but other types of cells, such as insect, mammalian, and bacterial cells are contemplated. Whenever a plant cell is employed, it is preferred that the polynucleotide is integrated into the nuclear genome of the plant cell to ensure its stability and passage into the germline. A polynucleotide of the invention can also in some cases be maintained outside the chromosome, such as in the mitochondrion, chloroplast or cytoplasm. A preferred mode of transfer of a polynucleotide to an insect cell is via viral transport, where replication can be maintained extrachromosomally or by integration. Methods of transfer of polynucleotides into mammalian and bacterial cells are well known in the art.

A transformed plant cell is preferably one from a plant that can be consumed as a foodstuff or that expresses the desired protein or polypeptide in a readily isolateable form. Representative plants include tobacco, banana, tomato, potato, carrot, soybean, corn, rice, wheat, and sunflower. Particularly preferred potato hosts include varieties "Desiree" and FL 1607 ("Frito Lay 1607"), which can be obtained from Frito-Lay, Inc., Rhinelander, Wis. A preferred tomato line, TA234, can be obtained from Steven Tanksley, Dept. of Plant Breeding, Cornell University, Ithaca, N.Y. 14853. A transgenic plant seed transformed with a polynucleotide of the invention, which is obtained by propagation of a transgenic plant, is yet a further aspect of the invention.

Among the principal methods for effecting transfer of foreign nucleic acid constructs into plants is the *A. tumefaciens* transformation technique. This method is based upon the etiologic agent of crown gall, which afflicts a wide range of dicotyledons and gymnosperms. Where the target plant host is susceptible to infection, the *A. tumefaciens* system provides high rates of transformation and predictable chromosome integration patterns.

Agrobacterium, which normally infects a plant at wound sites, carries a large extrachromosomal element called Ti (tumor inducing) plasmid. Ti plasmids contain two regions required for tumor induction. One region is the T-DNA (transferred DNA), which is the DNA sequence that is ultimately stably transferred to plant genomic DNA. The other region is the vir (virulence) region, which has been implicated in the transfer mechanism. Although the vir region is required for stable transformation, the vir region DNA is not transferred to the infected plant. Transformation of plant cells mediated by infection with Agrobacterium and subsequent transfer of the T-DNA have been well documented. Bevan et al., Int. Rev. Genet. 16:357 (1982). The Agrobacterium system is well developed and permits routine transformation of DNA into the plant genome of a variety of plant tissues. For example, tobacco, tomato, sunflower, cotton, rapeseed, potato, poplar, and soybean can be transformed with the Agrobacterium system.

Preferably, where *A. tumefaciens*-mediated transformation of plants with a polynucleotide of the invention is used, flanking T-DNA border regions of *A. tumefaciens* are provided. T-DNA border regions are 23–25 base pair direct repeats involved in the transfer of T-DNA to the plant genome. The flanking T-DNA border regions bracket the T-DNA and signal the polynucleotide that is to be transferred and integrated into the plant genome. Preferably, a polynucleotide or expression vector of the invention comprises at least one T-DNA border, particularly the right T-DNA border. Optionally, a polynucleotide to be delivered to a plant genome is sandwiched between the left and right T-DNA borders. The borders may be obtained from any Ti or Ri (see below) plasmid and may be joined to an expression vector or polynucleotide by any conventional means.

Typically, a vector containing the polynucleotide to be transferred is first constructed and replicated in *E. coli*. This vector contains at least one right T-DNA border region, and preferably a left and right border region flanking the desired polynucleotide. A selectable marker (such as a gene encoding resistance to an antibiotic such as kanamycin) can also be present to permit ready selection of transformed cells. The *E. coli* vector is next transferred to Agrobacterium, which can be accomplished via a conjugation mating system or by direct uptake. Once inside the Agrobacterium, the vector containing the polynucleotide can undergo homologous recombination with a Ti plasmid of the Agrobacterium to incorporate the T-DNA into a Ti plasmid. A Ti plasmid contains a set of inducible vir genes that effect transfer of the T-DNA to plant cells.

Alternatively, the vector comprising the polynucleotide can be subjected in trans to the vir genes of the Ti plasmids. In a preferred aspect, a Ti plasmid of a given strain is "disarmed," whereby the onc genes of the T-DNA is eliminated or suppressed to avoid formation of tumors in the transformed plant, but the vir genes provided in trans still effect transfer of T-DNA to the plant host. See, e.g., Hood, Transgenic Res. 2: 208–218 (1993); Simpson, Plant Mol. Biol. 6: 403–415 (1986). For example, in a binary vector system, an *E. coli* plasmid vector is constructed comprising a polynucleotide of interest flanked by T-DNA border regions and a selectable marker. The plasmid vector is transformed into *E. coli* and the transformed *E. coli* is then mated to Agrobacterium by conjugation. The recipient Agrobacterium contains a second Ti plasmid (helper Ti plasmid) that contains vir genes, but has been modified by removal of its T-DNA fragment. The helper Ti plasmid will supply proteins necessary for plant cell infection, but only the *E. coli* modified T-DNA plasmid will be transferred to the plant cell.

The *A. tumefaciens* system permits routine transformation of a variety of plant tissues. See, e.g., Chilton, Scientific American 248:50 (1983); Gelvin, Plant Physiol. 92: 281–285 (1990); Hooykaas, Plant Mol Biol. 13: 327–336 (1992); Rogers et al., Science 227: 1229–1231 (1985). Representative plants that have been transformed with this system and representative references are listed in Table 1. Other plants having edible parts, or which can be processed to afford isolated protein, can be transformed by the same methods or routine modifications thereof.

TABLE 1

| Plant | Reference |
|---|---|
| Tobacco | Barton, K. et al., (1983) Cell 32, 1033 |
| Tomato | Fillatti, J. et al., (1987) Bio/Technology 5, 726–730 |
| Potato | Hoekema, A. et al., (1989) Bio/Technology 7: 273–278 |
| Eggplant | Filipponee, E. et al., (1989) Plant Cell Rep. 8: 370–373 |
| Pepino | Atkinson, R. et al., (1991) Plant Cell Rep. 10: 208–212 |
| Yam | Shafer, W. et al., (1987) Nature. 327: 529–532 |
| Soybean | Delzer, B., et al., (1990) Crop Sci. 30: 320–322 |
| Pea | Hobbs, S. et al., (1989) Plant Cell Rep. 8: 274–277 |
| Sugar beet | Kallerhoff, J. et al., (1990) Plant Cell Rep. 9: 224–228 |
| Lettuce | Michelmore, R., et al., (1987) Plant Cell Rep. 6: 439–442 |

TABLE 1-continued

| Plant | Reference |
| --- | --- |
| Bell pepper | Liu, W. et al., (1990) Plant Cell Rep. 9: 360–364 |
| Celery | Liu, C-N. et al., (1992) Plant Mol. Biol. 1071–1087 |
| Carrot | Liu, C-N. et al., (1992) Plant Mol. Biol. 1071–1087 |
| Asparagus | Delbriel, B. et al., (1993) Plant Cell Rep. 12: 129–132 |
| Onion | Dommisse, E. et al., (1990) Plant Sci. 69: 249–257 |
| Grapevine | Baribault, T., et al., (1989) Plant Cell Rep. 8: 137–140 |
| Muskmelon | Fang, G., et al., (1990) Plant Cell Rep. 9: 160–164 |
| Strawberry | Nehra, N. et al., (1990) Plant Cell Rep. 9: 10–13 |
| Rice | Raineri, D. et al., (1990) Bio/Technology. 8: 33–38 |
| Sunflower | Schrammeijer, B. et al., (1990) Plant Cell Rep. 9: 55–60 |
| Rapeseed/ Canola | Pua, E. et al., (1987) Bio/Technology 5. 815 |
| Wheat | Mooney, P. et al., (1991) Plant Cell Tiss. Organ Cult. 25: 209–218 |
| Oats | Donson, J. et al., (1988) Virology. 162: 248–250 |
| Maize | Gould, J. et al., (1991) Plant Physiol. 95: 426–434 |
| Alfalfa | Chabaud, M. et al., (1988) Plant Cell Rep. 7: 512–516 |
| Cotton | Umbeck, P. et al., (1987) Bio/Technology. 5: 263–266 |
| Walnut | McGranahan, G. et al., (1990) Plant Cell Rep. 8: 512–516 |
| Spruce/ Conifer | Ellis, D. et al., (1989) Plant Cell Rep. 8: 16–20 |
| Poplar | Pythoud, F. et al., (1987) Bio/Technology 5: 1323 |
| Apple | James, D. et al., (1989) Plant Cell Rep. 7: 658–661 |

Other Agrobacterium strains such as *A. rhizogenes* can be used as a vector for plant transformation. *A. rhizogenes*, which incites root hair formation in many dicotyledonous plant species, carries a large extra-chromosomal element called a Ri (root-including) plasmid, which functions in a manner analogous to the Ti plasmid of *A. tumefaciens*. Transformation using *A. rhizogenes* has developed analogously to that of *A. tumefaciens* and has been used successfully, e.g., to transform alfalfa and poplar. Sukhapinda et al., Plant Mol. BioL 8:209 (1987).

Methods of inoculation of the plant tissue vary depending upon the plant species and the Agrobacterium delivery system. A convenient approach is the leaf disc procedure which can be performed with any tissue explant that provides a good source for initiation of whole plant differentiation. The addition of nurse tissue may be desirable under certain conditions. Other procedures such as in vitro transformation of regenerating protoplasts with *A. tumefaciens* may be followed to obtain transformed plant cells as well.

Direct gene transfer procedures can be used to transform plants and plant tissues without the use of Agrobacterium plasmids. Potrykus, Bio/Technology. 8:535–542 (1990); Smith et al. Crop Sci., 35: 01–309 (1995). Direct transformation involves the uptake of exogenous genetic material into plant cells or protoplasts. Such uptake can be enhanced by use of chemical agents or electric fields. For example, a polynucleotide of the invention can be transformed into protoplasts of a plant by treatment of the protoplasts with an electric pulse using electroporation. For electroporation, the protoplasts are isolated and suspended in a mannitol solution. Supercoiled or circular plasmid DNA comprising a polynucleotide of the invention is added. The solution is mixed and subjected to a pulse of about 400 V/cm at room temperature for about 10 to 100 microseconds. A reversible physical breakdown of the membrane occurs such that the foreign genetic material is transferred into the protoplasts. The foreign genetic material can then be integrated into the nuclear genome. Several monocot protoplasts have also been transformed by this procedure including rice and maize.

Liposome fusion is also an effective method for transformation of plant cells. In this method, protoplasts are brought together with liposomes carrying a polynucleotide of the invention. As the membranes merge, the foreign gene is transferred to the protoplasts. Dehayes et al., EMBO J. 4:2731 (1985). Similarly, direct gene transfer using polyethylene glycol (PEG) mediated transformation has been carried out in *N. tabacum* (a dicot) and *Lolium multiflorum* (a monocot). Direct gene transfer is effected by the synergistic interaction between $Mg^{+2}$, PEG, and possibly $Ca^{+2}$. Negrutiu et al., Plant Mol. Biol. 8: 363 (1987). Alternatively, exogenous DNA can be introduced into cells or protoplasts by microinjection of a solution of plasmid DNA comprising a polynucleotide of the invention directly into the cell with a finely pulled glass needle.

Direct gene transfer can also be accomplished by particle bombardment (or microparticle acceleration), which involves bombardment of plant cells by microprojectiles carrying a polynucleotide of the invention. Klein et al., Nature 327:70 (1987); Sanford, Physiol. Plant. 79: 206–209 (1990). In this procedure, chemically inert metal particles, such as tungsten or gold, are coated with a polynucleotide of the invention and accelerated toward the target plant cells. The particles penetrate the cells, carrying with them the coated polynucleotide. Microparticle acceleration has been shown to lead to both transient expression and stable expression in cells suspended in cultures, protoplasts, and immature embryos of plants, including onion, maize, soybean, and tobacco. McCabe et al., Bio/Technology. 6: 923 (1988).

Additionally, DNA viruses can be used as gene vectors in plants. For example, a cauliflower mosaic virus carrying a modified bacterial methotrexate-resistance gene has been used to infect a plant. The foreign gene systematically spreads throughout the plant. Brisson et al., Nature 310:511 (1984). The advantages of this system are the ease of infection, systemic spread within the plant, and multiple copies of the gene per cell.

Once plant cells have been transformed, there are a variety of methods for regenerating plants. The particular method of regeneration will depend on the starting plant tissue and the particular plant species to be regenerated. Many plants can be regenerated from callus tissue derived from plant explants, including, but not limited to corn, rice, barley, wheat, rye, sunflower, soybean, cotton, rapeseed, and tobacco. Regeneration of plants from tissue transformed with *A. tumefaciens* has been demonstrated in plants including, but not limited to sunflower, tomato, white clover, rapeseed, cotton, tobacco, potato, maize, rice, and numerous vegetable crops. Plant regeneration from protoplasts is a particularly useful technique and has been demonstrated in plants including, but not limited to tobacco, potato, poplar, corn, and soybean. Evans et al., *Handbook of Plant Cell Culture* 1, 124 (1983).

Preliminary studies of transformation protocols, and the like, can be explored through the use of a reporter gene to gauge the efficiency of expression afforded by a given construct. Exemplary reporter genes encode β-glucuronidase (GUS), chloramphenicol acetyl transferase, β-galactosidase, green fluorescent protein, and luciferase. Plant cells transformed with a reporter gene or polynucleotide of the present invention can be assayed for levels of expression in a number of ways. For instance, standard Southern or Northern blotting, PCR, and immunoassay techniques can be performed on selected plant tissues.

Plants Expressing the Immunogenic Polypeptides of the Invention

The invention includes whole plants, plant cells, plant organs, plant tissues, plant seeds, protoplasts, callus, cell cultures, and any group of plant cells organized into structural and/or functional units capable of expressing at least a polynucleotide of the invention. Preferably, whole plants, plant cells, plant organs, plant tissues, plant seeds, protoplasts, callus, cell cultures, and any group of plant cells produce at least 0.001, 0.01, 1, 5, 10, 25, 50, 100, 500, or 1000 µg of polypeptide of the invention per gram of total soluble plant material. Preferably, a plant used in accordance with the invention should contain at least 5 µg and preferably from about 7 µg to 5 about 15 µg of HBsAg per gram of plant material to be ingested. The animal, e.g. a human, will usually ingest sufficient plant material to provide from about 2 to about 5 grams of plant material per kilogram of body weight. The invention further comprises immunogenic polypeptides of the invention, such as HBsAg, isolated, purified, or partially purified from the plant cells, or plant tissue in which they were produced.

Extracts of plant tissue can be assayed for expression of immunogenic polypeptides by ELISA. Briefly, an antibody in buffer to the immunogenic polypeptide can be coated on, using various techniques, for example, polystyrene ELISA plates. After an approximately 1 hour incubation at room temperature the buffer is washed off with for example, PBS and the wells blocked for non-specific binding with 5% milk in PBS. Plant extract samples to be assayed are loaded into the wells. To obtain a standard curve for quantification of the immunogenic polypeptides different dilutions of bacterially derived immunogenic polypeptides can be loaded on the same plate. The plates are washed with buffer after 1 hour incubation at room temperature. Anti-serum, such as a oat-antiserum or rabbit antiserum to the immunogenic polypeptide, are diluted in buffer and BSA and incubated in the well for 1 hour at room temperature. After washing 4 times with buffer, the wells are probed with, for example rabbit antiserum against goat IgG conjugated with alkaline phosphatase diluted in buffer and BSA. After washing with buffer, the wells are incubated with nitrophenyl phosphate substrate in diethanolamime buffer. After incubation for 10–30 minutes the reaction is stopped by adding NaOH and the absorbance read at 410 nm.

The toxic effect of the polypeptides of the invention on a plant in which the polypeptides are produced can be tested by comparing the growth of plants producing the polypeptides of the invention to plants that do not produce the polypeptides. Preferably, plants producing the polypeptides of the invention have a same or similar rate of growth as plants that do not produce the polypeptides.

Compositions Comprising Immunogenic Polypeptides of the Invention

The invention provides immunogenic polypeptide compositions, such as HBsAg in whole plants, plant cells, plant organs, plant seeds, protoplasts, callus, cell cultures, and any group of plant cells organized into structural and/or functional units capable of expressing at least a polynucleotide of the invention. The plant matter, such as leaves, fruit, and tubers, is preferably administered to a human or animal orally. The invention further comprises immunogenic polypeptides of the invention that have been isolated, processed, purified, or partially purified from the plant cells, or plant tissue in which they were produced. For example, the plant material can be extracted, ground, pulverized, desiccated, homogenized, and the like, to produce a final product in the form of, for example, an extract, juice, liquid, powder, tablet. It is particularly advantageous in certain disease prevention protocols for human infants to produce a vaccine in a juice for ease of administration such as juice of tomato, soybean, and carrot, or milk. The plant material can alternatively be processed in a way that renders it more palatable through the addition of flavor components. It may also be processed so as to concentrate or purify the antigenic components of the plant in order to enhance the immunogenic effect of the composition. Although it is generally not preferred to do so, extracts of the plant material can be obtained, sterilized, and reconstituted as an injectable liquid, which can be administered parenterally if desired.

Preferably, any processing steps used to concentrate or condition the plant material avoids significant denaturing of the immunogenic polypeptides, e.g. HBsAg particles, so that antigenic properties are not lost. The likely immunogenic properties of the composition can be tested ex vivo by screening with anti-HBsAg antibodies. The invention also provides compositions comprising polynucleotides of the invention.

Compositions of the invention can comprise a pharmaceutically acceptable carrier. The carrier should not itself induce the production of antibodies harmful to the host. Pharmaceutically acceptable carriers are well known to those in the art. Such carriers include, but are not limited to, large, slowly metabolized, macromolecules, such as proteins, polysaccharides such as latex functionalized sepharose, agarose, cellulose, cellulose beads and the like, polylactic acids, polyglycolic acids, polymeric amino acids such as polyglutamic acid, polylysine, and the like, animo acid copolymers, peptoids, lipitoids, and inactive virus particles.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, glycerol, dextrose, malodextrin, ethanol, or the like, singly or in combination, as well as substances such as wetting agents, emulsifying agents, or pH buffering agents. Liposomes can also be used as a carrier for a composition of the invention.

If desired, co-stimulatory molecules, which improve immunogen presentation to lymphocytes, such as B7–1 or B7–2, or cytokines such as IL-2, and IL-12, can be included in a composition of the invention. Optionally, adjuvants can also be included in a composition. Adjuvants which can be used include, but are not limited to MF59–0, aluminum hydroxide, N-acetyl-muramyl-L-threonyl-D-isoglutamine (thr-MDP), N-acetyl-nor-muramyl-L-alanyl-D-isoglutamine (CGP 11637), referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) bacterial plasmid DNA, anti-HB antibody, oligodeoxynucleotides containing immunostimulatory CpG, lypophilic derivative of muramyl dipeptide (MDP-Lys (L 18)), aluminum phosphate or aluminum sulfate, core protein of hepatitis C, and RIBI, which contains three components extracted from bacteria, monophosphoryl lipid a, trehalose dimycolate and cell wall skeleton (MPL+TDM+CWS) in a 2% squalene/Tween 80 emulsion.

Preferred adjuvants include cholera toxin (CT), *E. coli* heat-labile enterotoxin (LT), anti-idiotypic antibody 2F10, colonization factor, shiga-like toxin, intimin, monophosphoryl lipid a, OPTIVAX (U.S. Pat. No. 5,622,649), outer surface protein a (OspA), sodium fluoride, chitosan, subunits thereof, and mutants thereof. (Clements et al., Vaccine. 6:269–277 (1988); de Haan et al., Vaccine. 14: 260–266 (1996); De Magistris, "Non-toxic derivatives of heat-labile toxins act as mucosal adjuvants," *Mucosal Immunization: Genetic Approaches & Adjuvants*. IBC Biomedical Library, Southborough, Mass., pp. 1.8.1–1.8.12 (*Based on a presentation at the IBC Conference*, Oct. 16–18, 1995, Rockville, Md.) 1996; Dickinson et al., Infect. Immun. 63:1617–1623 (1995); Di Tommaso et al. Infect. Immun. 64: 974–979 (1996); Fontana et al., *Infect. Immun*. 63: 2356–2360 (1995); Holmgren et al. Vaccine, 11:1179–1184 (1993); Nedrud et al. Reg. Immunol, 3:217–222 (1991); Pride et al., J. Exp. Med. 177:127–134 (1993); and U.S. patents to Thanavala et al.)

The adjuvant can be provided concurrently with, or shortly before or after, provision of the immunogenic composition. Also, the adjuvant can be provided integrally with the immunogenic composition, e.g., as a coexpressed product of the transgenic plant, or it can be provided separately in a convenient form, e.g., as a liquid, to be taken with the product. Preferably, the adjuvant is an immunologically acceptable adjuvant, i.e., one that promotes an immune response without serious deleterious effect.

The compositions of the invention can comprise a sustained release formulation, enteric formulations, tablets, chewable tablets, capsules, solutions, parenteral solutions, intranasal sprays or powders, troches, suppositories, transdermal patches and suspensions. In general, compositions contain at least 0.01, 0.1, 1, 3, 5, 10, 20, 30, 40, 50, 60, 70, or 80% of the polypeptides or polynucleotides of the invention in total, depending on the desired doses and the type of composition to be used.

Method of Eliciting an Immune Response

Immunogenic polypeptides of the invention can be used to elicit an immune response in animals such as cattle, swine, mice, guinea pigs, rabbits, fowl, such as chickens, ducks, and geese, chimpanzees, baboons, and macaques, and in humans. Preferably, the immunogenic polypeptides of the invention elicit IgG and/or IgA antibodies (see examples 21 and 23) and/or a cell-mediated immune response (see example 24).

In a preferred aspect, an immunogenic polypeptide of the invention is a mucosal immunogen, such as HBsAg. For the purposes of the invention, a mucosal immunogen is one that has the ability to specifically prime the mucosal immune system. In an even more preferred embodiment, a mucosal immunogen of the invention is one that primes the mucosal immune system and/or stimulates the humoral immune response in a dose-dependent manner, without inducing systemic tolerance and without the need for excessive doses of antigen. Systemic tolerance is defined herein as a phenomenon occurring with certain antigens which are repeatedly fed to a mammal resulting in a specifically diminished subsequent anti-antigen response.

A mucosal response to an immunogen of the invention is understood to include any response generated when the immunogen stimulates the mucosal immune system. Typically, the gut-associated lymphoid tissue (GALT) will be activated by feeding of the immunogen orally to a subject mammal. Using this route of introduction of the immunogen to the mucosal membranes provides access to the small intestine M cells which overlie the Peyer's Patches and other lymphoid clusters of the GALT. However, any mucosal membrane accessible for contact with an immunogen of the invention is specifically included within the definition of such membranes (e.g., mucosal membranes of the air passages accessible by inhaling, mucosal membranes of the terminal portions of the large intestine accessible by suppository, etc.).

Elicitation of antibodies by the immunogenic polypeptides of the invention can be used, inter alia, to provide model systems to optimize, for example anti-HBsAg antibody responses to HBV and to provide prophylactic or therapeutic treatment against HBV, or other bacteria, viruses or protozoans. For example, detection and/or quantification of anti-HBsAg antibody titers after delivery of an HBsAg polypeptide can be used to identify HBsAg epitopes that are particularly effective at eliciting anti-HBsAg antibody titers. HBsAg epitopes responsible for a strong HBsAg antibody response against HBV can be identified by eliciting HBsAg antibodies directed against HBsAg polypeptides of different lengths. Anti-HBsAg antibodies elicited by a particular HBsAg polypeptide epitope can then be tested using an anti-HBV ELISA assay to determine which polypeptides contain epitopes that are most effective at generating a strong response. HBsAg polypeptides or fusion proteins which contain these epitopes or polynucleotides encoding the epitopes can then be constructed and used to elicit a strong HBsAg antibody response.

An immunogenic polypeptide can be administered to an animal or human to elicit an immune response in vivo. Oral delivery of an immunogenic polypeptide is preferred. Administration of a polypeptide can be by any means known in the art, including oral, intramuscular, intradermal, intraperitoneal, or subcutaneous injection, including injection using a biological ballistic gun ("gene gun"). Administration may also be intranasal. Preferably, an immunogenic polypeptide is accompanied by a protein carrier for oral administration. A combination of administration methods may also be used to elicit an anti-HBsAg immune response. For example, one dose of the immunogenic composition may be administered by one route, such as oral, while another dose or booster may be administered by transdermal, subcutaneous, intravenous, intramuscular, intranasal, or intrarectal route.

A composition of the invention comprising an immunogenic polypeptide, or a combination thereof is administered in a manner compatible with the particular composition used and in an amount which is effective to elicit an immune response to the immunogenic polypeptide, for example an anti-HBsAg antibody titer as detected by an ELISA.

The particular dosages of an antigenic composition of the invention will depend on many factors including, but not limited to the species, age, and general condition of the human or animal to which the composition is administered, and the mode of administration of the composition. An effective amount of the composition of the invention can be readily determined using only routine experimentation. In vitro and in vivo models described herein can be employed to identify appropriate doses. Generally, at least 0.001, 0.001, 0.1, 1.0, 1.5, 2.0, 5, or 10 mg/kg of an antigen will be administered to a large mammal, such as a baboon, chimpanzee, or human. Preferably, 10–100 $\mu$g/kg is administered. If desired, co-stimulatory molecules or adjuvants can also be provided before, after, or together with the antigenic compositions. Immunogenic polypeptides of the invention can be administered therapeutically or prophylactically. Generally, it is desired that the amount of plant or portion thereof to be consumed be sufficient to provide an amount of immunogenic polypeptide, such as HBsAg, comprises at least 0.1, 1, 2, 5, 10, 50, 100, 500 µg/g of food consumed by the animal or human. Further, extracts of the plant material can be prepared and/or concentrated to increase the amount of polypeptide per gram of prepared or concentrated food material, which can then be consumed.

Immune responses, including elicitation of IgG and/or IgA antibodies and/or a cell mediated immune response, in an animal or human generated by the delivery of a composition of the invention can be enhanced by varying the dosage, route of administration, or boosting regimens. Compositions of the invention may be given in a single dose schedule, or preferably in a multiple dose schedule in which a primary course of vaccination includes 1–10 separate doses, followed by other doses given at subsequent time intervals required to maintain and/or reenforce an immune response, for example, at 1–4 months for a second dose, and if needed, a subsequent dose or doses after several months. Preferably, at least one of these administrations is performed orally to elicit a mucosal immune response as well as to take advantage of cost and convenience. Oral administration comprises consuming a transgenic plant or plant part of the invention. Preferably a series of ingestions of the plant material is undertaken, e.g. a series of three four, five, ten, or more, each ingestion being separated by at least three, and preferably by at least about seven to fourteen days.

Administration of immunogenic polypeptides can elicit an antibody titer and/or cellular immune response in the animal or human that lasts for at least 1 week, 2 weeks, 1 month, 2 months, 3 months, 4 months, 6 months, 1 year, or longer. Optionally, an immune response can be maintained in an animal or human by providing one or more booster injections of the immunogenic polypeptide at 1 month, 2 months, 3 months, 4 months, 5 months, 6 months, 1 year, or more after the primary administration. Optionally, the administration of the polypeptides of the invention as plant matter or foodstuff is used as a booster after a primary injection of a composition that elicits an immune response. A desired immunization regimen can include administering one or more booster amounts of the present antigenic complex in order to increase the immune response of the subject. Accordingly, administration of an instant transgenic plant as a primary immunogen, or as a "booster" to the same or other immunogen, is contemplated. For instance, the results of administering transgenic potato slices with CT adjuvant, followed 7–16 weeks later with yeast-derived rHBsAg (commercial) administered i.p. or s.c. are shown in FIGS. 4A–E. Similarly, transgenic potato and CT can be administered as a booster to an initial immunization with rHBsAg, with antibody titers being increased. Initially, an oral booster vaccine for use with individuals who have been primed by parenteral administration of current vaccines is demonstrated. More preferred is an oral vaccine that can be used alone in a vaccination regime for effective protection. The frequency and amount of complex consumed should not be so great as to provoke toleration of the antigen, and this condition can be determined through routine experimentation.

To determine the immunogenicity of plant-derived immunogenic polypeptides of the invention when fed orally, extracts or plant tissues from plants expressing the immunogenic polypeptides of the invention can be fed to animals, such as mice or humans. For example, one group of mice can be fed an extract of a plant or a plant tissue where the plant expresses a polypeptide of the invention. Another group of mice can be given recombinant polypeptides purified from E. coli expressing the same antigen from a recombinant plasmid. Serum and mucosal antibody responses can be examined by ELISA.

It is known that HBsAg antibody titers of 10 mIU/mL are protective in humans. It is recommended that current vaccines generate antibody titers of at least 100 mIU/mL to allow for a decline in titers with time. Preferably, a primary immune response elicited by an HBsAg immunogenic polypeptide of the invention achieves an anti-HBsAg serum antibody level greater than 50 mIU/mL in four or less feedings. Where the compositions of the invention serve as a booster it is preferred that the anti-HBsAg serum antibody level increases at least four fold or greater than 500 mIU/mL in four or less feedings.

In oral HBsAg immunization studies, cholera toxin (CT, 10 µg/dose) or LT has been used as an adjuvant. For example, CT is placed onto potato tuber slices expressing the HBsAg and consumed by animals in conjunction with the antigen. The CT is effective in enhancing the immune response associated with HBsAg. Preliminary data indicate that CT is a more effective oral adjuvant for HBsAg than the E. coli heat labile toxin $LT_{R192G}$ mutant developed by John Clements of Tulane University. Significantly, secretory IgA antibodies can be detected following feeding of recombinant tubers; which are not elicited with parenteral administration of HBsAg.

Illustrative of the invention is the feeding of mice with 5 g of recombinant potato coated with 10 µg CT three times at weekly intervals. This program gives peak antibody titers of 70–110 mIU/mL, which can be boosted to titers of 1700–3400 mIU/mL by a single sub-immunogenic i.p. dose of HBsAg purified from recombinant yeast (Merck). The actual titers measured are correlated to HBsAg expression levels in potato. The level of dose response is dose-related with potatoes delivering 1.1 µg/g HBsAg giving a lower and less prolonged response than potatoes delivering 8.3 µg/g. The same feeding regime is found to boost a single s.c. dose of HBsAg purified from recombinant yeast to give peak antibody titers of 1000 mIU/mL. Boiled tubers (5 min, 100° C.) gave no detectable immune response but a significant boost was observed on subsequent administration of a single i.p. dose of HBsAg purified from recombinant yeast.

The following are provided for exemplification purposes only and are not intended to limit the scope of the invention described in broad terms above. All references cited in this disclosure are incorporated herein by reference.

EXAMPLES

Example 1

Construction of HB101 and HB102 Vectors pHB101: The HBsAg coding region on the Pst I/HindIII fragment from pMT-SA (kindly provided by Li-he Guo, Chinese Academy of Sciences) was subcloned into pBluescript KS (Stratagene) to form pKS-HBS. The HBsAg gene in pKS-HBS was opened 116 base pairs (bp) 3' to the termination codon with BstBI and the resulting ends were blunted by filling with Klenow enzyme and dCTP/dGTP. The entire coding region was then excised 16 bp upstream of the Pst I site with BamHI. pBI 121 (Clontech Laboratories, Palo Alto, Calif.) was digested with Sac I and the ends were blunted with mung bean nuclease. The GUS coding region was then released with BamHI and the vector was isolated. The HBsAg coding fragment was ligated into the GUS-less pBI121 to yield pHB101, where its expression is driven by the cauliflower mosaic virus (CaMV) promoter derived from pBI121.

pHB102 (FIG. 1A): The CaMV 35S promoter with duplicated enhancer linked to the tobacco etch virus (TEV) 5' untranslated leader sequence, which acts as a translational enhancer (Carrington, et al. J. Virol., 64:1590–1597 (1990), was excised from pRTL2-GUS (Carrington et al. Plant Cell 3:953–962 (1991)) as follows. pRTL2-GUS was digested with Nco I and the ends were blunted with mung bean nuclease. The promoter-leader fragment was then released by digestion with HindIII. pHB101 was digested with HindIII and Sma I to release the 35S promoter fragment, and the vector was purified. The promoter-leader fragment was then ligated into the HindIII/Sma I-digested pHB101 to yield pHB102. The HBsAg coding region lies upstream of the nopaline synthase terminator in both constructs. The plasmids contain the left and right border regions, which denote the limits of the DNA that is integrated into the plant genomic DNA via *Agrobacterium tumefaciens*-mediated transformation, as well as the neomycin phosphotransferase gene, which allows selection with kanamycin.

Example 2

Deletion from HB102 of Native 5' and 3' Untranslated Regions of HBsAg cDNA pHB103 (FIG. 1A): Construction of plasmid HB102 is described above and in Mason, H., et al. (1992). Deletion of selected viral untranslated sequences was observed to improve accumulation of the recombinant protein in plants. Thus, construct HB103 is identical to HB102 except for deletion of the noncoding viral sequences, which might decrease transcription rate or translation efficiency. The HBsAg coding region from plasmid pKS-HBS (Mason et al., 1992) was amplified by PCR with the oligos HBNco (5' CATGCCATGGAGAACACAACATCA GG 3' ) (SEQ ID NO:7) and HBSac (5' GCC GGA GCT CAA ATG TAT ACC CAA AGA CA 3' )(SEQ ID NO:8). These introduced an NcoI site at the start codon and a SacI site at the stop codon of the coding region. The PCR fragment was cloned using the NcoI and SacI sites into the intermediate vector designated pIBT210.1 (Haq et al., Science 268:714–716 (1995)), which resulted in the plasmid pIBT210.1HBsC#10.

The XhoI to SacI fragment from pIBT210.1HBsC#10 was subcloned into pBluescript SK+to create the intermediate pBSSKHBsC#6. The unmodified XhoI to SacI fragment was subcloned into pIBT211.1 to form the intermediate pIBT211.1HBsC#9. Vector pIBT211.1 was made by ligation of the Nos terminator fragment obtained by digestion of pBI101 (Clontech; Jefferson et al., EMBO J. 13:3901–3907 (1987)) with SacI and EcoRI into the same sites of pIBT210.1, with elimination of the VSP terminator. The HindIII/EcoRI fragment from pIBT211.1 HBsC#9 was subcloned into the plant transformation vector pBI101 to create pHB103. This plasmid contains the 35S promoter with duplicated enhancer, TEV leader, HBsAg coding region, and Nos terminator between the HindIII and EcoRI sites. The expression cassette and restriction map of HB103 are shown in FIG. 1A and FIG. 2A, respectively.

Example 3

Modifications of HB103

The following constructs are all modifications of HB103 in which a 35S promoter is operably linked to native virus-derived (wild-type) HBsAg cDNA. Relevant cassettes are shown in FIG. 1A.

35S-TEV-HBsAg-SEKDEL-NOS construct.

pHB105(FIG. 1A) contains a deletion of the C-terminal Ile codon of the HBsAg coding sequence and an insertion encoding the C-terminal extension SEKDEL (SEQ ID NO:4). An intermediate clone was constructed by a three-fragment ligation consisting of the XhoI to AccI fragment from pIBT210.1HBsC#10, the AccI to SacI fragment obtained by annealing two oligonucleotides: (aSEKDELs-F: 5' ATACTCTGAGAAAGATGAGCTATGAGAGCT3' (SEQ ID NO:9) and aSEKDELs-R: 5' CTCATAGCTCATCTTTCTCAGAGT3' (SEQ ID NO:10) with a XhoI to SacI fragment of pBluescript SK+. The resulting plasmid, pBSSKHBsCK#3, was subeloned as described above for pHB103 by the XhoI/SacI fragment into pIBT211.1, and then the HindII/EcoRI fragment into pBI101 to give pHB105.

35S-TEV-VSPαS-HBsAg-NOS construct.

pHB106(FIG. 1A) contains an insertion encoding the soybean VSP "αS" signal peptide (Mason et al., 1988), creating an N-tenninal extension of the HBsAg coding sequence with 21 amino acids encoded by: CCATGGCAATGAAGGTCCTTGTTTTCTTCGTTGCTACAATTTTGGTAGCATG GCAATGCCATACC (SEQ ID NO:11). pBSSKHBsC#6 was digested with NcoI and ligated with the 67 bp NcoI fragment from pVSP-alpha-Sig-GUS (DeWald, Ph.D. Thesis, Dept. of Biochemistry & Biophysics, Texas A&M University, College Station, TX. (1992)). The resulting plasmid, pSKHBsC-alphaS#90, was subdloned as described above for pHB103 by the XhoI/SacI fragment into pIBT211.1, and then the HindIII/EcoRI fragment into pBI101 to give pHB106.

35S-TEV-VSPαL-HBsAg-NOS construct.

pHB107(FIG. 1A) contains an insertion encoding the soybean VSP "αL" signal peptide (Mason et al., 1988), creating an N-terminal extension of the HBsAg coding sequence with 34 amino acids encoded by: CCATGGCAATGAAGGTCCTTGTTTTCTTCGTTGCTACAATTTTGGTA GCATGGCAATGCCATGCGTACGATATGTTCCCTCTCCGAATGAACACTGGCTATGGTGCC (SEQ ID NO:12). pBSSKHBsC#6 was digested with NcoI and ligated with the 106 bp NcoI fragment from pVSP-alpha-Leader-GUS (DeWald, 1992). The resulting plasmid, pSKHBsC-alphaL#L1, was subcloned as described above for pHB103 by the XhoI/SacI fragment into pIBT211.1, and then the HindIII/EcoRI fragment into pBI101 to give pHB107.

35S-TEV-VSPαS-HBsAg-SEKDEL-NOS construct.

pHB108 contains an insertion into pHB105 encoding the soybean VSP "αS" signal peptide (Mason et al., 1988), creating an N-terminal extension of the HBsAg coding sequence with 21 amino acids encoded by: CCATGGCAATGAAGGTCCTTGTTTCTTCGTTGCTACAATTTTGGT AGCATGGCAATGCCATACC (SEQ ID NO:13). pBSSKHBsCK#3 was digested with NcoI and ligated with the 67 bp NcoI fragment from pVSP-alpha-Sig-GUS (DeWald, 1992). The resulting plasmid, pSKHBsCKalphaS#23, was subcloned as described above for pHB103 by the XhoI/SacI fragment into pIBT211.1, and then the HindIII/EcoRI fragment into pBI101 to give pHB108.

35S-TEV-VSPαL-HBsAg-SEKDEL-NOS construct.

pHB109 contains an insertion into pHB105 encoding the soybean VSP "αL" signal peptide (Mason et al., 1988), creating an N-terminal extension of the HBsAg coding sequence with 34 amino acids encoded by: CCATGGCAATGAAGGTCCTTGTTTTCTTCGTT GCTACAATTTTGGTAGCATGGCAATGCCATGCGTACGATATGTTCCCTCTCCGAATGAACACTGGCT ATGGTGCC (SEQ ID NO:14). pBSSKHBsCK#3 was digested with NcoI and ligated with the 106 bp NcoI fragment from pVSP-alpha-Leader-GUS (DeWald, 1992). The resulting plasmid, pSKHBsCKalphaL#29, was subcloned as described above for pHB103 by the XhoI/SacI fragment into pIBT211.1, and then the HindIII/EcoRI fragment into pBI101 to give pHB109.

35S-TEV-TPSS-HBsAg-NOS construct.

pHB110 (FIG. 1A) contains an insertion into pHB103 encoding the transit peptide and partial mature peptide from the N-terminus of pea rbcS (Nawrath et al., "Plastid targeting of the enzymes required for the production of polyhydroxybutyrate in higher plants," In "Biodegradable Plastics and Polymers, eds. Doi Y, Fukuda K, Elsevier, Amsterdam, pp. 136–149 (1994)), creating an N-terrninal extension of the HBsAg coding sequence with 82 amino acids encoded by: CCATGGCTTCTATGATATCTTCTTC-CGCTGTGACAACAGTCAGCCGTGC-CTCTAGGGGGCAATCCGCCG CAATGGCTCCATTCG-GCGGCCTCAAATCCATGACTGGATTCCCAGTGAA GAAGGTCAACACTTGACAT TACTTCCATTACAAG-CAATGGTGGAAGAGTAAAGTGCATGCAG-GTGTGGCCTCCAATTGGAAAGAAG AAGTTTGAGACTCTTTCCTATTTGCCAC-CATTGACCAGAGATTCCATGG (SEQ ID NO:15).

pUC-TPSS (Nawrath et al., 1994) was subjected to PCR with the primers 5' TPSS (5'-GGATCCATGGCTTCTATGATATCTT-3' (SEQ ID NO:16)) and 3' TPSS (5'-GGATCCATGGAATCTCTGGT CAATGGTGG -3' (SEQ ID NO:17)) that were designed to add NcoI sites to each end of the rbcS sequence. pBSSKH-BsC#6 was digested with NcoI and ligated with the NcoI-digested PCR product containing the TPSS coding region. The resulting plasmid, pHB211.1TPSS#23, was subcloned as described above for pHB103 by the XhoI/SacI fragment into pIBT211.1, and then the HindIII/EcoRI fragment into pGPTV-Kan (Becker et al., 1992) to give pHBT110.

Example 4

Alternative Termination Sequences Affect Protein Accumulation

The constructs discussed in Example 3 contain the tobacco etch virus (TEV) untranslated leader and the nos 3' end. Vectors pHB104 (FIG. 1A) and pHB114 (FIG. 1A), respectively, contain the vsp and pin2 3' terminal ends instead of the nos 3' end. These vectors displayed a higher level of protein accumulation per mRNA than HB103. pHB104 was obtained by subcloning the fragment from Sac to EcoRI from pIBT210.1HBsC#10 into pHB103 to replace the Nos terminator with the VSP terminator. The expression cassettes are shown in FIG. 1.

pHB114 contains the 400 bp potato pin2 terminator (An et al., 1989). pDP687 (Pioneer Hi-Bred International; Johnson City, Iowa) was digested with BamHI and EcoRI and the 400 bp pin2 terminator subcloned into pBlue-scriptKS. The resulting pBlueKS-pin2 was digested with SacI and EcoRI to obtain the pin2 terminator fragment, which was ligated with pHB103 digested with SacI and EcoRI to form pHB114.

Example 5

Construct with TMV Ω Leader pHB111 (FIG. 1A) contains the tobacco mosaic virus "Ω" UTR (Gallie et al., 1992) instead of the TEV UTR. An EcoRV/XhoI fragment from plasmid pBSG660 (Biosource Technologies, Inc., Vacaville, Calif.) containing the 3' end of the 35S promoter and the Ω-UTR was subcloned into the EcoRV/Xho I sites of pIBT211.1HBsC#9 to create the intermediate plasmid pHB211Ω-5'. In order to delete the TEV leader, pHB211Ω-5' was digested with XhoI and NcoI, followed by mung bean nuclease to blunt the ends, and blunt ligation. The resulting plasmid pHB211 was digested with HindIII to EcoRI and the expression cassette was cloned into pGPTV-KAN (Becker et al. 1992) to give pHB111.

Example 6

Alternative Promoter Sequences

The 35S promoter from cauliflower mosaic virus is a strong constitutive promoter that expresses in almost all plant tissues. Other promoters tested are the promoter for patatin, which is the major storage protein in potato, and the promoter for granule bound starch synthase (GBSS). Both promoters drive strong expression in the tuber. These constructs are identified as HB145 (FIG. 1A) and HB165 (FIG. 1A) and shown in FIG. 1. Microtuber formation must be induced to test expression levels because leaf tissue cannot be analyzed with these constructs.

A. Patatin-TEV-HBsAg-SEKDEL-NOS Construct.

pHB145 contains the potato tuber-specific patatin gene promoter in place of the CaMV 35S promoter in pHB105. pIBT240.1 was obtained by subdloning the HindIII/BamHI patatin fragment from pPS20-GUS (Wenzler et al., Plant Mol. Biol., 12:41–50 (1989) into the HindIII/XhoI sites of pIBT210.1. The NcoI/SacI fragment from pBSSKHBsCK#3 was ligated to pIBT240.1 digested with NcoI and SacI, and the HindIII to EcoRI fragment of the resulting plasmid was subcloned into pBI101 to give pHB145.

B. GBSS-TEV-HBsAg-SEKDEL-NOS Construct.

pHB165 contains the tuber-specific granule-bound starch synthase (GBSS) promoter (Visser et al., Plant Mol. Biol., 17:691–699 (1991)) in place of the CaMV 35S promoter in pHB105. pPGB1 (Visser et al., 1991) was digested with SalI and SacI and ligated with the XhoI to SacI fragment from pBSSKHBsCK#3 to form pHB165.

C. Pin2-TMVΩ-HBsAg-pin2 Construct.

pHB131 contains the native HBsAg coding sequence driven by the potato pin2 promoter fused to the tobacco mosaic virus (TMV) "Ω" 5' UTR (Gallie et al., 1992), and terminated by the potato pin2 3' element. The pin2 promoter is wound-inducible and may allow controlled expression of HBsAg in tubers. The construction involved an intermediate step to obtain the pin2–3' element on a SacI-EcoRI fragment, in which the SacI-PstI fragment of pRT38 was subcloned in pBluescriptKS to form pKS-RT38. The pin2 promoter (Palm et al., Proc. Natl. Acad. Sci. USA 87:603–607 (1990)) was obtained from pRT24 (Robert Thornburg, Dept. of Biochemistry & Biophysics, Iowa State University, Ames, Iowa. 50011). The HindIII-BamHI fragment of pRT24 (1 kb) and the pKS-ΩHB/BamHI-SacI (750 bp) fragments were ligated into pUC-V (containing the soybean vspB terminator) digested with HindIII/SacI to obtain pHB231. The SacI-EcoRI fragment of pKS-RT38 (Robert Thornburg, Dept. of Biochemistry & Biophysics, Iowa State University, Ames, Iowa 50011) containing pin2–3' terminator was then obtained and ligated with pHB231/HindIII-Nco1 containing the pin2-TMV Ω promoter-leader element, the pHB103/Nco1-Sac1 fragment containing the HBsAg coding sequence, and pGPTV-Kan/HindIII-EcoR1 to give pHB131.

D. Patatin-TMVΩ-HBsAg-vspB Construct.

pHB140.3 contains the native HBsAg coding sequence driven by the potato tuber-specific patatin gene promoter fused to the tobacco mosaic virus (TMV) "Ω" 5' UTR (Gallie et al., 1992), and terminated by the soybean vspB 3' element. A BamHI site was created at the 5' end of the TMV Ω UTR using the mutagenic primer "Omega-Bam" (5'-GATCGGATCCTTACAACAATTACCAAC-3' (SEQ ID NO:18)). Using pHB211 as a source of the TMV Ω5'-UTR, PCR was performed using the "Omega-Bam" primer and a downstream primer, "NOS" (5'-CGGCAACAGGATTCAATC-3' (SEQ ID NO:19)), and a PCR fragment of approximately 800 bp was cloned into T-tailed pBluescriptKS to give pKS-ΩHB. The pPS20/HindIII-BamH1 fragment (2.35 kb patatin promoter) was ligated with pKS-ΩHB/BamHI-SacI (750 bp) and pUC19/HindIII-Sac1 (2.7 kb) to give pPS-ΩHB. Finally, the pUC-V/SacI-EcoR1 fragment containing the soybean vspB terminator was ligated into pPS-ΩHB to give pHB240.3, which contains the patatin promoter fused to the TMV "Ω" 5' UTR, and terminated by the soybean vspB 3' element. The expression cassette was obtained by digestion of pHB240.3 with HindIII and EcoRI, and ligated into pGPTV-Kan to give pHB140.3.

Example 7

Plant-optimized Codons for HBsAg

The preference for codon usage varies among plants and animals and many signals within the DNA sequence are not conserved (Ausubel, F. et al., eds. (1994) *Current Protocols in Molecular Biology*, vol. 3, pp. A.1C.3). For instance, a 10–20 fold increase in expression of a synthetic gene over the native bacterial sequence has been expressed in plants.

Analysis of the native HBsAg gene reveals that 9.7% of the codons are unfavorable for monocots and 8.8% are unfavorable for dicots (such as potatoes). In particular, there is a RNA Pol II termination sequence near the beginning of the gene, 29 CnG trimers and 16 CG dimers. These signals may affect elongation and stability of the transcript, and therefore decrease HBsAg protein. Therefore, unfavorable codons and undesirable signal sequences, splice sites, and methylation sites can be changed while maintaining the same or similar native amino acid sequence. For HBsAg a total of 160 of 681 bases were changed while maintaining the native amino acid sequence of the protein. See SEQ ID NO:3 (FIG. 22) and SEQ ID NO:5 (FIG. 5). The resulting AT content is 52.42% and unfavorable signal have been altered. The vectors are provided with the VSP 3' termination signal discussed above and an αL signal peptide has been provided in one. These vectors are designated HB115–HB117 (FIG. 1A and 21)

A. 35S-TEV-sHBsAg-VSP Construct.

pHB115 (FIG. 1A and 21) contains a synthetic plant-optimized sequence encoding the HBsAg protein. The HBsAg native sequence was scanned for codon use and for potential problem sequences, including spurious mRNA processing signals such as polyadenylation signals, splices sites, and transcription termination signals, mRNA destabilizing sequences such as "ATTTA" (Ohme-Takagi et al., Proc. Natl. Acad. Sci. USA 90:11811–11815 (1993)) and "DST" sequences (Newman et al., Plant Cell 5:701–714 (1993)), and the cytosine methylation motif "CCGG".

Figure 6:
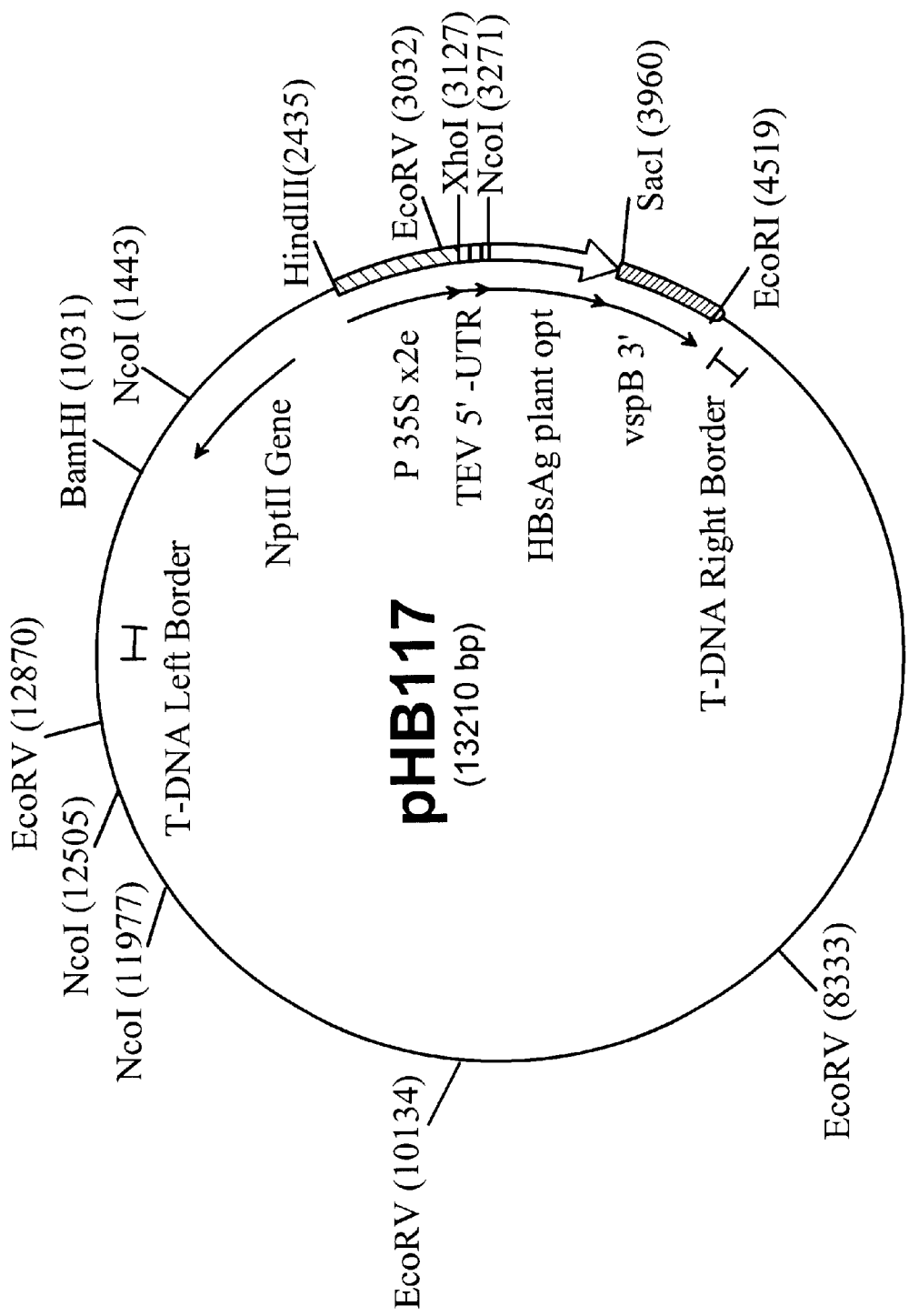

A plant-optimized gene was designed that uses plant-preferred codons and lacks the potential problem sequences. The designed gene was then assembled from overlapping oligonucleotides using the method described by Stemmer et al., 1992. The final product was digested with NcoI and SacI and cloned into pGem5Zf+. The clones #7 and #3 had one mistake each so the 5' from #7 was combined with the 3' of #3. A HincII/SacI fragment was isolated from #7 and a NcoI/BbsI fragment was isolated from #3. These fragments were cut with BfaI and ligated together with the pGEM5Zf+ vector cut with NcoI and SacI. The resulting clone, #8 was sequenced, named psHB312, and subcloned into pIBT210.1 at the NcoI and SacI sites (mini #18), then subcloned into pGPTV-Kan at the HindIII and EcoRI sites to make pHB115. This clone was subsequently found to contain one nucleotide error (nt 595 is "G" instead of "T", which causes a single amino acid substitution Gly for Trp) in the HB coding region which led to the creation of a corrected version, pHB117 (see below).

pHB117 (FIGS. 6 and 21)is the same as pHB115 with the nucleotide correction in the HBsAg gene. The incorrect nucleotide in psHB312 (position 595 "G") was corrected to "T" by site-directed mutagenesis (Axis Genetics plc, Cambridge, England) and named pHBV10. The NcoI to SacI fragment was subdloned into pIBT210.1 to create pIBT210.1HBV then the HindIII/EcoRI fragment subcloned into pGPTV-Kan to give pHB117.

B. 35S-TEV-VSPαL-sHBsAg-VSP Construct.

pHB116(FIGS. 1A and 21) contains the soybean VSP "αL" sequence inserted at the 5' of the synthetic HBsAg gene contained in pHB1115. The NcoI fragment from pSKHBsC-alphaL#29 was ligated to the NcoI to SacI fragment of psHB312 and the vector pIBT210.1 digested with NcoI and SacI (mini #4 alphaL), then subcloned into pGPTV-Kan (Becker, D., et al. 1992) at the HindIII and EcoRI sites.

Figure 7:
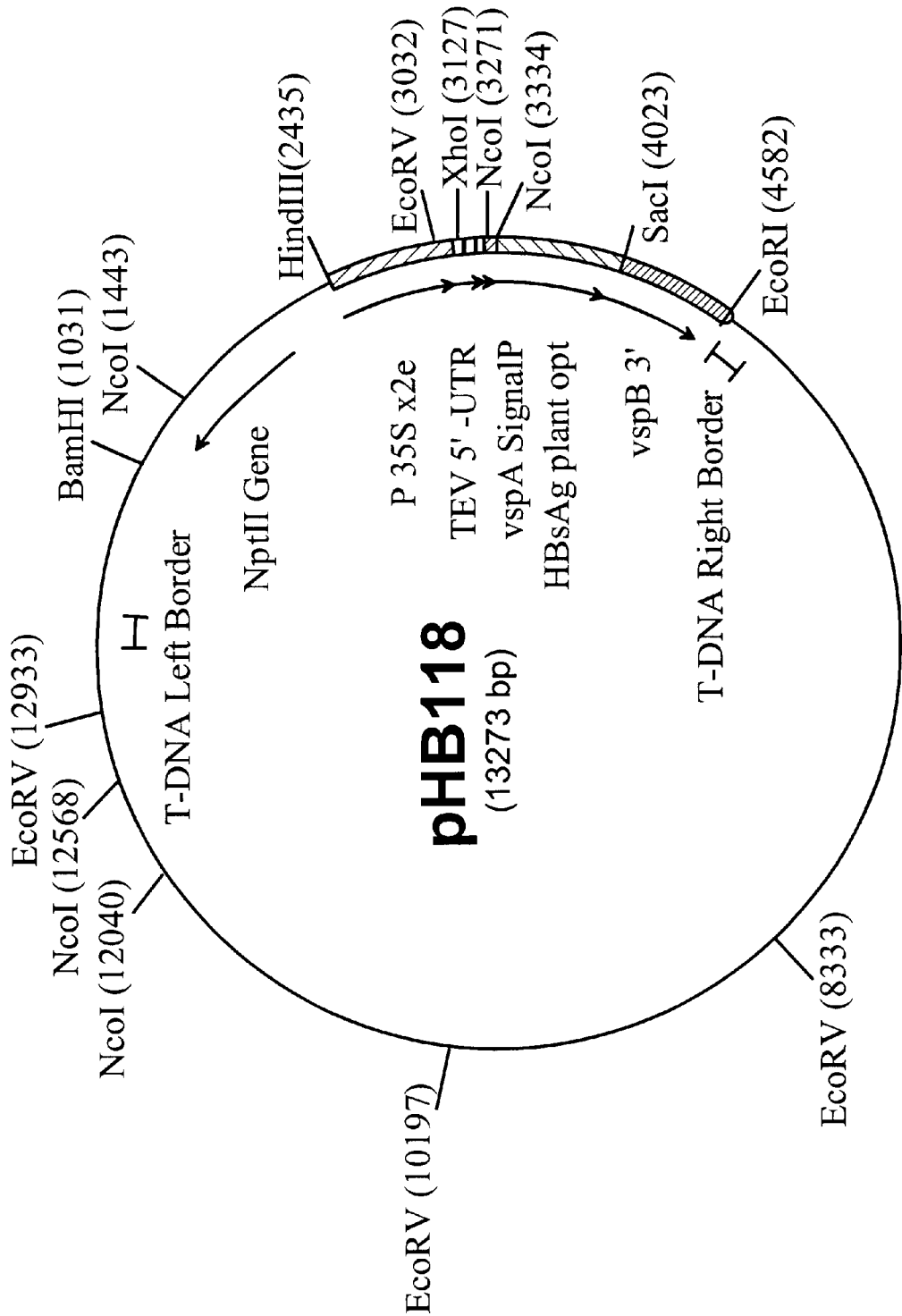

C. 35S-TEV-αS-sHBsAg -VSP Construct pHB118 (FIGS. 7 and 21) contains the soybean "αS" sequence inserted at the 5' of the synthetic HBsAg of pHB117. The NcoI fragment containing the "αS" from pIBT210.1HBsCKaS (pHB308) was ligated to psHB317 to make psHB318. The HindIII to EcoRI fragment was then ligated to pGPTV-Kan to make pHB118.

Figure 8:
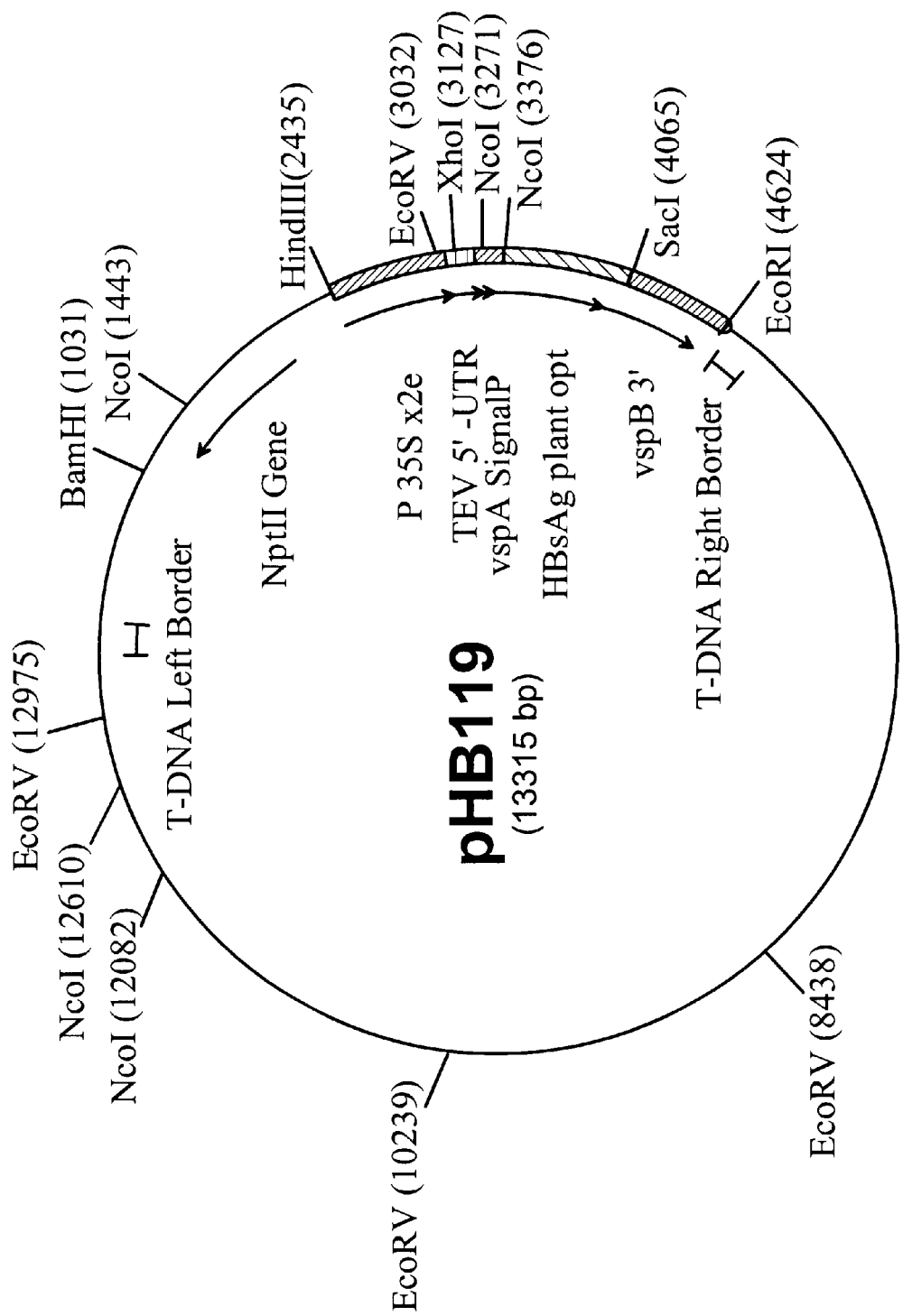

D. 35S-TEV-αL-sHBsAg -VSP Construct pHB119 (FIGS. 8 and 21) contains the soybean "αL" sequence inserted at the 5' of the synthetic HBsAg of pHB117. The NcoI fragment containing the "αL" from pIBT210.1HBsCKαL (pHB309) was ligated to psHB317 to make psHB319. The HindIII to EcoRI fragment was then ligated to pGPTV-Kan to make pHB119.

Figure 9:
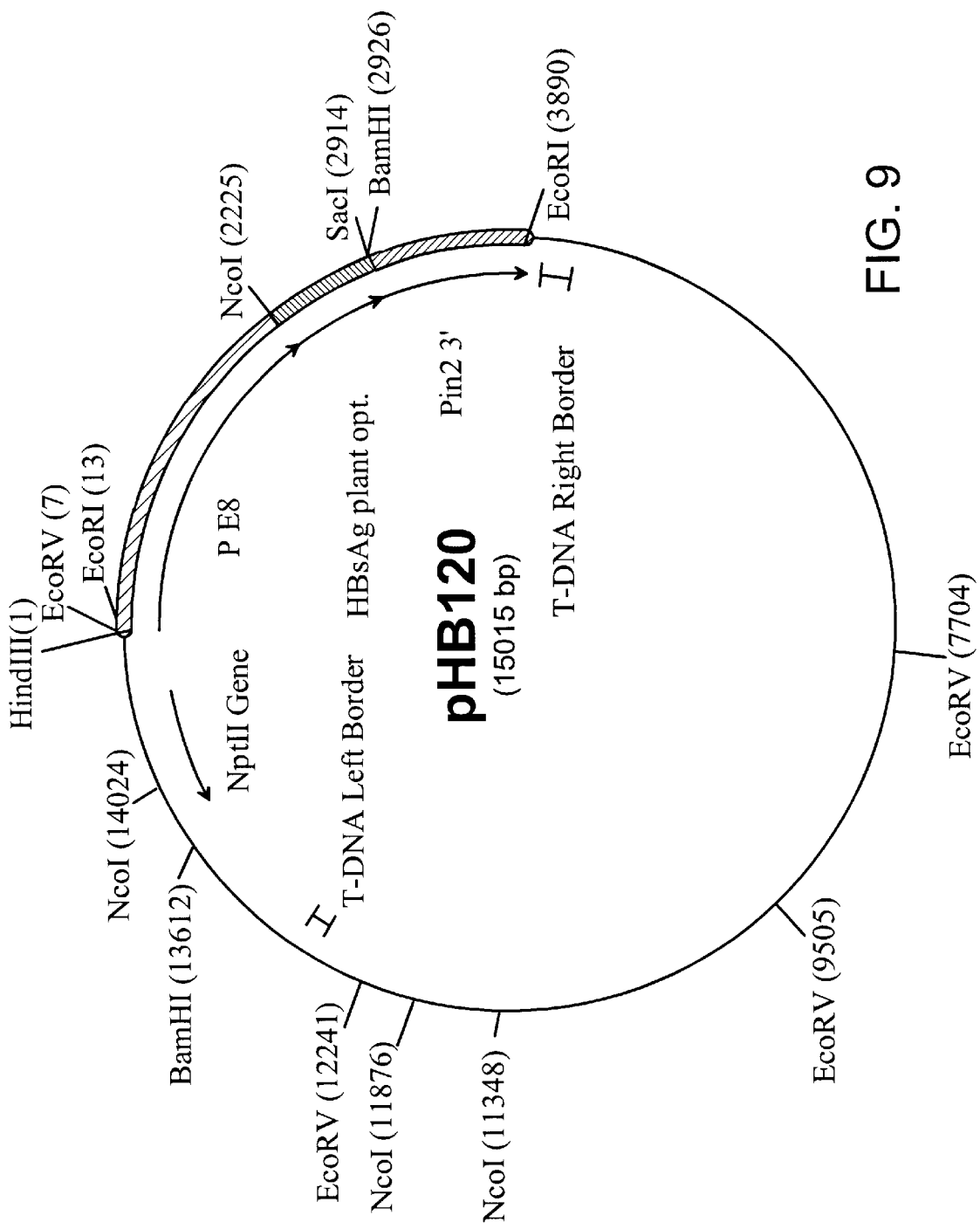

E. E8- sHBsAg-pin2 Construct pHB120 (FIGS. 9 and 21) contains the E8 promoter linked to the sHBsAg with the pin2 3' end. The NcoI to SacI fragment containing sHBsAg gene from psHBV10 was ligated to the EcoRI to NcoI E8 promoter and pBluescript II SK+ digested with EcoRI and SacI to make psHB520. The HindIII to SacI fragment from psHB520 was ligated to HindIII and SacI digested HB131 containing the pin2 terminator resulting in pHB120.

Figure 10:
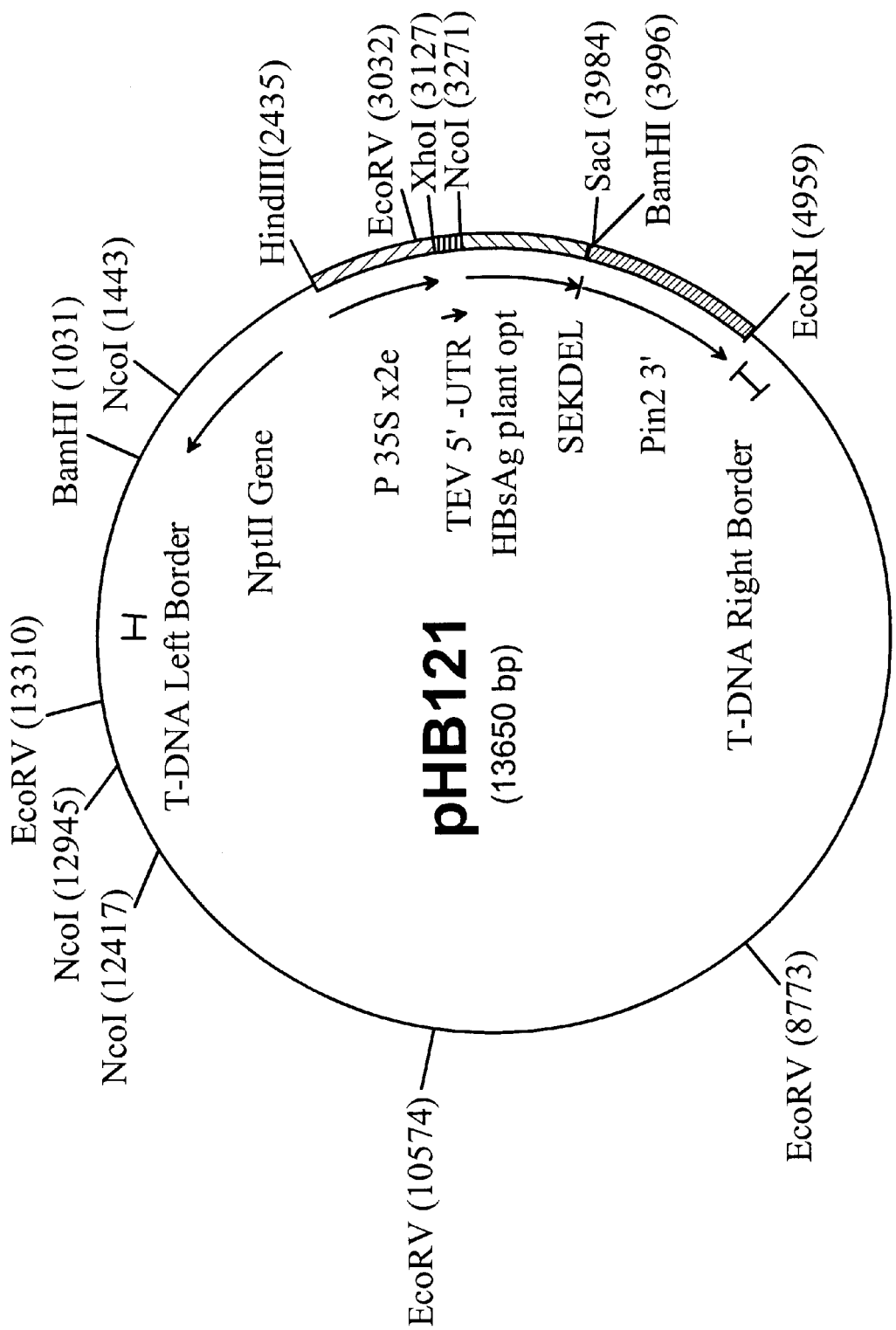

F. 35S-TEV-sHBsAg-SEKDEL-pin2 pHB112 (FIGS. 10 and 21) contains the endoplasmic retention signal inserted at the 3' of the sHBsAg gene. The oligos 5' ATCTCTGAGAAGGATGAGCTTTAA 3' (SEQ ID NO:20) and 3' GACTCTTC CTACTCGAAATTTAGA 5' (SEQ ID NO:21) were hybridized and ligated to psHBV10 digested with BbsI resulting in psHB521. The NcoI to SacI fragment from psHB521 was ligated to the HindIII to SacI fragment from HB131 including the pGPTV Kan vector with the pin2 terminator and ligated to the HindIII to NcoI fragment from pIBT210.1 containing the 35 S promoter to create pHB121.

Figure 11:
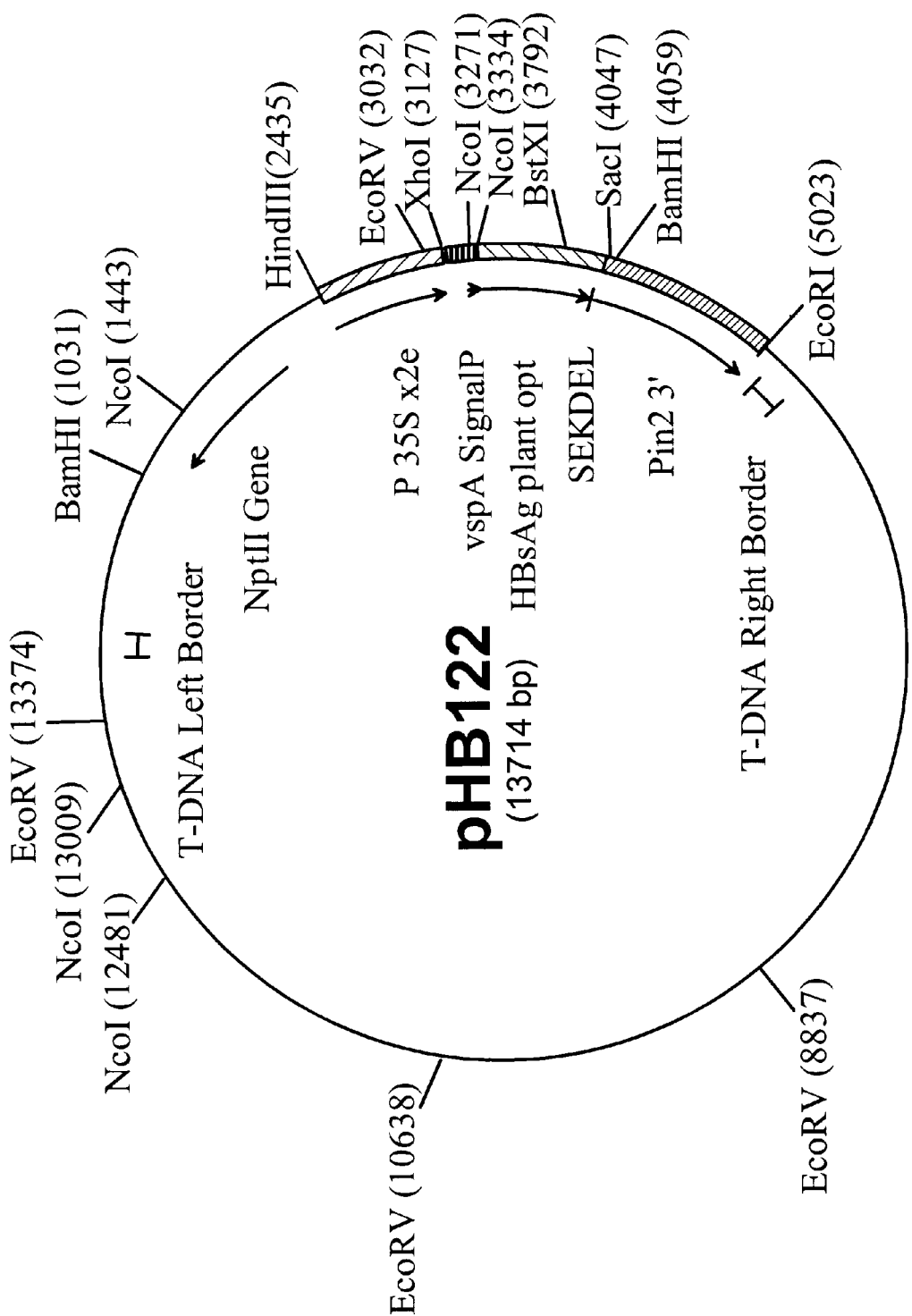
Figure 12:
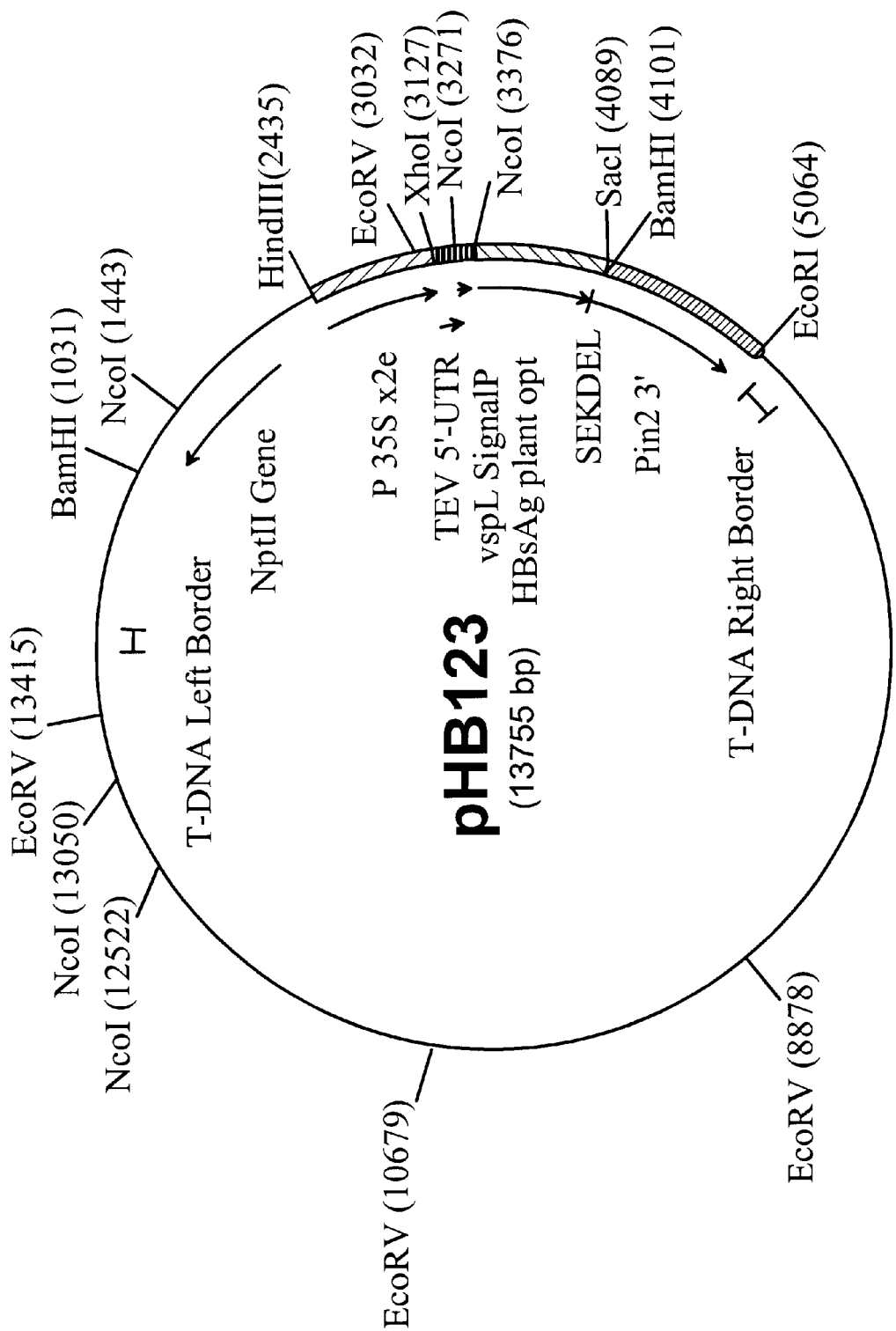

G. 35S-TEV-aS-sHBsAg-SEKDEL -pin2 pHB122 (FIGS. 11 and 21) combines the αS signal with the KDEL (SEQ ID NO:22) signal on the sHBsAg. The BstXI fragment from pHB121 containing the 3' end of the sHBsAg with SEKDEL (SEQ ID NO:4) and the pin2 terminator was ligated into pBB118 replacing the 3' end of the sHBsAg gene and the vsp terminator to make pHB122.

H. 35S-TEV-αL-sHBsAg-SEKDEL -pin2 pHB123 (FIGS. 12 and 21) combines the αL signal with the KDEL (SEQ ID NO:22) signal on the sHBsAg. The BstXI fragment from pHB121 containing the 3' end of the sHBsAg with SEKDEL (SEQ ID NO:4) and the pin2 terminator was ligated into pHB119 replacing the 3' end of the sHBsAg gene and the vsp terminator to make pHB123.

Example 8

Transformation of Potato Plants.

Stable transformation of potato (*Solanum tuberosum* "Frito-Lay 1607") is achieved by axenic leaf disc co-cultivation. Haq, T. et al. (1995); Wenzler, H. et al. (1989). The steps are summarized as follows: Explants are cut and put abaxial side up on LCI plates for 3–4 days. Explants are placed in agro dilution for 10 minutes (agitation by hand), then blotted on sterile paper towel. After blotting, explants are put abaxial side up back on LCI plates for 3–4 days. After cocultivation, explants are put on LC1 CK plates containing kanamycin and carbenicillin for 5–7 days until callus is developed. Explants with well developed callus are placed in LC2CK boxes for 2 weeks; after 2 weeks explants are placed on fresh LC2CK media and shoots are developed. When the shoots are about 1.5 cm in length, they are transferred to cm media for root formation. Carbenicillin is added to cm media to prevent bacterial growth in excess.

Growing Agrobacterium—LB stock: One colony is cultured overnight in presence of kanamycin; YM stock: one colony is cultured over 36–48 hour period in presence of kanamycin.

Because some variation in expression among independent transformation events is expected due to random site of insertion, independent transgenic lines are screened by Northern blot using coding region-specific probes. When a 35S promoter is used, the total RNA from leaves is screened. When the patatin promoter is used, RNA is obtained from microtubers developed in axenic culture. The patatin promoter constructs are screened from microtubers generated by subculture of stem node cuttings from nascent transformed shoots on media high in sucrose. The most promising transformed lines are propagated by axenic culture of node cuttings; and rooted plantlets are transplanted to soil and grown in the greenhouse.

To obtain tubers, the plants are grown in a two-stage protocol: (1) for the first 1.5–2 months, or until sufficient vegetative growth develops, using long day (16 h) lighting with supplemental lighting in winter, and (2) for an additional 1.5–2 months under short day (12 h) conditions. The tubers are typically recovered in yields of 600–800 g per 3-gallon pot after this 3–4 month regime. Tubers harvested from the first crop can be used to initiate new plants after a 1-month dormancy period.

Example 9

Increase of HBsAg Accumulation in Plant Cells

The level of HBsAg expression in plant cells can be increased by incorporating improvements in the plant expression vector that increase transcription/translation of the foreign gene. Transcription, mRNA processing and accumulation, translation, post-translational processing and accumulation can be affected by components of the expression vector. Preliminary studies have demonstrated a critical cellular threshold concentration at which assembly of VLPs consisting of HBsAg subunits is accelerated, and that VLPs are more stable than unassembled subunits. HBsAg mRNA (measured by densitometry of Northern blot signal) is linear when plotted against rHBsAg protein (measured by ELISA) for the constructs HB103 and HB107. A possible explanation for this result is that the HBsAg is more stable/resistant to plant cytoplasmic proteases if it is effectively directed to the ER.

Example 10

Transformed potato plants are grown in pots in a glasshouse or growth. Transgenic plants expressing HBsAg showed an altered growth habit although tubers were produced, which could limit absolute levels of antigen expression in plants. The results of HBsAg protein assays in leaf tissue and tuber tissue of potatoes transformed with the various constructs shown in FIG. 1 are given in Table 2. The level of HBsAg is shown as % total soluble protein for the highest expressing individual transformant for each construct. There is considerable variation in HBsAg expression levels between lines transformed with pHB1114, varying from 0.2 to 16 μg per g tuber. The HBsAg protein forms particles in planta and may be glycosylated. Three potential N-glycosylation sequences occur in the antigen, along with numerous possible locations for O-linked glycosylation. It is believed that only one of the N-linked sites is glycosylated in mammalian systems and only to 40–50%. Data from earlier studies in transgenic tobacco show that plants can assemble HBsAg into virus-like particles (VLPs) similar in size to VLPs derived from recombinant yeast and from sera of infected individuals (although the size distribution differs). The precise localization of the antigen within a tuber is not known, although protein levels are thought to be highest in the layer just underneath the skin. Amounts of purified/extracted HBsAg can be increased by addition of B-mercaptoethanol to the extraction buffer.

TABLE 2

| | slope | HBsAg expression in best individual | |
|---|---|---|---|
| Construct | mRNA vs protein | leaf tissue (%) | tuber tissue (μg/g) |
| HB102 | 0.001 | 0.016 | 0.18 |
| HB103 | 0.001 | 0.023 | 0.33 |
| HB105 | 0.004 | 0.048 | 1.25 |
| HB106 | 0.004 | 0.035 | 0.8 |
| HB107 | 0.005 | 0.11 | 2.4 |
| HB110 | ND | 0 | ND |
| HB104 | 0.004 | 0.19 | 6.5 |
| HB114 | 0.005 | 0.22 | 16 |
| HB145 | ND | 0.063 | 1.1 |
| HB165 | ND | 0.021 | — |
| HB111 | ND | 0.041 | 0.33 |
| HB115 | ND | 0.13 | 2 |
| HB116 | ND | 0.176 | 2 |

Example 11

Characterization of Tubers of Transgenic Potato Line HB114–16.

This example describes experiments designed to characterize the recombinant HBsAg produced in tubers of potato "FL1607" line HB114–16, which is transformed with pHB114. These data indicate that HBsAg produced in these tubers has the structure expected for an immunogenic vaccine protein, comparable to the yeast recombinant HBsAg used for the commercial vaccine. Specifically, the assembled virus-like particle (VLP) form of HBsAg is more stable and immunogenic than unassembled subunits, and is thus considered a crucial characteristic of the vaccine antigen.

Figure 13:
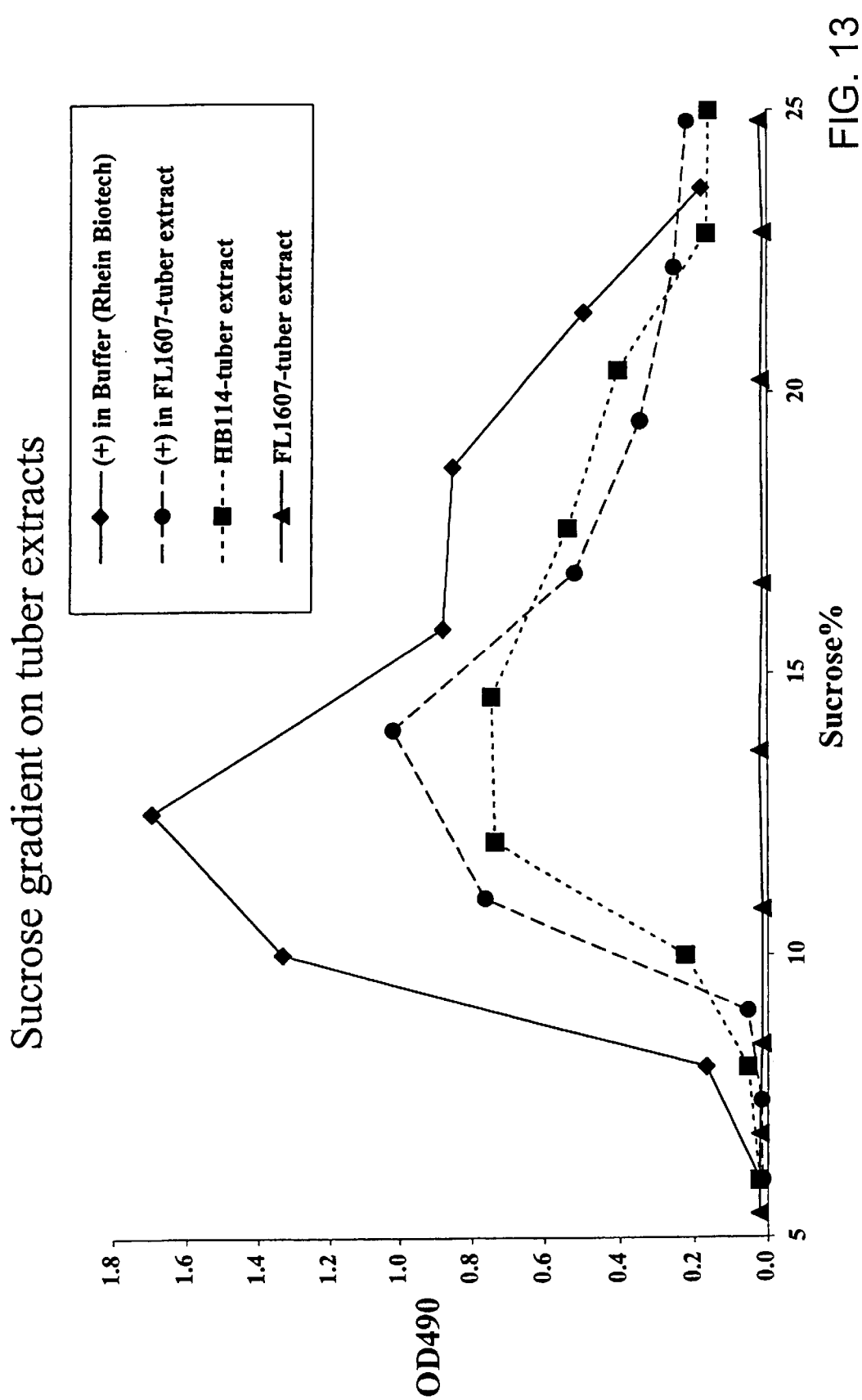

VLP Content by Sucrose Gradient. We examined extracts from HB114–16 tubers and control nontransgenic tubers by sucrose gradient sedimentation to determine whether HBsAg aggregated as VLPs as described for tobacco expression (Mason et al. 1992). A crude extract of a tuber was obtained by powdering a tuber in liquid nitrogen in a blender, then adding two volumes by weight of 1×PBS (pH 7.2), 0.1% Triton X-100, 10 mM EDTA. The buffer froze upon mixing with the frozen powder and was allowed to slowly thaw upon ice. The resuspended extract was centrifuged at 14,000 ×g for 5 min at 4° C., and 0.5 ml of the supernatant was layered above a 5–30% linear sucrose gradient in 10 mM sodium phosphate pH 7.0, 0.15 M NaCl. Gradients containing 2 μg purified yeast-derived recombinant HBsAg (rHBsAg) particles in 0.5 ml of 1×PBS (pH 7.2), 0.1% Triton X-100, 10 mM EDTA either with or without FL1607 tuber extract were run at the same time for comparison. The gradients were centrifuged in the Beckman SW41 rotor at 33,000 rpm for 5 h at 4° C. ELISA for HBsAg (Auszyme monoclonal, Abbott Laboratories) was performed on gradient fractions, and the % sucrose plotted vs. the ELISA OD. FIG. 13 shows that all HBsAg samples sedimented in a rather broad peak between approximately 8% and 22% sucrose. The profile for the tuber material is shifted slightly toward higher density, but in all samples the greatest proportion of HBsAg sediments between 10 and 15% sucrose. Yeast rHBsAg added to an extract of nontransgenic FL1607 tubers showed a profile similar to purified yeast rHBsAg, but the ELISA signals were somewhat lower. Nontransgenic FL1607 tubers showed no ELISA signals on the gradient. These data show that the tuber-derived HBsAg co-sediments with yeast-derived HBsAg, and suggest that the tuber-derived HBsAg assembles as VLPs.

Figure 14A:
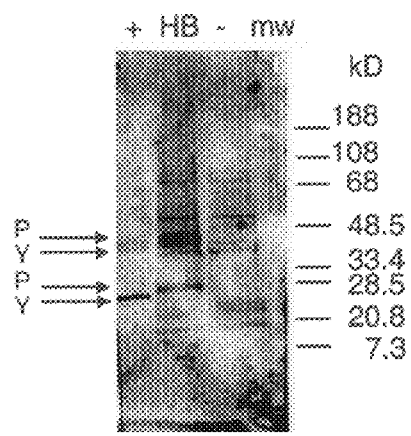
Figure 14B:
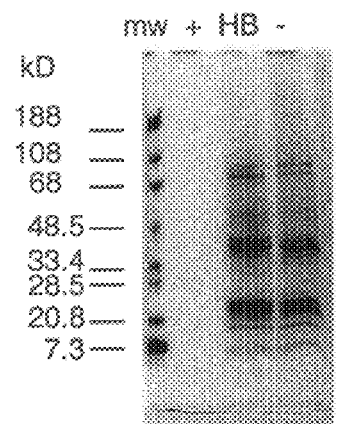

Western Blot. We performed a Western blot to observe HBsAg polypeptides in HB114–16 tubers that react with antibodies. Samples were denatured in reducing SDS-PAGE sample buffer (100 mM DTT, 2% SDS,) by boiling 5 minutes, electrophoresed, blotted to PVDF membrane and probed with polyclonal rabbit antiserum against HBsAg. FIG. 14 shows the Western blot and a duplicate gel run at the same time stained with Coomassie. The stained gel indicates that similar amounts of total tuber protein were loaded for both HB114–16 (lane HB) and nontransgenic FL1607 (lane−) samples. On the Western blot, the 10 ng of yeast-derived rHBsAg (lane+) yielded a monomer of about 25 kDa as expected and a dimer at $M_r$ about 40 kDa (bands marked "Y" at left). The tuber-derived material (lane HB) contains a monomer of about 28 kDa and larger bands that may represent dimers (bands marked "P" at left). The tuber-derived monomer is likely glycosylated and therefore of a larger size than the yeast-derived monomer. In nontransgenic tubers (lane−) several faint nonspecific bands showed, but did not cross-react in the region of monomer and dimer. Interestingly, the relative proportion of dimers to monomers in the tuber material is much higher than that for yeast rHBsAg. Although this analysis was performed under reducing conditions, the substantial proportion of dimers in tuber material indicates that it is more highly and stably disulfide crosslinked, and thus potentially more resistant to degradation, especially when delivered orally.

A Northern blot was performed on total RNA prepared from tubers of potato line HB114–16 as described (Mason et al., 1996). As a negative control, RNA from tubers of nontransgenic potato line FL1607 was examined. Five μg of each sample were denatured with formaldehyde in MOPS/acetate/EDTA buffer at 65° C. for 15 min, electrophoresed on a 1% agarose gel, and transferred to ZetaProbe membrane (BioRad) by capillary blotting. The membrane was fixed by UV irradiation in a Stratalinker (Stratagene) and then was stained with methylene blue to verify RNA integrity and loading density. A probe was prepared using random primed labeling of a 700 bp DNA fragment (comprising the HBsAg coding sequence) obtained by digesting pHB114 with NcoI and SacI. The blot was hybridized with the probe at 65° C. in 0.25 M sodium phosphate, pH 7.2; 7% SDS; 1 mM EDTA for 16 h. The membrane was washed with wash buffer 1 (40 mM sodium phosphate, pH 7.2; 1 mM EDTA; 5% SDS) 2 times for 30 minutes each at 65° C. The membrane was wrapped in plastic, and quantitatively imaged with a PhosphorImager (Molecular Dynamics).

Figure 15A:
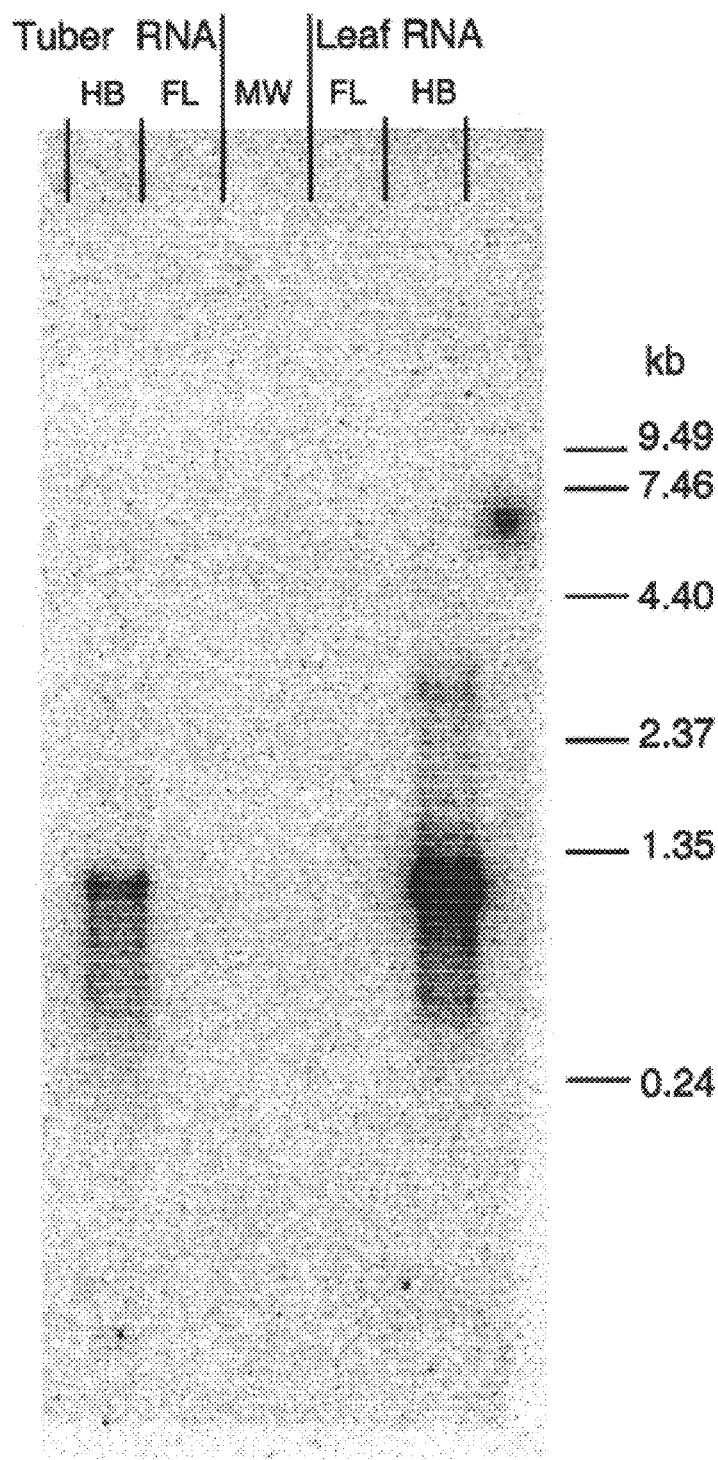
Figure 15B:
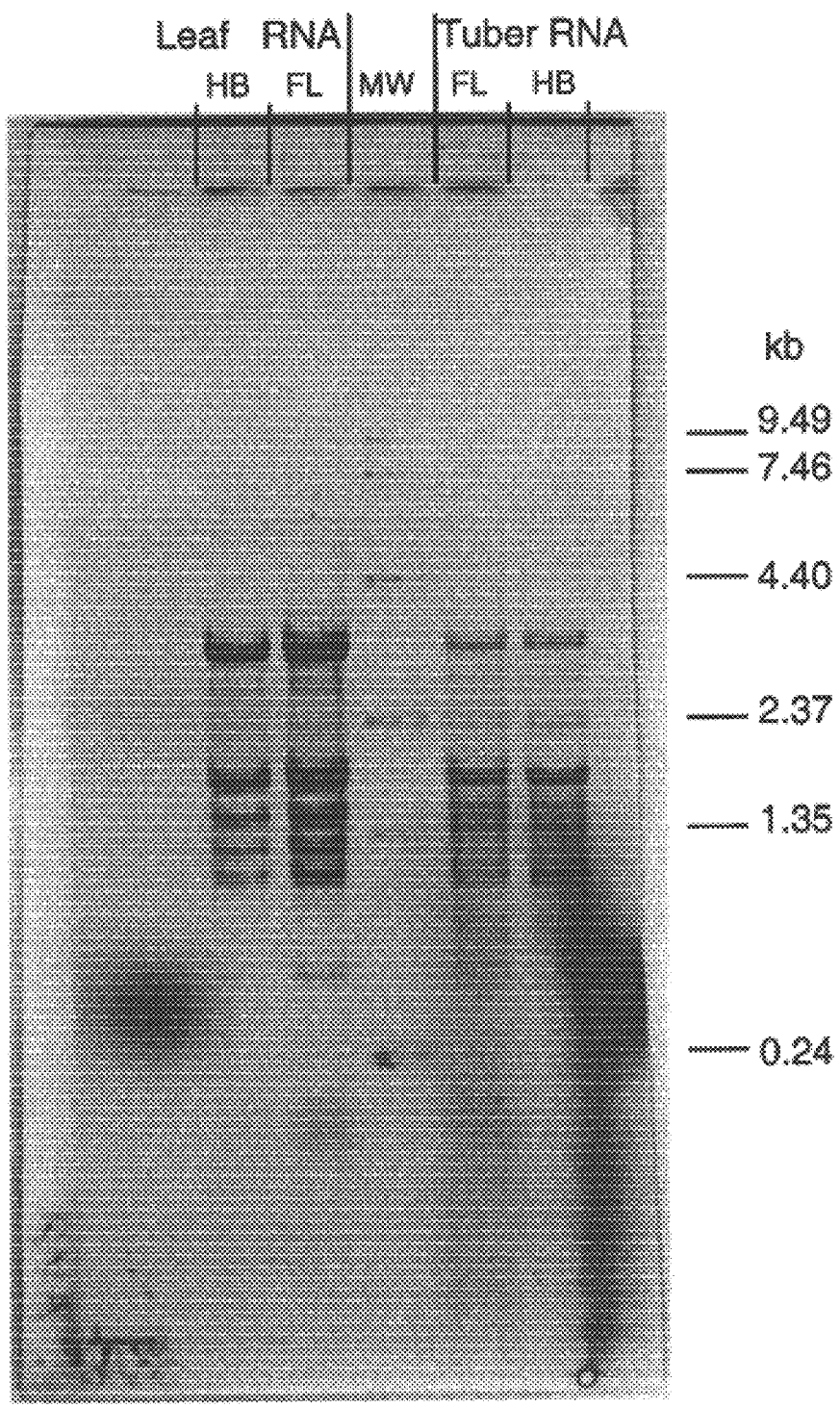

FIG. 15 shows the results obtained. Duplicate lanes were run containing the same amount of each RNA sample; one set of lanes was methylene blue stained after blotting. The photograph at right shows the methylene blue-stained blot of half of the gel, which indicates that more total RNA from leaf samples were loaded than from tuber samples. The quality of the RNA is good as judged by integrity of the ribosomal RNA bands. The photograph at the left shows the hybridization pattern obtained. HB114–16 RNA has one major band at approximately 1 kb in both the tuber and leaf samples representing the full-length HBsAg transcript. The smear underneath the 1 kb band may represent degraded RNA. The faint band at approximately 3 kb in the leaf RNA sample may represent readthrough transcription of the HBsAg unit due to a novel insertion site. Neither nontransgenic FL1607 tuber nor leaf RNAs showed hybridization signals.

Figure 16:
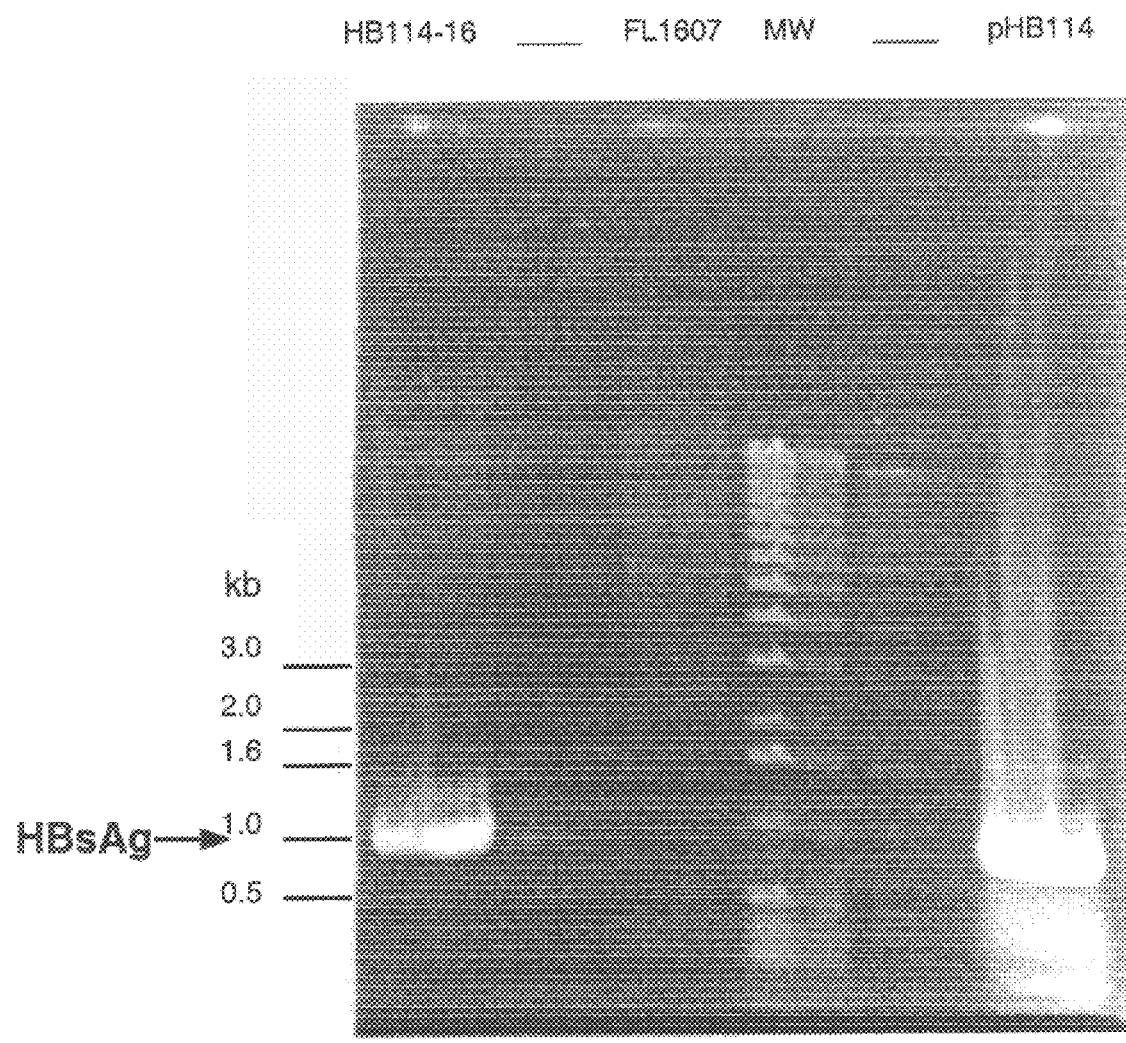

PCR analysis was performed on genomic DNA isolated from HB114–16 leaves. FIG. 16 shows a single major band was obtained using primers TEV (5'-GCATTCTACTTCTATTGCAGC) (SEQ ID NO:23) and PIN2 flanking the HBsAg gene at 5' and 3' ends, respectively. This band was the same size as that amplified from the plasmid pHB114 and was not visible in the control FL1607 genomic DNA. The PCR fragment was excised from the gel and sequenced to verify that there were no mutations from the pHB114 sequence. The sequences were identical. This shows there was no mutation or change in the HBsAg gene upon transforming the HB114–16 line.

Figure 17A:
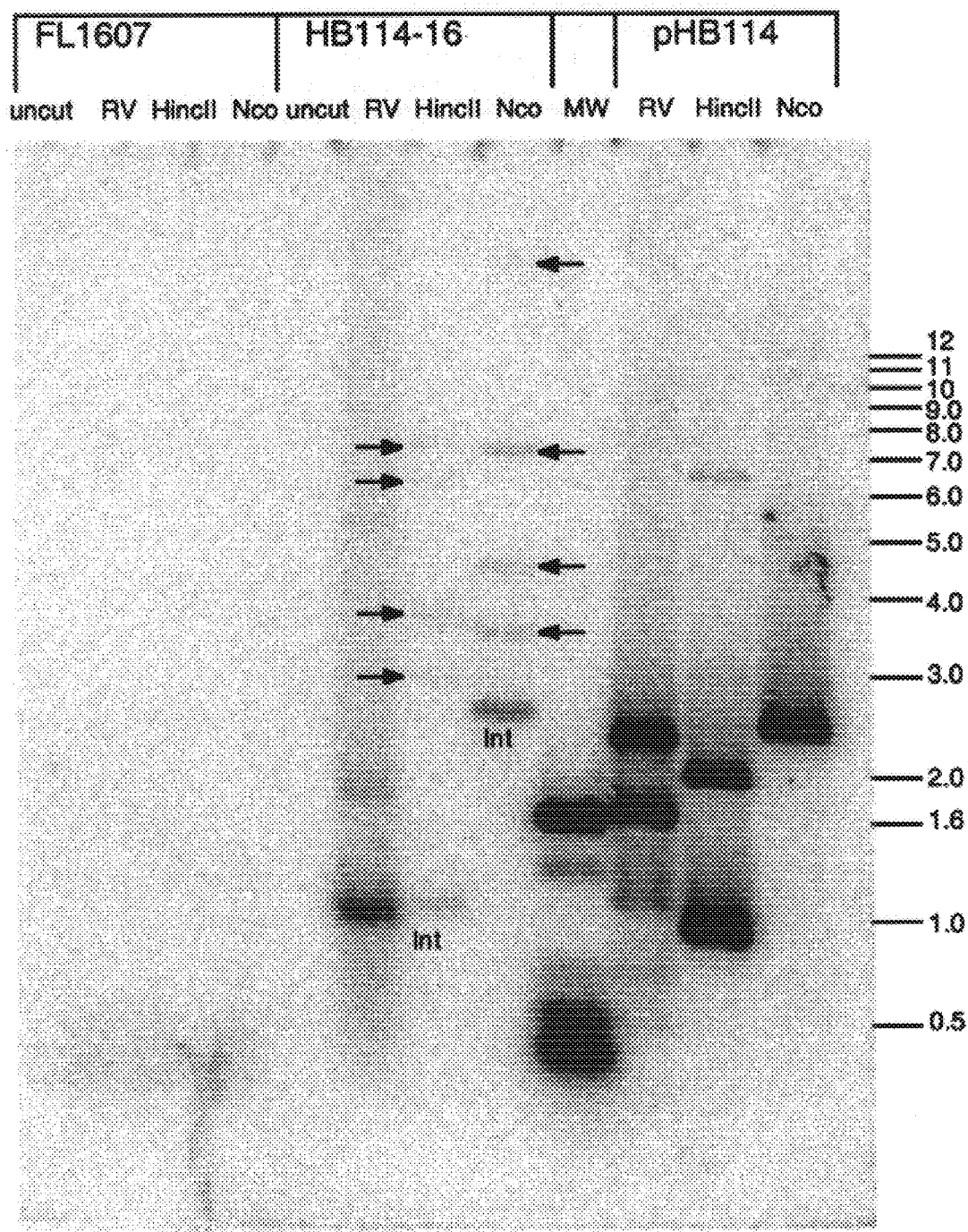
Figure 17B:
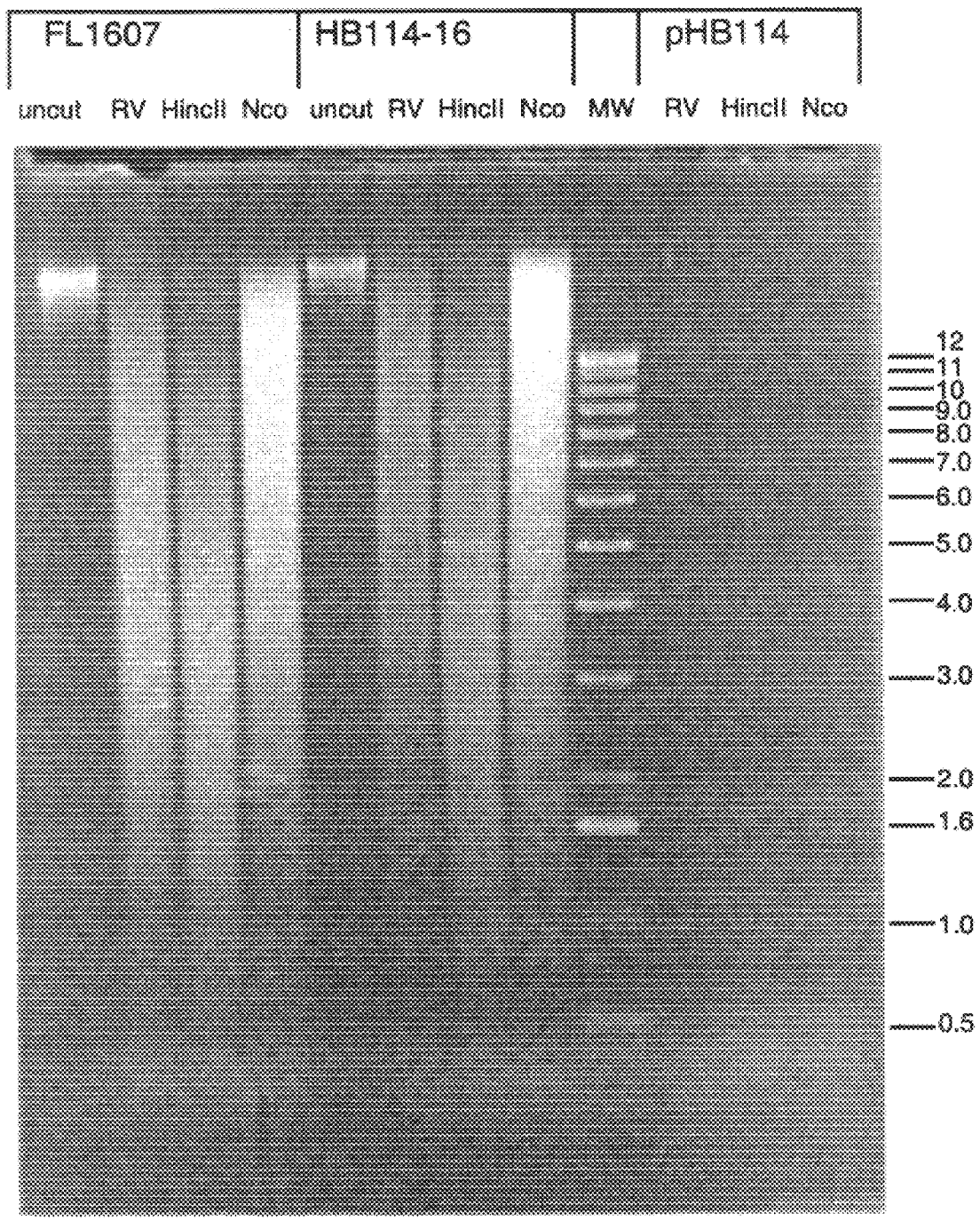
Figure 17C:
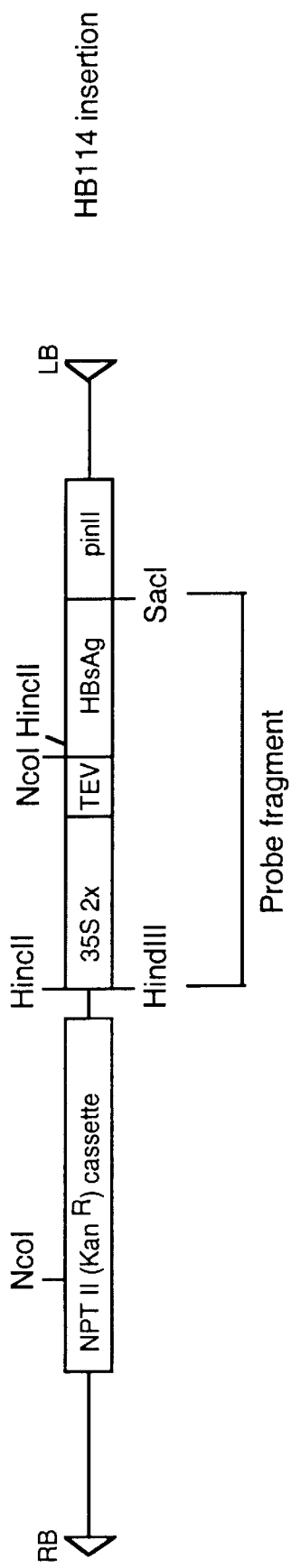
Figure 18:
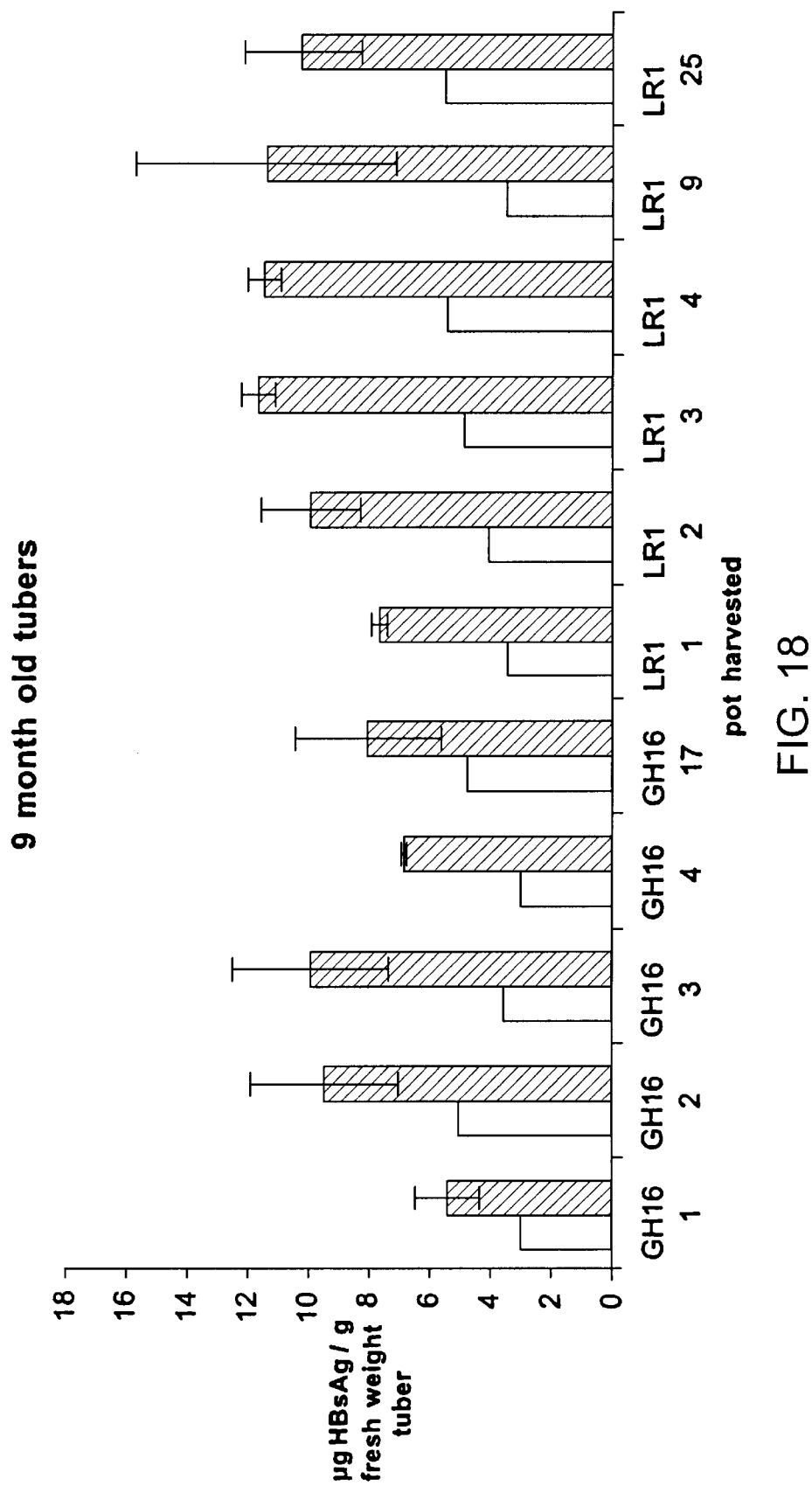

A Southern blot was performed on the same genomic DNA samples used for PCR analysis. Fifteen μg of each DNA sample, and 10 ng of pHB114 plasmid were digested with various restriction enzymes or left undigested before fractionation on a 0.8% agarose gel, depurination by treatment with HCl, neutralization, and transfer to ZetaProbe membrane (BioRad) by capillary blotting. The membrane was fixed by UV irradiation in a Stratalinker (Stratagene). A probe was prepared using random primed labeling of a 2 kb DNA fragment (comprising the S35 promoter, TEV 5-UTR and the HBsAg coding sequence) obtained by digesting pHB203 with HindIII and SacI. The blot was hybridized with the probe at 65° C. in 0.25 M sodium phosphate, pH 7.2; 7% SDS; 1 mM EDTA for 16 h. The membrane was washed with wash buffer 1 (40 mM sodium phosphate, pH 7.2; 1 mM EDTA; 5% SDS) 2 times for 30 minutes each at 65° C. The membrane was wrapped in plastic, and quantitatively imaged with a PhosphorImager (Molecular Dynamics). FIG. 17 shows the resulting pattern of hybridization, the ethidium bromide stain of the gel before transfer to Zetaprobe, a map of the T-DNA cassette, and the part of the DNA used as the probe. The digests NcoI and HincII result in a fragment internal to the T-DNA cassette that hybridize to the probe (INT) as well as another fragment that extends into the insertion site of the T-DNA. In the HB114–16 lanes digested with NcoI or HincII, at least four bands other than the internal band can be counted (see numbers to right of lane "Nco" and to left of lane "HincII"). The most likely explanation of these data is that there are at least 4 copies of the T-DNA containing the HBsAg expression cassette integrated at different sites in HB114–16 nuclear genomic DNA (see numbers on bands). The lanes containing FL1607 DNA did not hybridize to the probe. The EcoRV digest yielded unexpected results, perhaps due to partial digestion or star activity, and was thus ignored.

Stability of the HBsAg in Tubers Stored 9 Months. Several pots of HB114–16 tubers were harvested in May 1998. The tubers were stored at 4° C. in separate paper bags for each pot. One tuber from each of 11 pots was assayed by ELISA for HBsAg (Auszyme monoclonal, Abbott Laboratories) within two weeks of the harvest. Nine months later, two tubers from the same 11 pots were assayed. The bar graph in FIG. 18 shows the amount of HBsAg measured in May 1998 with black bars and the amount measured in February 1999 in white bars. The tubers had significantly more HBsAg after aging for nine months, based on tuber fresh weight. This may be explained by partial dehydration of the tubers such that the weight of a tuber is lower after storage than when it is first harvested. Another explanation may be that some HBsAg is present at harvest as improperly folded monomer subunits, and that during storage these subunits fold correctly and assemble to form VLPs, thus allowing more of the HBsAg to be detected. Finally, it is possible that further synthesis of monomers occurred during storage and that these assembled into forms detectable by the ELISA. (It is known that potato tuber cells are physiologically active during storage at 4° C., as evidenced by changes in starch and sugar content, and ultimately sprouting of the eyes and growth of shoots.) These data show that the HBsAg produced in transgenic tubers is stable for at least nine months upon storage at 4° C.

Example 12

Expression of Modified Versions of HBsAg in Tobacco Cells and Analysis of Disulfide Crosslinking This example describes the stable expression in transgenic tobacco NT1 cells of the synthetic plant-optimized HBsAg gene modified in different ways for subcellular targeting. These studies show that certain modifications cause a significantly greater extent of crosslinking of monomers via disulfide bridges. Since more highly crosslinked HBsAg is potentially more stable and more immunogenic, an enhancement of crosslinking is expected to yield a better vaccine antigen. Further, since yeast-derived recombinant HBsAg (rHBsag) is not highly crosslinked unless extracted and treated with chemicals that drive disulfide bridge formation (Wampler, D., Lehman, E., Boger, J., McAleer, W. & Scolnick, E. Multiple chemical forms of the hepatitis B surface antigen produced in yeast. Proc Nat Acad of Sci, USA 1985; 82, 6830–6834), the plant-derived HBsAg represents a potentially more immunogenic material when delivered orally without purification and/or chemical treatment.

We created transgenic tobacco NT1 cell lines by Agrobacterium-mediated DNA delivery with plasmids pHB117, pHB118, pHB119, pHB121, pHB122, and pHB123. These constructs are described more fully in Example 7, but we briefly describe their modifications in Table 3 below. All contain the synthetic plant-optimized HBsAg gene described in Example 7, which has been modified here by either a N- or C-terminal extension, or both. Our rationale suggests that a N-terminal plant signal peptide may more effectively target the nascent HBsAg polypeptide to the ER and allow more efficient folding of monomers and assembly of crosslinked virus-like particles (VLPs). The αS signal peptide contains 21 amino acids, while the αLsignal peptide comprises an additional 14 residues from the same soybean vspA gene that contains a potential vacuolar localization signal (Mason et al. 1988). Further, a C-terminal ER retention signal "SEKDEL" (SEQ ID NO:4) may concentrate the subunits in the ER by salvage from downstream endomembrane compartments, and thereby drive more effective association and crosslinking of monomers.

TABLE 3

Plasmids used in this Example

| Name | N-terminal extension | C-terminal extension |
|---|---|---|
| pHB117 | None | None |
| pHB118 | vspA αS signal peptide | None |
| pHB119 | vspA αL signal peptide | None |
| pHB121 | None | SEKDEL |
| pHB122 | vspA αS signal peptide | SEKDEL |
| pHB123 | vspA αL signal peptide | SEKDEL |

We used these plasmids to transform tobacco NT1 cells essentially as described (Newman T C, Ohme-Takagi M, Taylor C B, Green P J. DST sequences, highly conserved among plant SAUR genes, target reporter transcripts for rapid decay in tobacco. Plant Cell 1993; 5:701–714). Callus cell colonies selected for growth on 300 mg/L kanamycin were assayed for expression of HBsAg. Cells were extracted with 2 ml per g cells in buffer (PBS, pH 7.2; 50 mM sodium ascorbate, 10 mM EDTA, 0.2 mM PMSF, 0.1% Triton-X-100). Extracts were clarified by centrifugation at 16,000 ×g for 3 min at 4° C., and supernatants tested for total soluble protein (TSP) by Bradford assay (BioRad) and for HBsAg by Auszyme monoclonal ELISA (Abbott Laboratories). Expression varied greatly among the lines, but the lines that expressed the highest levels for each construct were propagated and used for further study. Table 4 below shows expression data from a representative experiment in which a selected line from each construct were assayed. All lines expressed similar levels of TSP. All of the modified forms were expressed to higher levels of HBsAg than the unmodified form in line HB117–9, with line HB118–3 giving the highest level. We must interpret the data with caution, since we did not quantify mRNA levels, which would have accounted for some differences. However, these lines were selected as the best lines from 20 random events for each transformation experiment, and thus it is likely that the modified forms perform at least as well as the unmodified HBsAg.

TABLE 4

HBsAg and total protein in transgenic NT1 cell lines

| Line | TSP (mg/ml) | HBsAg (ng/mg TSP) |
|---|---|---|
| HB117-9 | 4.78 | 67 |
| HB118-3 | 4.28 | 261 |
| HB119-5 | 3.88 | 121 |
| HB121-11 | 3.40 | 118 |
| HB122-8 | 4.80 | 133 |
| HB123-1 | 4.46 | 155 |
| NT1 control | 3.12 | 0 |

Immunoprecipitation and Analysis of Crosslinking

We examined the NT1 cell extracts for multimeric forms of HBsAg by Western blot after fractionation of immunoprecipitates under partial reducing conditions. Cells were extracted and assayed as above for TSP and HBsAg. Samples containing 1 mg TSP were diluted 10-fold with PBS containing 1% Triton-x-100, 0.5% sodium deoxycholate, and 0.1% SDS, then mixed with 1 µg of goat anti-HBsAg (Fitzgerald Industries, Concord, Mass.). The reaction was incubated for 1 h at 23° C., and then mixed with 15 µl Protein G Plus-Agarose (Calbiochem) and incubated on a rotating mixer at 4° C. for 16 h. The agarose matrix was pelleted and washed according to the supplier's instructions before suspending in 25 µl of 1.5×SDS-PAGE sample buffer containing 80 mM DTT. Samples of yeast rHBsAg were immunoprecipitated in the same way.

Figure 19A:
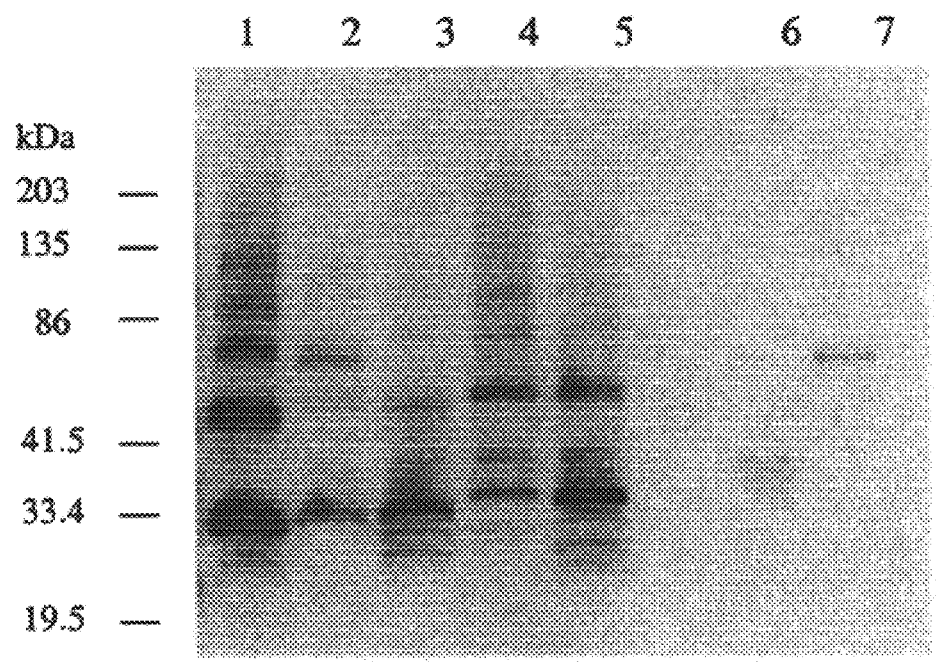
Figure 19B:
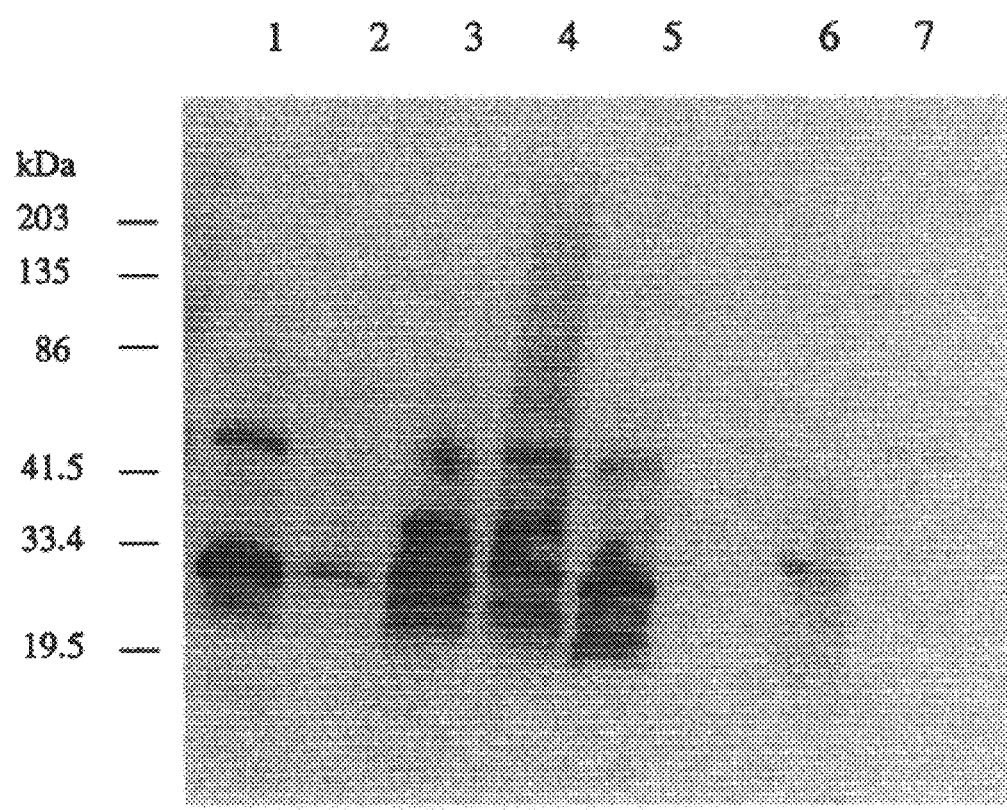

In Experiment 1, samples from lines HB117-9, HB118-3, and HB121-11 were examined. The immunoprecipitated (IP) samples in SDS-PAGE sample buffer were heated at 50° C. for 5 min (partial reducing condition), centrifuged 16,000 ×g for 2 min, and 10 µl of supernatant loaded on a 4–20% gradient minigel (BioRad). The remaining material was resuspended and heated at 100° C. for 20 min (stringent reducing condition), centrifuged 16,000 ×g for 2 min, and 10 µl of supernatant loaded on a second gel. Samples were electrophoresed, electroblotted to PVDF membranes, and probed with the same goat anti-HBsAg serum used for IP. FIG. 19 shows the Western blots obtained. Panel A shows samples that were subjected to partial reducing condition (50° C. for 5 min), and panel B shows samples given stringent condition (100° C. for 20 min). Yeast rHBsAg (50 ng) in lanes 1 shows a ladder of multimers under partial reduction, which is much less pronounced under stringent reduction. Similar patterns are seen for the yeast rHBsAg purified by IP (lanes 2), although the recovery yield was less than expected. Note that all lanes contain a signal at approximately 50 kDa that represents the heavy chain of the goat IgG that was used both as the IP hook and the Western blot probe, and included in lanes 7 as control. The HBsAg dimer and trimer signals bracket this signal and are well resolved from it. The HBsAg monomer in sample HB117-9 (unmodified HBsAg) co-migrates with the yeast rHBsAg monomer, and is present with dimer and faint multimer signals under partial reduction. This indicates that HBsAg readily crosslinks to form multimers when expressed in plant cells. Even under stringent reduction, a strong dimer signal is evident in sample HB117-9. A pair of faint lower $M_r$ signals is seen in the HB117-9 sample that is not present in the yeast-derived material, suggesting a single cleavage event that yields 2 HBsAg fragments. Further study is needed to determine whether this cleavage occurs in the living cells or as a result of extraction. The nontransgenic NT1 cell sample (lanes 6) shows a faint nonspecific signal that runs between the HBsAg monomer and dimer and is well resolved from both.

Lanes 4 contain NT1 cell sample HB118-3 with the HBsAg modified with the N-terminal "αS" plant signal peptide extension. The monomer signal in this sample runs at slightly higher $M_r$, which suggests that the plant signal peptide is not cleaved in these NT1 cells. Most interestingly, the dimer signal in partially reduced sample HB118-3 is more intense than the monomer, and multimers up to a pentamer can be distinguished, with a smear upwards indicating substantially higher-order multimers are present. Even with stringent reducing condition, the trimer and tetramer signals are easily distinguished, showing that the disulfide crosslinks between monomers are quite stable and resistant to reduction in HB1118-3 cells. Like sample HB117-9, 2 faint lower $M_T$ signals suggest a partial proteolytic cleavage.

Lanes 5 in Experiment 1 contain samples from NT1 cell line HB121-11 with the HBsAg modified by the C-terminal extension "SEKDEL" (SEQ ID NO:4). The partially reduced sample shows a monomer that runs at slightly higher $M_r$, which is consistent with the C-terminal extension. Further, multimers up to tetramer are easily observed showing substantially greater degree of crosslinking than in the HB117-3 cells. Stringent reduction converts most multimers to monomers, but a strong dimer signal is still present. Like HB117 and HB118 lines, 2 faint lower $M_r$ signals suggest a partial proteolytic cleavage in sample HB121.

Figure 20A:
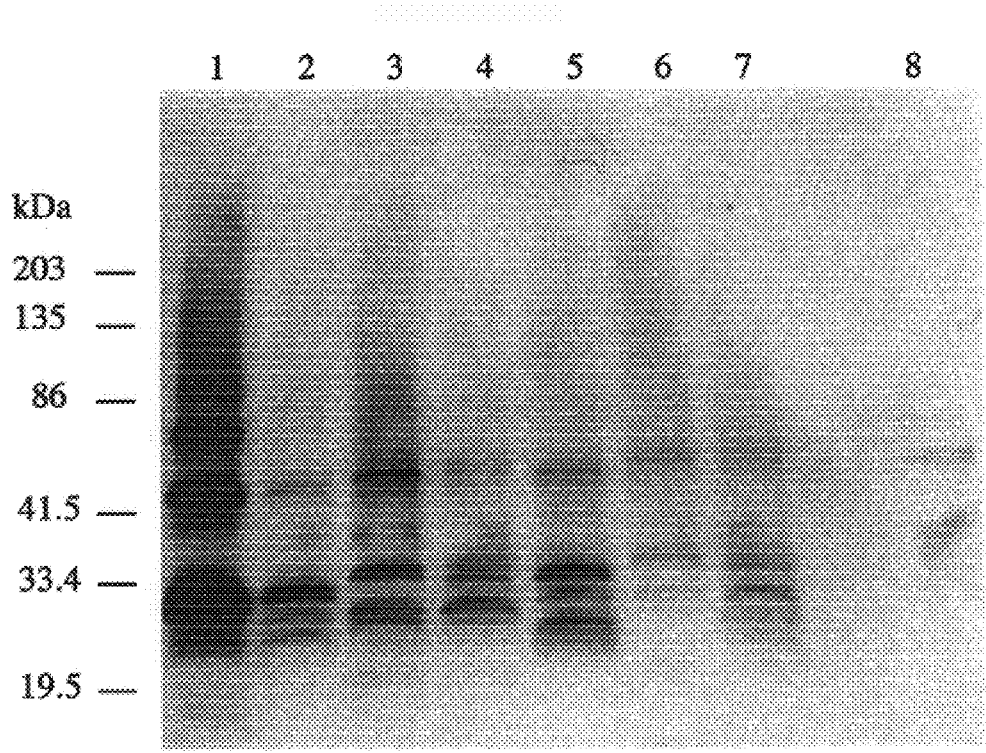
Figure 20B:
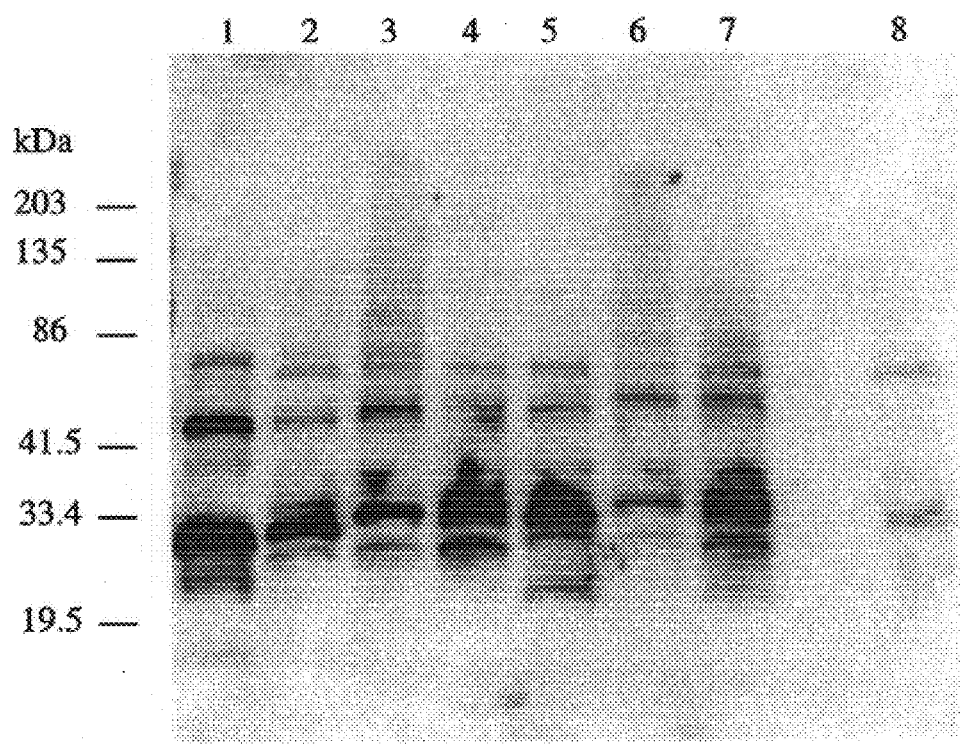

In Experiment 2, samples from all 6 transgenic lines were examined. In this case, separate IP reactions were performed for the partial reduction (50° C.×5 min) and stringent reduction (100° C.×20 min), in order to obtain a more quantitative result. FIG. 20 shows the results; again Panel A samples are partially reduced and Panel B samples are stringently reduced. Samples HB117-9, HB118-3, and HB121-11 show results consistent with Experiment 1, although the resolution of higher-order multimers is less defined under partial reduction. The HB118-3 sample in Panel B (stringent reduction) again shows highly resistant crosslinking with tetramers evident and higher-order multimers likely in the smear at higher $M_r$.

Lanes 4 in Experiment 2 contain NT1 cell sample HB118-3 with the HBsAg modified with the N-terminal "αL" plant signal peptide extension. In Panel A signal peptide-processed monomer is apparent in approximately equimolar ratio with a larger signal that likely represents the unprocessed form. Multimers are also present, which are largely shifted to monomers and dimers in the stringent reducing condition.

Lanes 6 and 7 contain samples HB122-8 and HB123-1, respectively, in which the HBsAg is extended on both N- and C-termini. In these samples (Panel B), tetramers are evident even under stringent reducing condition. Line HB123-1, which carries the "αL" plant signal peptide extension and the C-terminal SEKDEL (SEQ ID NO:4) extension, showed apparent partial processing of the signal peptide, like line HB119-5 that carries the "αL" plant signal peptide alone. Thus it appears that the longer "αL" signal peptide is more efficiently processed than the shorter "αS" signal peptide in these NT1 cells.

In conclusion, HBsAg expressed in cultured tobacco NT1 cells readily forms disulfide-crosslinked multimers. Crosslinking is greatly enhanced when either "αS" or "αL" forms of the soybean vspA signal peptide is fused to the N-terminus of the Plant-optimized HBsAg gene. These data indicate that plant-produced HBsAg, especially when fuised to a plant signal peptide, is a superior vaccine antigen for use in oral delivery of crude or unprocessed host material.

Example 13

Expression of Oral Adjuvant in Potato

The *E. coli* LT B subunit can be expressed in potato tubers in a form that is immunogenic when fed directly to mice without preparation other than slicing, with the amino acid sequence SEKDEL (SEQ ID NO:4) increasing expression (Haq, T. et al. 1995). As mentioned herein the LT-B protein can be used as a vaccine carrier. Expression of the LT-B protein can be greatly enhanced still further by employing plant-optimized codons of the coding sequence of the protein. The differential expression levels are shown in Table 5.

TABLE 5

| Coding region (plasmid) | Modification(s) | LT-B, ng/mg total soluble protein |
|---|---|---|
| Native LT-B (pLTB110) | Optimize translation start site | 70 |
| LTB-SEKDEL (pLTK110) | C-terminal SEKDEL extension | 190 |
| Synthetic LT-B (pTH110)* | Plant-optimized codons, eliminate spurious polyadenylation and splicing signals | 4640 |

*Construction of pTH110 is described in Mason, H., et al. (1998)m Vaccine, 16: 1336–1343.

*Construction of pTH110 is described in Mason, H., et al. (1998), Vaccine, 16: 1336–1343.

Example 14

Transgenic Potato Plants that Coexpress HBsAg and Mucosal Adjuvant *E. coli* Mutant LT in Tubers In order to avoid the logistical problems involved in mixing and stabilizing preparations containing vaccine antigen and adjuvant, it is convenient to provide edible material having both components without need for preparation. To this end, transgenic potato plants, which coexpress and accumulate HBsAg and *E. coli* mutant LT in their tubers, can be produced.

Plasmid vectors permitting the co-expression in plants of A and B subunits of *E. coli* heat labile enterotoxin (LT) and mutants thereof have been constructed. These are also the subject of co-pending application U.S. Ser. No. 60/113,507. In order to co-express HBsAg with LT in potato plants, a potato plant is transformed with a plasmid used as a host for transformation with a binary vector that contains an HBsAg expression cassette and confers antibiotic resistance. An example of the former plasmid is pSLT102, which expresses assembled LT-K63 (S62 to K63 mutation in LT-A) and carries the kanamycin-resistance NPT-II gene. Examples of suitable plasmids for preparing a vector having antibiotic resistance are pGPTV-HYG (hygromycin) and pGPTV-BAR (phosphinothricin) (Becker, D. et al. 1992). The desired plasmid is constructed by digestion of pHB117 with HindIII and EcoRI to obtain the HBsAg cassette, and ligation with pGPTV-HYG or pGPTV-BAR digested likewise. The resulting binary vector is then used to transform the host LT-K63-expressing potato line using selection on media containing 20 mg/L hygromycin or 1 mg/L phosphinothricin.

Example 15

Oral immunization of Mice with HBsAg Expressed in Potato Tubers

BALB/c mice are fed potato slices (5 g potato/feed/animal) expressing HBsAg. As shown in FIG. 3, the mice developed serum IgM and IgG responses that are specific to HBsAg. A group of control animals fed non-transforrned potatoes failed to generate antibodies. Cholera toxin (Sigma, St. Louis, Mo.) was used as an oral adjuvant in these studies. Ten μg of adjuvant is placed on the potato slices and consumed by the animals along with the antigen. This experiment was repeated twice with a total of 10 mice in both the experimental and control groups. The potato tubers in these experiments expressed only 1.1 μg HBsAg/gm potato. Therefore, each animal received only 5.5 μg HBsAg per feed. This likely directly reflects the modest primary response elicited. Even so, when both groups of mice were challenged with a sub-immunogenic dose of yeast-derived rHBsAg on day 60, only those fed with the transgenic potatoes made a secondary anti-HBsAg response, confirming that a memory cell response had been established. When the immune response was analyzed in terms of immunoglobulin class and subclass, an IgM response followed by IgG response was observed in all subclasses. No serum IgA response could be measured.

Example 16

Transformation of Tomato Plants

Tomato plants can be transformed according to the protocol of Frary/Fillati et al. (1987) *Biotechnology* 5:726–730), as modified herein:

Seeds (100 seeds~380 mg.) (Tanksley TA234TM2R) are sterilized and immersed in 20% CHLOROX bleach for 20 min. The seeds are rinsed well with sterile milli-Q water (2 or more times) and sowed in Magenta boxes containing ½ MSO (approximately 30 seeds/box). One day prior to cutting cotyledons, 2 mL of a one week old NT-1 suspension culture is pipetted onto a KCMS media plate. (NT-1 cells are subcultured weekly (2:48) in KCMS liquid medium.). The suspension is covered with a sterile Whatman filter and cultured in the dark, overnight. The cotyledons are cut 8 days after sowing. Seedlings are placed on a sterile paper towel moistened with sterile water. The cotyledons are excised at the petiole and the tips cut off. They are cut in half again if size of cotyledon is greater than 1 cm. The explants are placed on feeder plates adaxial side down and cultured at 25° C., 16 hour photoperiod, overnight.

For the transformation, Agrobacterium is streaked onto LB selective media plate about 1 week prior to transformation and incubated at 30° C. Liquid selective medium is inoculated with the Agrobacterium by picking a single colony off of the streaked plate, and inoculating 3 mL YM medium with 150 μg kanamycin sulfate. The culture is vigorously shaken at 30° C. for 48 hours. One mL of the culture is inoculated into 49 mL YM medium with 2.5 mg kanamycin sulfate and cultured in a 250 mL flask shaken vigorously at 30° C. for 24 h. The optical density is measured at 600 nm. Optimum O.D. is considered to be 0.5 to 0.6.

The Agrobacterium culture is centrifuged at 8,000 rpm (Sorvall centrifuge, ss34 rotor) for 10 min. The YM is poured off and the pellet resuspended in MS-O, 2%. The final O.D. should be between 0.5 and 0.6. Twenty five mL of the Agrobacterium culture is pipetted into a sterile Magenta box. The explants are transferred from 2 to 3 plates into inoculum in a magenta box and incubated for 5 min. with occasional shaking. The explants are removed to a sterile paper towel. The explants are returned to feeder plates, adaxial side down and the plates are sealed with Nesco film. The explants are cocultivated for a 16-hour photoperiod at 25° C. for approximately 24 h. The explants are transferred to selection media (2Z) adaxial side up. The plates are sealed with micropore tape and returned to 25° C., for a 16-hour photoperiod.

The explants are transferred to new IZ selection medium plates every 3 weeks. When shoots begin to appear they are transferred to IZ Magenta boxes.

Example 17

Regeneration of Transgenic Tomatoes

Within 4 to 6 weeks initial shoots should appear. Shoots are excised from the explants when shoots are at least 2 cm and include at least 1 node. They are placed in Magenta boxes (4/box) containing Tomato Rooting Media with selective agents. Roots should begin to appear in about 2 weeks. Standard Greenhouse growth conditions are employed: 16 hour day; average temperature: 24.5° C.; fertilized each time watered: 100 ppm. EXCELL (15–5–15) with extra calcium and magnesium; potatoes grown in METRO-MIX 360; tomatoes grown in Cornell Mix +OSMO; biological controls are used whenever possible to improve overall plant quality.

Example 18

ELISA Assay for Measurement of Serum Anti-HBsAg Specific Antibodies

Mouse sera is evaluated for anti-HBsAg-specific antibodies using a commercially available AUSAB enzyme immunoassay (EIA) diagnostic kit (Abbott Diagnostics, Chicago, Ill.) using the methods described elsewhere (Pride, M. et al., 1998). Use of the AUSAB quantitation panel permits conversion of absorbance values to mIU/mL.

Example 19

Isotype Distribution of the Anti-HBsAg Response

The isotype distribution of the anti-HBsAg response is determined using the mouse typer sub-isotyping kit (Bio-Rad; Richmond, Calif.). Sera, saliva, and fecal extracts are incubated on HBsAg-coated beads (from the Abbott EIA kit) and bound antibody is detected using rabbit anti-mouse subclass-specific antiserum (Bio-Rad, enzyme immunoassay (EIA) grade Mouse Typer panel).

Example 20

Detection of CT (LT) Specific Antibody Production by ELISA

This assay is included to serve as a positive control. The systemic antibody responses obtained following the oral administration of CT/LT are well documented, and therefore allow evaluation if the responses are comparable. CT-B is assayed as described by Mason et al., 1992, 1998).

Example 21

Measurement of Antibody Responses in Mucosal Secretions

To measure antibody levels in mucosal secretions stool and saliva samples are collected as follows:

Stools: Freshly voided fecal pellets are collected from individual animals and stored in Eppendorf tubes at −70° C. Prior to the assay, pellets are resuspended in PBS (50 µL per pellet), the tubes then allowed to stand at room temperature for 15 mins, then vortexed vigorously and incubated at 20° C. for 15 min. Samples then re-vortexed, and centrifuged at 1,000 ×g for 5 min. The supernatant is collected and used immediately in an ELISA assay. This method is essentially as described by deVos & Dick. J. Immunol. Methods. 141:285–288(1991).

Saliva: Saliva is collected in capillary tubes following i.p. injection of mice with 0.1 mL of a 1 mg/mL solution of pilocarpine. Care is taken to collect the first flush of saliva in all cases. Samples are transferred to Eppendorf tubes and stored at −70° C. until assayed.

Example 22

Preparation of single-cell Suspensions

Single-cell suspensions are obtained from spleens by gently teasing the tissue through a sterile stainless steel screen. Peyer's Patches (PP) lymphoid cells are isolated by excising the PP from the small intestine wall. Cells are dissociated in Joklik's modified medium (GIBCO, Grand Island, N.Y.) containing 1.5 mg of the neutral protease enzyme Dispase (Boehringer Mannheim Biochemicals, Indianapolis, Ind.) per mL or 0.5 mg/mL collagenase as described previously (Kiyono, H. et al. PNAS USA 79:596–600 (1982)).

Example 23

B cell ELISPOT

This assay is performed using cells isolated as described above from the spleen and Peyer's Patches allowing for comparison of the responses seen in systemic (spleen), and mucosal induction (Peyer's Patches). Antigen-specific and total IgM, IgA, and IgG spot-forming cells (SFC) are enumerated in cell suspensions by antigen-specific ELISPOT as described elsewhere (see, e.g., Current Protocols in Immunology).

Example 24

Analysis of Th1 and Th2 Cells in Murine Systemic and gut-associated Tissues Following Oral Ingestion of Transgenic Potatoes The nature and kinetics of the T cell response generated as a consequence of feeding mice transgenic plants expressing HBsAg or any immunogenic polypeptide can be examined. Using T cells enriched from the spleen or Peyer's Patches of mice immunized orally with a synthetic microencapsulated peptide elicited antigen-specific T cell proliferative responses. Similar studies can be performed in mice fed the transgenic potatoes.

The frequency of Th1 and Th2 type cells in both systemic and mucosa-associated tissues of mice fed transgenic HIBsAg expressing plants can also be analyzed. The frequency of Th1 or Th2 cells in mucosal tissues such as Peyer's Patches could influence the isotype specific responses that occur. Three approaches can be taken: (i) cytokine-specific single cell assays to quantitate the number of antigen-specific cells secreting a particular cytokine, (ii) measurement of secreted cytokines using specific ELISA assays, and (iii) cytokine specific PCR analysis. The first two approaches permit determining the level of synthesis and secretion of the various cytokines whereas the third approach will determine if these are concomitant changes in mRNA production. The combination of these approaches will allow determination if an increase in a particular cytokine is a direct consequence of increase in cytokine mRNA expression.

In Vitro Proliferation of Splenic and Peyer's Patches T Cells. One week after the third feeding the animals are sacrificed, the spleen collected, and the cells purified as described previously (Pride, M. et al. 1993). The Peyer's Patches are collected and cells dissociated as described above. The enriched T cells ($2.5 \times 10^5$ cells per well) are plated in 96-well flat-bottomed plates along with $5 \times 10^5$ irradiated syngeneic spleen cells as a source of antigen-presenting cells. Following addition of antigen, the cells are cultured for 120 h as described. Proliferation, as measured by [$^3$H]thymidine incorporation, are determined by liquid scintillation spectroscopy. Results are expressed as the mean cpm of [$^3$H]-TdR incorporated of triplicate wells.

Enumeration of Cytokine Producing T Cells. Enumeration of cytokine producing cells within in vitro restimulated antigen-specific T cell cultures is determined by ELISPOT using matched pairs anti-cytokine monoclonal antibodies.

Cytokine Specific ELISA Assays. The amount of cytokines produced in culture supernatants of spleen cells and Peyer's Patches T cells is assessed by an ELISA (*Current Protocols in Immunology*) using the same anti-cytokine mAbs as used in the ELISPOT assays.

Cytokine-specific PCR Analysis. For the detection of IFN-γ, IL-2, IL-4, IL-5, and IL-6 specific mRNA in CD4+T cells (spleen cells and Peyer's Patches), a standard RT-PCR amplification protocol is employed and modified as previously described (Kiyono, H. et al. 1982). For the isolation of RNA, the method of acid guanidium thiocyanate phenol chloroform extraction procedure is used (Chomczynski & Sacchi, Anal. Biochem. 162:156 (1987)). RNA is extracted and then subjected to the cytokine-specific RT-PCR using 2.5 U/μL Superscript II Reverse Transcriptase (Life Technologies). PCR products separated by electrophoresis in 2% agarose gels are stained with ethidium bromide (0.5 μg/mL) and visualized under UV light.

For quantitation of IFN-γ and IL-4-specific mRNA, a RT-PCR has been adopted using recombinant mRNA (rcRNA) as internal standard. A connected rcRNA for IFN-γ, IL-4, and β-actin has been constructed as described elsewhere (Wang et al. PNAS USA 86: 9717–9721 (1989)). The PCR reaction is conducted in 50 μL of PCR buffer, 3 mM MgCl$_2$, 0.2 mM of each dNTPs, 30 pmol of mRNA forward and reverse primers for IFN-γ, IL-4, and β-actin, 200 ng genomic DNA (spacer gene) and 2.5 units Taq polymerase (Perkin-Elmer Cetus, Foster City, Calif.) at 85° C. Suitable primers are listed in Table 6. After heating at 94° C. for 3 min, samples are cycled 30 times with a 30-s denaturing step (94° C.), a second annealing process (59° C.), and a 45-s extension step (72° C.) in a thermal cycler (Perkin-Elmer Cetus). A 5-min extension step (72° C.) is performed at the end of the procedure. The PCR products are purified with the Wizard PCR Preps DNA Purification System (Promega Corp., Madison, Wiss.). After construction of this synthetic gene containing IFN-γ, IL-4, and β-actin, the PCR product is inserted into a pGEM-T Vector containing the T7 polymerase promotor (Promega). Transformation is performed by using *Escherichia coli* JM109. To obtain rcRNA, a purified synthetic gene is linearized by SpeI (Promega). To obtain purified rcRNA, the transcripts are treated with RQIDNase (Promega) and then further purified by using Oligotex-dT latex particles (Oligotex-dT mRNA kits, Qiagen, Chatsworth, Calif.).

TABLE 6

List of primers for specific PCR cytokine

| | | |
|---|---|---|
| β-Actin (349bp): | 5' Primer | 5'-TGGAATCCTGTGGCATCCATGAAAC-3'(SEQ ID NO:24) |
| | 3' Primer | 5'-TAAAACGCAGCTCAGTAACAGTCCG-3'(SEQ ID NO:25) |
| IFN-γ(460bp): | 5' Primer | 5'-TGA ACG CTA CAC ACT GCA TCT TGG-3 (SEQ ID NO:26) |
| | 3' Primer | 5'-CGA CTC CTT TTC CGC TTC CTG AG-3'(SEQ ID NO:27) |
| IL-2(502bp): | 5' Primer | 5'-ATG TAC AGC ATG CAG CTC GCA TC-3'(SEQ ID NO:28) |
| | 3' Primer | 5'-GGC TGG TTG AGA TGA TGC TTT GAC A-3'(SEQ ID NO:29) |
| IL-4 (399bp): | 5' Primer | 5'-ATG GGT CTC AAC CCC CAG GAA GTC-3' (SEQ ID NO:30) |
| | 3' Primer | 5'-GCT CTT TAG GCT TTC CAG GAA GTC-3'(SEQ ID NO:31) |
| IL-5 (243bp): | 5' Primer | 5'-ATG ACT GTG CCT CTG TGC CTG GAG C-3'(SEQ ID NO:32) |
| | 3' Primer | 5'-CTG TTT TTC CTG GAG TAA ACT GGG G-3'(SEQ ID NO:33) |
| IL-6(155bp): | 5' Primer | 5'-CTG TTT TTC CTG GAG TAA ACT GGG G-3'(SEQ ID NO:34) |
| | 3' Primer | 5'-5'-TCT GAC CAC AGT GAG GAA TGT CCA C-3'(SEQ ID NO:35) |
| IL-10(237bp): | 5' Primer | 5'-ACC TGG TAG AAG TGA TGC CCC AGG C-3'(SEQ ID NO:36) |
| | 3' Primer | 5'-CTA TGC AGT TGA AGA TGT CAA A-3'(SEQ ID NO:37) |
| TNF-α(354bp): | 5' Primer | 5'-TTCTGTCTACTGAACTTCGGGGTGATCGGTCC-3'(SEQ ID NO:38) |
| | 3' Primer | 5'-GTATGAGATAGCAAATCGGCTGACGGTGTGCC-3'(SEQ ID NO:39) |

For competitive RT-PCR, total RNA is run with cytokine-specific rcRNA as a competitive template. Aliquots of total RNA (8–630 ng for IFN-γ, 11–900 ng for IL-4, and 0.19–15 pg for β-actin) are spiked with a series of diluted mRNA internal standards. A standard RT-PCR is then performed (see Table 7). Quantitation is achieved by addition of 5 μCi of [$^{32}$P]dCTP (Amersham, Arlington Heights, Ill.) to the PCR reaction mixture. Duchmann et al., DNA and Cell Biol. 12:217. 1993. Finally, the PCR products are electrophoresed as described above. The [$^{32}$P]dCTP content of IFN-γ, IL-4, and β-actin-specific bands is determined by liquid scintillation counting.

TABLE 7

| RT Condition | PCR Condition | |
|---|---|---|
| 42° C. 15 min | 95° C. 2 min | 1 cycle |
| 99° C. 5 min | 95° C. 1 min 60° C. 1 min | 35 cycle |
| 5° C. 5 min | 60° C. 7 min | 1 cycle |
| | 4° C. soak | |

Example 25

Effect of Detergent Concentration on Extraction of HBsAg from Plants

A potato virus X (PVX) strain DX based plant virus vector was used to express hepatitis B surface antigen (HBsAg) in plants. The synthetic HBsAg gene, optimized for in planta expression, was amplified by polymerase chain reaction from the plasmid psHB312 described in Example 7 under pHB15, using oligonucleotide primers into which sites for the restriction enzymes ClaI and XhoI had been introduced. The amplification product was digested with these enzymes and the digestion product containing the HBsAg gene was ligated to the nine kilobase pair fragment of the plasmid pDX10a digested with the same enzymes. Plasmid pDX10a is a derivative of pUC19 having ClaI/XhoI restriction sites that bracket the coat protein coding sequence of the PVX genome. This produced a plasmid, pDX10a-HBV6, that contained a full-length infectious cDNA clone of PVX strain DX, under the control of a T7 promoter, in which the coat protein gene of PVX was replaced with the gene for HBsAg. The construct was designed so that HBsAg expression would be driven through the production of a mRNA encoding HBsAg from the subgenomic promoter that naturally directs the production of the subgenomic mRNA for the PVX coat protein.

The pDX10a-HBV6 DNA was linearized with the restriction enzyme SpeI and the linearized DNA transcribed in vitro with T7 polymerase using an Ambion T7 mMessage mMachine kit according to the manufacturer's instructions. Transcription products were manually inoculated onto *Nicotiana benthamiana* plants transgenically expressing the PVX coat protein. The modified form of the virus produced systemic infections on plants when transgenically complemented for the deleted viral gene, the coat protein. SDS-PAGE and Western blot analysis of extracts from infected plants demonstrated the expression of two proteins that were immunoreactive with HBsAg specific antiserum: these were presumed to represent glycosylated and non-glycosylated forms of the virally expressed HBsAg protein.

Purification of the in planta, virally expressed HBsAg protein was attempted using a modified form of the procedure described by Mason et al. (1992) to permit its characterization. Systemically infected leaf tissue was homogenized in four volumes of extraction buffer using a pestle and mortar. The homogenate was centrifuged at 1000×g for 5 minutes, and the supernatant was centrifuged at 27,000×g for 15 minutes. The 27,000×g supernatant was centrifuged at 100,000×g for 1 hour. Aliquots of the crude homogenate and supernatants from each of the centrifugation steps were taken for SDS-PAGE and Western blot analysis with HBsAg specific antiserum. Visual inspection of the western blot showed that there was no significant pelleting of the HBsAg during the first low speed centrifugation, but that there was significant loss of the expressed protein during the second centrifugation step and that the majority of the residual soluble HBsAg was pelleted during the third high speed centrifugation. The observation that substantial quantities of HBsAg were lost during the intermediate speed centrifugation suggested that the protein was inefficiently extracted with the buffer used, possibly because of its known membrane associating characteristics. Therefore to test whether extraction of the protein could be enhanced its extraction was attempted with buffers containing different levels of detergent.

Systemically infected leaf tissue was homogenized in two volumes of buffer containing 0.1M sodium phosphate (pH 7.0) and 0.1M sodium ascorbate using a pestle and mortar. Aliquots of 5 mL of the crude homogenate were taken and homogenized for a further 2 minutes in pestle and mortars with an equal volume of buffer supplemented with either 0.2%, 1%, 2%, 5% or 10% Triton X-100, as a representative non-ionic detergent. The homogenates were incubated on ice for one hour and then subjected to centrifugation at 27,000×g for 15 minutes. Equal quantities of crude homogenate and supernatants from each of the five extraction procedures were taken for SDS-PAGE and western blot analysis with HBsAg specific antiserum. Visual inspection of the western blot showed that in the absence of detergent HBsAg was recovered with very low efficiency in the supernatant after centrifugation, but that extraction with a final concentration of 1% or higher Triton X-100 resulted in efficient recovery. Thus, increasing the level of detergent up to 1% resulted in more efficient extraction of the desired protein.

However the efficacy of HBsAg as an immunogen is dependent upon its aggregation state, the particulate form being more immunogenic that free protein. Therefore, HBsAg extracted with 0.1%, 0.5% and 1.0%, final concentration, Triton X-100 was further analyzed by rate zonal centrifugation discontinuous 32 mL sucrose gradients were made in 10 mM sodium phosphate (pH 7.0) and 0.15 M sodium chloride (8 mL each of 5%, 13.3%, 21.6% and 30% sucrose) and left to diffuse overnight at 4° C. 2 mL of the 27,000 ×g supernatants were loaded onto gradients and centrifuged in a Sorvall AH629 rotor at 29,000 rpm for 6 hours at 5° C. 2 mL fractions were collected from the three gradients and aliquots analyzed by SDS-PAGE and Western blotting. Inspection of the Western blot of the fractions from the gradient loaded with material extracted with 1% Triton X-100 showed that virtually all the HBsAg related protein was present in the four fractions from the top of the gradient indicating that the HBsAg lipoprotein complexes had been completely solubilized with this level of detergent. In contrast, the Western blot of the fractions from the gradient loaded with material extracted with 0.1% Triton X-100 showed a broad peak in the fractions from the middle of the gradient indicating that the HBsAg extracted was in the desired particulate form. Inspection of the western blot of the fractions from the third sucrose gradient showed that the majority of the HBsAg had been completely solubilized by extraction with this level of detergent, as with the 1% Triton X-100.

Therefore, although the level of HBsAg extraction can be improved by increasing the level of detergent above the 0.1% used by Mason et al., use of 0.5% or higher concentrations of Triton X-100 results in disruption of the particulate form of HBsAg that may be most efficacious for use as a vaccine. Thus, levels of detergent less than 0.5% should be used for antigen purification unless it is intended to reconstitute particles or completely solubilized protein is desired. In conclusion, levels of greater than or equal to 0.1%, but less than 0.5% Triton X-100 appear optimal for extraction of the particulate form of HBsAg expressed in planta.

Example 26

An immune response to hepatitis B surface antigen (HBsAg) can be obtained when the antigen is expressed in a plant and the plant material is fed to the animal when the animal is immunoreceptive to the HBsAg. An animal may be made immunoreceptive to HBsAg by administering the plant material containing HBsAg in conjunction with a suitable adjuvant. The animal may also be immunoreceptive due to a prior, e.g. primary, immunization in which case an immune response to HBsAg may be boosted in the animal by feeding the animal the plant material containing the HBsAg.

The lines of potatoes expressing HBsAg selected for use in accordance with examples 27 to 30 are transformed lines from *S. tuberosum* L. c.v. Frito-Lay 1607 HB-7. The transformed lines are designated FL-1607 HB-7 and HB114–16. To obtain these lines, the HBsAg gene from a pMT-SA clone of a Chinese adr isolate of HBV was inserted into transformation plasmid vectors (pHB-7 and pHB114) that were mobilized into *Agrobacterium tumefaciens* (LBA4404) that was then used to transform *Solanum tuberosum* L cv. "Frito-Lay 1607.". The plasmid vectors used to construct the potato lines pHB-7 and pHB114–16 used in these examples both contain the gene for neomycin phosphotransferase (NPTII, also known as APH(3')II). This gene also becomes integrated into the potato genome and is expressed in the potato cells. *E. coli* derived NPTII has been shown to be biochemically equivalent to plant expressed NPTII. The *E. coli* derived NPTII degrades rapidly under conditions of simulated mammalian digestion and has been shown to cause no deleterious effects when purified protein was fed to mice at up to 5 g/kg body weight. The transformed FL-1607 was cured of the *A. tumefaciens* and clonally propagated and the FL-1607 HB-7 and HB114–16 lines were selected for their high level of HBsAg expression. Extracts of the FL-1607 transformed lines were tested for HBsAg concentration by ELISA techniques. HB-7 averaged 1100 ng HBsAg per gram of tuber weight and HB14–16 averaged 8500 ng±2100 ng of HBsAg per gram of tuber weight.

The extracted HBsAg spontaneously forms virus like particles (VLPs) that sediment at the same density as yeast derived HBsAg VLPs. Electrophoretic mobility and western blot analysis indicate that the tuber expressed antigen is indistinguishable from yeast derived antigen.

The lines were clonally propagated to multiply the number of plants and potted in soil to produce the tubers used in the examples. The transformed lines were maintained by in vitro clonal propagation.

The untransformed parent potato line, FL-1607, was maintained by clonal propagation and potted to produce tubers that were used as the placebo control. The tissues from these tubers do not express any proteins that are reactive with reagents to detect HBsAg.

Example 27

BALB/c mice were fed either peeled HB-7 potato slices or control non-transformed potatoes. Each group of mice was given three 5 gm feedings of potato on days 0,7, and 14. The B subunit of cholera toxin (CT) (Sigma) was used as an oral adjuvant. Ten μg of the adjuvant was placed on the potato slices (both experimental and control) and consumed by the animals in conjunction with the antigen. The animals fed HB-7 therefore received an average of 5.5 μg HBsAg per feeding, or a total average does of 16.5 μg HBsAg over the 3 feedings provided.

Mice fed HB-7 developed serum IgM and IgG responses that were specific to HBsAg, whereas the group of animals fed control non-transformed potatoes failed to make any antibodies. After the third feeding an immune response was observed that peaked at around 70 mIU/ml. After a single i.p. inoculation of 0.5 μg of yeast derived recombinant HBsAg (rHBsAg) in alum (a normally subimmunogenic dose) a strong secondary response was observed that peaked at around 1700 mIU/ml. This response was predominantly IgG. No primary or secondary response was seen in the control mice fed non-transgenic potato and CT. Without the oral adjuvant, there was no significant response to HBsAg.

Example 28

In the Frito-Lay 1607 HB114–16 line expression is driven from the 35S promoter and average tuber expression in the lot used for these experiments was 8.37 μg HBsAg/gm wet weight of tuber.

Groups of BALB/c mice (5/group) were fed either with HB114–16 or with control non-transgenic potato. In both cases 10 μg CT was added to the potato. The feeding was repeated one and two weeks later. The total average dose to each mouse of HBsAg in the transgenic potato was 125.55 μg over the 3-week period. Then, at the later of 70 days following the first feed or at 3–6 weeks after the initial immune response had returned to baseline levels, the mice were immunized with a sub-immunogenic (0.5 μg) dose of rHBsAg (Merck) delivered in aluminum adjuvant by subcutaneous (s.c.) injection.

At these dose levels an initial immune response was seen immediately after the second feeding. This immune response continued to rise and peaked at around 6 weeks at 100 mIU/ml. A titer of only 10 mIU/ml in a human after a three dose of a current licensed injectable hepatitis B vaccine is considered to reflect successful immunization. The response returned to baseline at 13 weeks and at 16 weeks the animals were given the boost dose of rHBsAg. This led to an immediate rise in immune titer to >3000 mIU/ml, which remained over 1000 mlU/ml for the remainder of the experiment (40 weeks). This established that the primary immunization generated antigen specific immune memory cells that were rapidly and strongly recalled upon secondary boosting.

The control animals for this experiment that were given non-transgenic potato+CT did not develop a significant immune response to HBsAg and upon secondary challenge with the subimmunogenic dose, as described above, no secondary response was seen, establishing the specificity of the HBsAg results. Controls given transgenic potato without CT only developed a low level, i.e. 10 mIU/ml titer for a primary response that returned to baseline in only one week. Further challenge with the subimmunogenic dose as described above only gave a secondary response of 50 mIU/ml and return to only 10 mIU/ml in only two weeks.

Example 29

The transgenic potato has also been used to boost a pre-existing sub-immunogenic dose of rHBsAg in mice. In this experiment groups of BALB/c mice (5/group) were immunized with a sub-immunogenic dose of rHBsAg (Merck) delivered s.c. in alum. 5 weeks later each mouse was fed either with HB114–16 or with control non-transgenic potato. In both cases 10 μg CT was added to the potato. The feeding was repeated one and two weeks later. The total average dose to each mouse was 125.55 μg over the 3-week period.

A secondary response developed that had started to appear at the time of the third feeding and which rose to approximately 100 mIU/ml 11 weeks after the initial priming immunization before declining. In a control group no immune response developed in the group fed the non-transgenic potato.

Example 30

Forty two human subjects testing free of HIV and being previously immunized with a commercial HB vaccine and after an extended time having anti-HBsAg titers below 115 mIU/ml, were fed potatoes containing HBsAg or an HBsAg free potato control in a randomized double blind study. When the code was broken, it was determined that Group 1 was a control group that received three doses of 100 grams of nontransgenic potato FL-1607. Group 2 received two doses of 100 grams each of transgenic potato FL-1607 HB114–16 and one dose of nontransgenic FL-1607 potato. Group 3 received three doses of 100 grams each of transgenic potato FL-1607 HB114–16.

Available pre-clinical data indicate that (1) on a weight basis, mice freely consume of up to 25% of their body weight in potato without evidence of toxicity and (2) a 50 μg dose of HBsAg in 5 gm of potato is immunogenic as a primary series with an oral adjuvant. The available clinical data with other potato vaccines indicate that (1) consumption of 100 gm of raw potato is generally well tolerated and (2) on a weight basis, 100 gm consumed by a 70 kg person would represent 0.14% of body weight. This amount is approximately 178-fold less than has been consumed, by weight, in mice in pre-clinical experiments.

Thus, in the example for humans, 100 to 110 gm of potato was ingested by volunteers per dose. The clinical lot scheduled for use in this study contained 8.5±2.1 μg of HBsAg per gm of potato. Subjects who received two 100 gm doses of transgenic potato received a total dose of 1,280 to 2,120 μg of HBsAg and subjects receiving three doses received a total of 1,920 to 3,180 μg of HBsAg over the course of 28 days.

On each day of dosing (days 0, 14 and 28) the appropriate number of potatoes for each group (placebo and control) were separately removed and processed into individual 100 to 110 gm doses by pharmacy personnel using clean techniques. Briefly, selected potatoes were washed, peeled, diced and placed into an ice-cold water bath. Peeling of the potatoes was done to remove the skin that contains the alkaloid solanine. This alkaloid can cause abdominal discomfort or nausea and may cause a bitter taste. Following peeling and dicing, 100 to 110 gm doses of potato was weighed out for each study subject according to group assignment and Subject Identification Number (SID). Peels and any unused portions of potatoes were collected and processed for destruction. Aliquots of potato for each study subject was kept under water to prevent browning from oxidation between the time the potato was diced until the study subject consumed it. An appropriate sample of processed potato from each group at each feeding was retained and frozen for further processing to verify antigen content.

The subjects were tested for anti-HBsAg titer on the days shown in Tables 8, 9, and 10. The results clearly show an increased response to the administered HBsAg antigen as a result of ingesting of the genetically transformed potatoes. Over 60 percent of the subjects receiving three doses of potatoes containing HBsAg showed a significant increase in immune response. The tables clearly indicate that, in many cases, ingesting of plant material containing genetically expressed HBsAg can act as an effective booster for primary HB vaccination. None of the control subjects that received three doses of non-transgenic control potatoes had any change in antibody titer over the entire course of the observation.

TABLE 8

Group 1 (Received 3 doses of Nontransgenic potato tuber)
Titer (lm/ml)

| Volunteers | Day 0 | Day 7 | Day 14 | Day 21 | Day 28 | Day 35 | Day 42 | Day 56 |
|---|---|---|---|---|---|---|---|---|
| 1 | 72 | 64 | 73 | 74 | 78 | 78 | 63 | 57 |
| 2 | 17 | 14 | 12 | 12 | 2 | 5 | 10 | * |
| 3 | 63 | 51 | 56 | 67 | 69 | 74 | 88 | 89 |
| 4 | 66 | 78 | 52 | 62 | 54 | 74 | 67 | 69 |
| 5 | 0 | 0 | 0 | 1 | 0 | 0 | * | 7 |
| 6 | 12 | 9 | 12 | 18 | 18 | 16 | 17 | 19 |
| 7 | 34 | 28 | 24 | 32 | 33 | 29 | 34 | 33 |
| 8 | 9 | 11 | 12 | 11 | 8 | 7 | 9 | 9 |
| 9 | 104 | 99 | 83 | 110 | 120 | 100 | 99 | 92 |

* No Sample Drawn

TABLE 9

Group 2 (Received 2 doses of Transgenic & 1 dose of Nontransgenic potato tuber)
Titer (mIU/ml)

| 5 Volunteers | Day 0 | Day 7 | Day 14 | Day 21 | Day 28 | Day 35 | Day 42 | Day 56 |
|---|---|---|---|---|---|---|---|---|
| 1 | 29 | 29 | 29 | 29 | 29 | 29 | 47 | 93 |
| 2 | 8 | 15 | 27 | 49 | 41 | 40 | 73 | 79 |
| 3 | 170 | 161 | 158 | 144 | 130 | 144 | * | 132 |
| 4 | 32 | 32 | 31 | 34 | 33 | 23 | * | 42 |
| 5 | 13 | 15 | 15 | 14 | 11 | 11 | 17 | 17 |
| 6 | 43 | 37 | 46 | 77 | 69 | 85 | 85 | 78 |
| 7 | 67 | 37 | 47 | 57 | 80 | 89 | 77 | 73 |
| 8 | 11 | 7 | 114 | 114 | 136 | 176 | 191 | 200 |
| 9 | 104 | 126 | 262 | 269 | 318 | 313 | 357 | 390 |
| 10 | 33 | 26 | 22 | 21 | 21 | 25 | 25 | 29 |
| 11 | 107 | 92 | 96 | 89 | 93 | 83 | 95 | 90 |
| 12 | 21 | 22 | 55 | 112 | 120 | 219 | 395 | 458 |
| 13 | 65 | 68 | 66 | 63 | 89 | 103 | 137 | 258 |
| 14 | 20 | 24 | 18 | 15 | 12 | 12 | 15 | 20 |
| 15 | 0 | 0 | 0 | 0 | 0 | 0 | 0 | 0 |

TABLE 9-continued

Group 2 (Received 2 doses of Transgenic & 1 dose of Nontransgenic potato tuber)
Titer (mIU/ml)

| 5 Volunteers | Day 0 | Day 7 | Day 14 | Day 21 | Day 28 | Day 35 | Day 42 | Day 56 |
|---|---|---|---|---|---|---|---|---|
| 16 | 97 | 93 | 112 | 109 | 128 | 294 | 454 | 432 |
| 17 | 26 | 34 | 197 | 330 | 353 | 360 | 707 | 863 |

\* No Sample Drawn

TABLE 10

Group 3 (Received 3 doses of Transgenic potato tuber)
Titer (mIU/ml)

| Volunteers | Day 0 | Day 7 | Day 14 | Day 21 | Day 28 | Day 35 | Day 42 | Day 56 |
|---|---|---|---|---|---|---|---|---|
| 1 | 17 | 20 | 70 | 140 | 269 | 428 | 401 | 463 |
| 2 | 94 | 87 | 100 | 99 | 88 | 79 | 87 | 88 |
| 3 | 33 | 34 | 32 | 33 | 27 | 34 | 31 | 32 |
| 4 | 0 | 0 | 0 | 0 | 0 | 0 | 0 | 0 |
| 5 | 9 | 9 | 53 | 74 | 74 | 85 | 65 | 61 |
| 6 | 20 | 41 | 57 | 84 | 452 | 475 | 897 | 652 |
| 7 | 85 | 76 | 496 | 1212 | 3058 | 3572 | 4152 | 4526 |
| 8 | 13 | 19 | 19 | 15 | 28 | 14 | 20 | 21 |
| 9 | 120 | 236 | 282 | 390 | 605 | 667 | 1583 | 1717 |
| 10 | 9 | 11 | 14 | 13 | 13 | 18 | 11 | 15 |
| 11 | 0 | 0 | 0 | 0 | 0 | 0 | 0 | 0 |
| 12 | 72 | 77 | 137 | 270 | 349 | 523 | 1098 | 1226 |
| 13 | 85 | 76 | 84 | 74 | 111 | 215 | 175 | 163 |
| 14 | 40 | 35 | 39 | 71 | 119 | 122 | 330 | 430 |
| 15 | 56 | 51 | 59 | 85 | 252 | 407 | 520 | 745 |
| 16 | 115 | 213 | 511 | 1054 | 1964 | 3069 | 2966 | 3449 |

We claim:

1. A plant expression vector comprising two expression cassettes, wherein the first expression cassette comprises a first polynucleotide sequence encoding an antigen polypeptide and wherein the second expression cassette comprises a second polynucleotide sequence encoding said antigen polypeptide encoded by said first polynucleotide sequence, wherein said first polynucleotide sequence is non-identical to said second polynucleotide sequence.

2. The plant expression vector of claim 1, wherein the first cassette comprises a first polynucleotide sequence encoding a hepatitis B surface antigen (HBsAg) polypeptide and wherein the second expression cassette comprises a second non-identical polynucleotide sequence encoding the same HbsAg polypeptide encoded by said first polynucleotide sequence.

3. The plant expression vector of claim 2, wherein the first expression cassette comprises a first polynucleotide sequence encoding a HBsAg polypeptide wherein said first polynucleotide sequence is plant-optimized, and wherein the second expression cassette comprises a second polynucleotide sequence encoding said HBsAg polypeptide encoded by said first polynucleotide wherein said second polynucleotide sequence is native virus derived.

4. The plant expression vector of claim 3 wherein the polynucleotide of the first expression cassette comprises SEQ ID NO:3 and wherein the polynucleotide of the second expression cassette comprises SEQ ID NO:1.

5. The plant expression vector of claim 1, wherein gene silencing is reduced or eliminated when both of said polynucleotides are expressed in a cell.

6. The plant expression vector of claim 5 wherein the gene silencing is RNA-mediated transcriptional gene silencing.

7. The plant expression vector of claim 1 wherein the polynucleotide of the first expression cassette and the polynucleotide of the second expression cassette comprise no more than 90 contiguous identical nucleotides.

8. The plant expression vector of claim 1 wherein the polynucleotide of the first expression cassette and the polynucleotide of the second expression cassette comprise no more than 60 contiguous identical nucleotides.

9. The plant expression vector of claim 1 wherein the first expression cassette further comprises a 5' transcribed, untranslated region and wherein the second expression cassette comprises a non-identical 5' transcribed, untranslated region.

10. The plant expression vector of claim 1 wherein the first expression cassette further comprises a 3' transcribed, untranslated region and wherein the second expression cassette comprises a non-identical 3' transcribed, untranslated region.

11. The plant expression vector of claim 1 wherein first expression cassette further comprises a 5' transcribed, untranslated region and a 3' transcribed, untranslated region and wherein the second expression cassette comprises a non-identical 5' transcribed, untranslated region and a non-identical 3' transcribed, untranslated region as compared to the first expression cassette.

12. The plant expression vector of claim 11 wherein the first expression cassette comprises a TEV 5' transcribed, untranslated region and a vspB 3' transcribed, untranslated region, and wherein the second expression cassette comprises a TMV 5' transcribed, untranslated region and a pin2 3' transcribed, untranslated region.

13. The plant expression vector of claim 12, wherein the first expression cassette comprises a first polynucleotide sequence encoding a HBsAg polypeptide wherein said first polynucleotide sequence is plant-optimized, and wherein the second expression cassette comprises a second polynucleotide sequence encoding said HBsAg polypeptide encoded by said first polynucleotide wherein said second polynucleotide sequence is native virus derived.

14. An *E. coli* cell transformed with the plant expression vector of claim 1.

15. The *E. coli* cell of claim 14 wherein virus like particles are assembled in the cell.

16. An Agrobacterium cell transformed with the plant expression vector of claim 1.

17. The Agrobacterium cell of claim 16 wherein virus like particles are assembled in the cell.

18. A polynucleotide comprising a nucleic acid sequence encoding a hepatitis B surface antigen (HBsAg) operably linked to:
(i) a plant finctional promoter;
(ii) a translation enhancement sequence; and
(iii) a termination sequence wherein, the polynucleotide lacks an untranslated region between the translation enhancement sequence and the HBsAg encoding sequence.

19. The polynucleotide of claim 18 wherein the nucleic acid sequence encoding the HBsAg comprises at least one altered codon, wherein the altered codon is a plant preferred codon.

20. The polynucleotide of claim 18, wherein said plant-functional promoter is selected from the group consisting of cauliflower mosaic virus (CaMV) 35S, tomato E8, ubiquitin, mannopine synthase, patatin, and granule-bound starch synthase (GBSS) promoters.

21. The polynucleotide of claim 18, wherein the promoter includes a dual enhancer region.

22. The polynucleotide of claim 18, wherein said translation enhancement sequence is selected from the group consisting of tobacco etch virus (TEV) and tobacco mosaic virus (TMV) omega translation enhancers.

23. The polynucleotide of claim 18, wherein said termination sequence is selected from the group consisting of a nopaline synthase (nos), a vegetative storage protein (vsp), or a proteinase inhibitor —2 (pin2) termination sequence.

24. The polynucleotide of claim 18, wherein the polynucleotide lacks an untranscribed region between the HBsAg encoding sequence and the termination sequence.

25. The polynucleotide of claim 18, further comprising a nucleic acid sequence encoding a microsomal retention signal operably linked to the 3' end of the HBsAg encoding sequence.

26. The polynucleotide of claim 25, wherein the microsomal retention signal is Ser-Glu-Lys-Asp-Glu-Leu (SEQ ID NO:4).

27. The polynucleotide of claim 25, wherein the polynucleotide lacks an untranscribed region between the microsomal retention signal and the termination sequence.

28. The polynucleotide of claim 18, further comprising a nucleic acid sequence encoding a signal polypeptide operably linked to the 5' end of the HBsAg encoding sequence.

29. The polynucleotide of claim 28, wherein the signal peptide is selected from the group consisting of a vegetative storage protein (VSP) αS signal peptide and a VSP GI signal peptide.

30. The polynucleotide of claim 18, wherein the HBsAg encoding sequence further comprises a pre-S region.

31. The polynucleotide of claim 18, wherein the HBsAg encoding sequence comprises the nucleic acid sequence optimized for expression in plants shown in SEQ ID NO:3.

32. The polynucleotide of claim 18 wherein the polynucleotide is selected from the group of polynucleotides consisting of HB104, HB105, HB106, HB107, HB111, HB114, HB115, HB116, HB117, HB118, HB119, HB120, HB121, HB122, HB123, HB131, HB140.3, HB145 and HB165.

33. An expression vector comprising the polynucleotide of claim 18.

34. The expression vector of claim 33 further comprising a selectable marker.

35. The expression vector of claim 33 further comprising an *E. coli* origin of replication.

36. The expression vector of claim 33 further comprising an Agrobacterium tumefaciens origin of replication.

37. An *E. coli* cell transformed with the expression vector of claim 33.

38. The *E. coli* cell of claim 37 wherein a virus like particle is assembled in the cell.

39. An Agrobacterium cell transformed with the expression vector of claim 33.

40. The Agrobacterium cell of claim 39 wherein a virus like particle is assembled in the cell.

41. The Agrobacterium cell of claim 39 further comprising a helper Ti plasmid.

* * * * *

UNITED STATES PATENT AND TRADEMARK OFFICE
CERTIFICATE OF CORRECTION

| | | |
|---|---|---|
| PATENT NO. | : 6,551,820 B1 | Page 1 of 1 |
| APPLICATION NO. | : 09/471573 | |
| DATED | : April 22, 2003 | |
| INVENTOR(S) | : Hugh S. Mason et al. | |

It is certified that error appears in the above-identified patent and that said Letters Patent is hereby corrected as shown below:

Column 1, line number 9, add the following heading and paragraph:

STATEMENT OF RIGHTS TO INVENTIONS MADE UNDER FEDERALLY SPONSORED RESEARCH

This work was supported by the following grant from the National Institutes of Health, Grant No.: NIH AI42836. The government may have certain rights in the invention.

Signed and Sealed this
Twenty-ninth Day of May, 2012

David J. Kappos
*Director of the United States Patent and Trademark Office*

UNITED STATES PATENT AND TRADEMARK OFFICE
CERTIFICATE OF CORRECTION

Page 1 of 1

PATENT NO. : 6,551,820 B1
APPLICATION NO. : 09/471573
DATED : April 22, 2003
INVENTOR(S) : Hugh S. Mason et al.

It is certified that error appears in the above-identified patent and that said Letters Patent is hereby corrected as shown below:

In The Specification,

Col. 1, line 9 insert

--This invention was made with government support under Grant Number NIHAI042836 awarded by the National Institutes of Health (NIH). The government has certain rights in the invention.--

This certificate supersedes the Certificate of Correction issued May 29, 2012.

Signed and Sealed this
Fourteenth Day of April, 2015

Michelle K. Lee
*Director of the United States Patent and Trademark Office*